US007527937B2

(12) United States Patent
Ohara et al.

(10) Patent No.: US 7,527,937 B2
(45) Date of Patent: May 5, 2009

(54) ASSAY EMPLOYING A G-PROTEIN COUPLED RECEPTOR THAT IS ACTIVATED BY CCK-8S

(75) Inventors: Osamu Ohara, Kisarazu (JP); Takahiro Nagase, Kisarazu (JP); Michio Ohishi, Kisarazu (JP); Daisuke Okajima, Tokyo (JP); Hiroshi Yokota, Tokyo (JP)

(73) Assignees: Daiichi Sankyo Company, Limited, Tokyo (JP); Kazusa DNA Research Institute Foundation, Chiba (JP)

( * ) Notice: Subject to any disclaimer, the term of this patent is extended or adjusted under 35 U.S.C. 154(b) by 0 days.

(21) Appl. No.: 11/436,904

(22) Filed: May 18, 2006

(65) Prior Publication Data

US 2006/0234305 A1     Oct. 19, 2006

Related U.S. Application Data

(63) Continuation-in-part of application No. PCT/JP2004/017239, filed on Nov. 19, 2004, and a continuation-in-part of application No. PCT/JP2006/309118, filed on May 1, 2006.

(30) Foreign Application Priority Data

| Nov. 19, 2003 | (JP) | ............................. 2003-389624 |
| Apr. 26, 2004 | (JP) | ............................. 2004-130371 |
| Oct. 19, 2004 | (JP) | ............................. 2004-304780 |
| May 2, 2005 | (JP) | ............................. 2005-134367 |

(51) Int. Cl.
*G01N 33/566* (2006.01)
*C07K 14/705* (2006.01)

(52) U.S. Cl. .................. 435/7.21; 435/7.1; 435/7.2; 436/501

(58) Field of Classification Search .................. None
See application file for complete search history.

(56) References Cited

U.S. PATENT DOCUMENTS

| 5,874,245 | A | 2/1999 | Fukusumi et al. |
| 2003/0113798 | A1 | 6/2003 | Burmer et al. |
| 2003/0143668 | A1 | 7/2003 | Suwa et al. |
| 2003/0235833 | A1 | 12/2003 | Suwa et al. |
| 2006/0134109 | A1 | 6/2006 | Gaitanaris et al. |

FOREIGN PATENT DOCUMENTS

| JP | 10-84976 | 4/1998 |
| JP | 11-32766 | 2/1999 |
| JP | 2003-284573 | 10/2003 |
| WO | WO 02/061087 A2 | 8/2002 |
| WO | WO 2005/049833 A1 | 6/2005 |

OTHER PUBLICATIONS

Flumann et al., A Human Orphan Calcitonin Receptor-Like Structure, Jan. 5, 1995, BBRC 206(1):341-347.*

Eva et al., Molecular Cloning of a Novel G protein-coupled Receptor that may belong to the Neuropeptide Receptor Family, Oct. 1990, FEBS Letters 271(1,2):81-84.*
Database Geneseq No. XP-002435010, "Human GPCR protein Seq Id No. 870," Jan. 1, 2004 (2 pages).
Database UniProt No. XP-002435011, "Brain-specific angiogenesis inhibtior 2 precursor," Jul. 11, 2006 (4 pages).
Database Geneseq No. XP-002435012, "Human brain-specific angiogenesis inhibitor 2 protein Seq Id No. 344," dated Mar. 4, 2003 (2 pages).
Bree et al., "Homolateral Cerebrocortical Changes in Neuropeptide and Receptor Expression After Minimal Cortical Infarction," Neuroscience, vol. 69, No. 3, 1995 (pp. 847-858).
Supplementary Partial European Search Report for European Patent Application No. 04 81 8967 dated May 24, 2007.
International Preliminary Report on Patentability for PCT/JP2004/017239 dated Aug. 3, 2006.
Dunlop et al., "Full and Partial Agonist Activity of C-terminal Cholecystokinin Peptides at the Cloned Human CCK-A Receptor Expressed in Chinese Hamster Ovary Cells," Peptides, vol. 18, No. 6, 1997 (pp. 865-868).
Shiratsuchi et al., "Cloning and characterization of BAI2 and BAI3, novel genes homologous to brain-specific angiogenesis inhibitor 1 (BAI1)," Cytogenetics and Cell Genetics, vol. 79, 1997 (pp. 103-108).
Nishimori et al., "A novel brain-specific p53-target gene, BAI1, containing thrombospondin type 1 repeats inhibits experimental angiogenesis," Oncogene, vol. 15, No. 18, Oct. 30, 1997 (pp. 2145-2150).
Kee et al., "Expression of Brain-Specific Angiogenesis Inhibitor 2 (BAI2) in Normal and Ischemic Brain: Involvement of BAI2 in the Ischemia-Induced Brain Angiogenesis," Journal of Cerebral Blood Flow and Metabolism, vol. 22, No. 9, 2002 (pp. 1054-1067).
Kaur et al., "Brain Angiogenesis Inhibitor 1 is Differentially Expressed in Normal Brain and Glioblastoma Independently of p53 Expression," American Journal of Pathology, vol. 162, No. 1, Jan. 2003 (pp. 19-27).
Shiratsuchi et al. "Cloning and Characterization of BAI-Associated Protein 1: A PDZ Domain-Containing Protein That Interacts with BAI1," Biochemical and Biophysical Research Communications, vol. 247, No. 3, Jun. 29, 1998 (pp. 597-604).
Ahréen et al., "Antidiabetogenic Action of Cholecystokinin-8 in Type 2 Diabetes," The Journal of Clinical Endocrinology & Metabolism, vol. 85, No. 3, 2000 (pp. 1043-1048).
Whalen et al., "Function Neuroimaging Studies of the Amygdala in Depression," Seminars in Clinical Neuropsychiatry, vol. 7, No. 4, Oct. 2002 (pp. 234-242).
Drevets, "Neuroimaging Abnormalities in the Amygdala in Mood Disorders," Ann. N.Y. Acad. Sci., vol. 985, 2003 (pp. 420-444).
Nestler et al., "Neurobiology of Depression," Neuron, vol. 34, Mar. 28, 2002 (pp. 13-25).

(Continued)

*Primary Examiner*—John D Ulm
(74) *Attorney, Agent, or Firm*—Kilyk & Bowersox, P.L.L.C.

(57) ABSTRACT

Methods of providing a protein having a function as a G-protein coupled receptor and methods of identifying a compound that inhibits or promotes a function of the protein and/or expression of a DNA encoding the protein are provided. Methods for identifying an anti-depressant drug or a compound That has an anti-depressant action and methods for diagnosing depression are also provided.

10 Claims, 9 Drawing Sheets

OTHER PUBLICATIONS

Herranz, "Cholecystokinin Antagonists: Pharmacological and Therapeutic Potential," Medicinal Research Reviews, vol. 23, No. 5, 2003 (pp. 559-605).

Nomoto et al., "Absence of the Cholecystokinin-A receptor deteriorates homeostasis of body temperature in response to changes in ambient temperature," Am. J. Physiol. Regulatory Integrative Comp. Physiol., vol. 287, Sep. 2004 (pp. 556-561).

Miyasaka et al., "Anxiety-related behaviors in cholecystokinin-A, B, and AB receptor gene knockout mice in the plus-maze," Neuroscience Letters, vol. 335, No. 2, Dec. 25, 2002 (pp. 115-118).

Bi et al., "Actions of CCK in the controls of food intake and body weight: Lessons from the CCK-A receptor deficient OLETF rat," Neuropeptides, vol. 36, Nos. 2 & 3, Apr./Jun. 2002 (pp. 171-181).

Noble et al., "Phenotypes of mice with invalidation of cholecystokinin ($CCK_1$ or $CCK_2$) receptors," Neuropeptides, vol. 36, Nos. 2 & 3, 2002 (pp. 157-170).

Horinouchi et al., "Reduced anxious behavior in mice lacking the CCK2 receptor gene," European Neuropsychopharmacology, vol. 14, 2004 (pp. 157-161).

Daugë et al., "Behavioral Profile of CCK2 Receptor-deficient Mice," Neuropsychopharmacology, vol. 25, No. 5, 2001 (pp. 690-698).

Kurrikoff et al., "Deletion of the CCK2 receptor gene reduced mechanical sensitivity and abolishes the development of hyperalgesia in mononeuropathic mice," European Journal of Neuroscience, vol. 20, 2004 (pp. 1577-1586).

Notification of Transmittal of Copies of Translation of the International Preliminary Report on Patentability for International Application No. PCT/JP2006/309118, dated Nov. 15, 2007, eight pages.

Extended European Search Report from counterpart European Patent Application No. 06745969.3 dated Jul. 28, 2008 (7 pages).

Kombian et al., "Chloecystokinin activities $CCK_8$ receptors to excite cells and depress EPSCs in the rat rostral nucleus accumbens *in vitro*," Journal of Physiology, vol. 555, No. 1, Feb. 15, 2004, pp. 71-84.

Database MGI, "Phenotypic Allele Detail," Sep. 2005 (1 page).

* cited by examiner

Figure 1-A
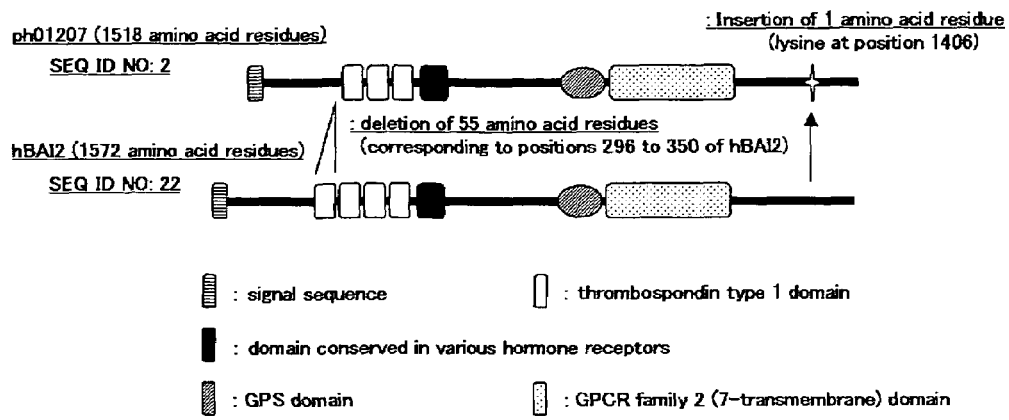
Figure 1-B
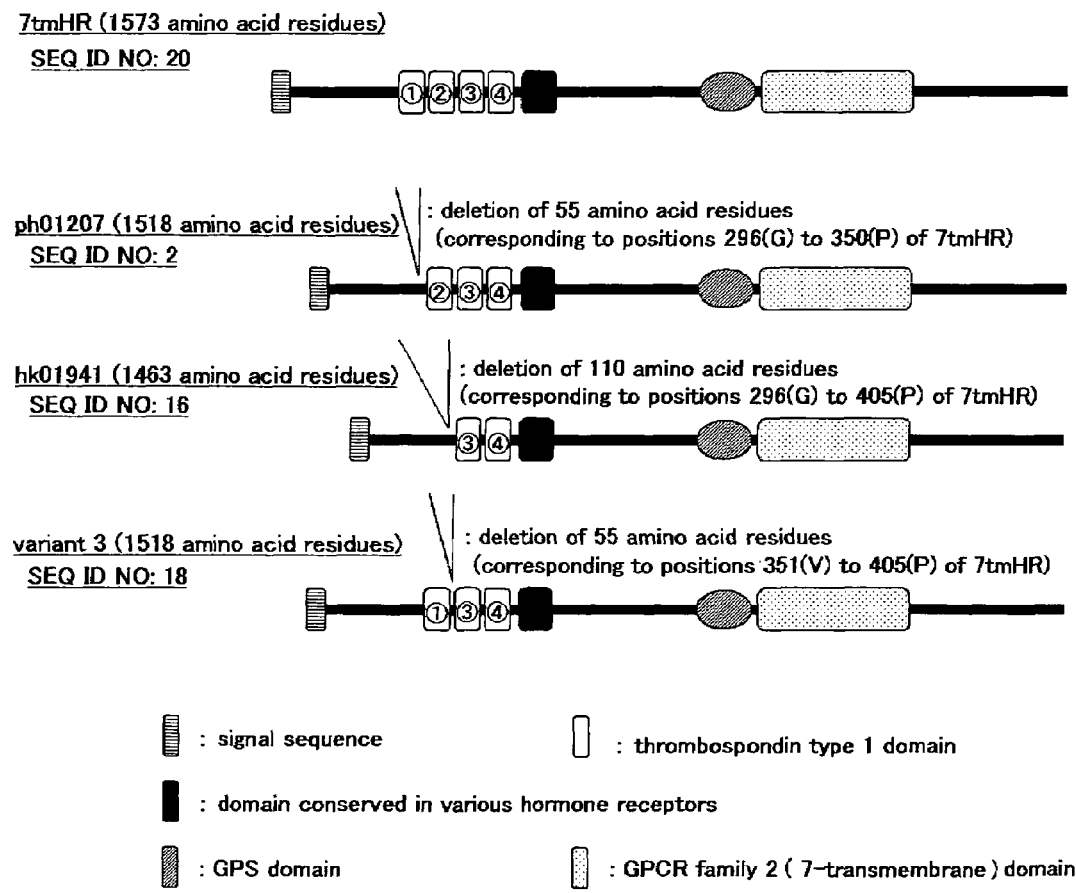

Figure 1-C

```
  1 : MTPACPLLLS VILSLRLATA FDPAPSACSA LASGVLYGAF SLQDLFPTIA SGCSWTLENP DPTKYSLYLR
                                              Forward primer
                                               (SEQ ID NO:22)
 71 : FNRQEQVCAH FAPRLLPLDH YLVNFTCLRP SPEEAVAQAE SEVGRPEEEE AEAAAGLELC SGSGPFTFLH 141 : FDKNFVQLCL SAEPSEAPRL LAPAALAFRF VEVLLINNNN SSQFTCGVLC RWSEECGRAA GRACGFAQPG 211 : CSCPGEAGAG STTTTSPGPP AAHTLSNALV PGGPAPPAEA DLHSGSSNDL FTTEMRYGEE PEEEPKVKTQ
```

|              |          |                                                                                              |
|--------------|----------|----------------------------------------------------------------------------------------------|
| (SEQ ID NO: 19) | 7tmHR    | 281 : WPRSADEPGL YMAQTGDPAA EEWSPWSVCS LTCGQGLQVR TRSCVSSPYG TLCSGPLRET RPCNNSATCP |
| (SEQ ID NO: 2)  | ph01207  | 281 : WPRSADEPGL YMAQT----- ---------- ---------- ---------- ---------- ---------- |
| (SEQ ID NO: 15) | hk01941  | 281 : WPRSADEPGL YMAQT----- ---------- ---------- ---------- ---------- ---------- |
| (SEQ ID NO: 17) | variant 3 | 281 : WPRSADEPGL YMAQTGDPAA EEWSPWSVCS LTCGQGLQVR TRSCVSSPYG TLCSGPLRET RPCNNSATCP |
|                 |           |                                              ①                                    |
| (SEQ ID NO: 19) | 7tmHR    | 351 : VHGVWEEWGS WSLCSRSCGR GSRSRMRTCV PPQHGGKACE GPELQTKLCS MAACPVEGQW LEWGPWGPCS |
| (SEQ ID NO: 2)  | ph01207  | 296 : VHGVWEEWGS WSLCSRSCGR GSRSRMRTCV PPQHGGKACE GPELQTKLCS MAACPVEGQW LEWGPWGPCS |
| (SEQ ID NO: 15) | hk01941  | 296 : ---------- ---------- ---------- ---------- ---------- -----VEGQW LEWGPWGPCS |
| (SEQ ID NO: 17) | variant 3 | 351 : ---------- ---------- ---------- ---------- ---------- -----VEGQW LEWGPWGPCS |
|                 |           |        ②                                                                   ③       |

```
421 : TSCANGTQQR SRKCSVAGPA WATCTGALTD TRECSNLECP ATDSKWGPWN AWSLCSKTCD TGWQRRFRMC
                                                 ④                    ◀────Reverse primer
                                                                          (SEQ ID NO:23)
491 : QATGTQGYPC EGTGEEVKPC SEKRCPAFHE MCRDEYVMLN TWKKAAAGEI IYNKCPPNAS GSASRRCLLS 561 : AQGVAYWGLP SFARCISHEY RYLYLSLREH LAKGQRMLAG EGMSQVVRSL QELLARRTYY SGDLLFSVDI 631 : LRNVTDTFKR ATYVPSADDV QRFFQVVSFM VDAENKEKWD DAQQVSPGSV HLLRVVEDFI HLVGDALKAF 701 : QSSLIVTDNL VISIQREPVS AVSSDITFPM RGRRGMKDWV RHSEDRLFLP KEVLSLSSPG KPATSGAAGS 771 : PGRGRGPGTV PPGPGHSHQR LLPADPDESS YFVIGAVLYR TLGLILPPPR PPLAVTSRVM TVTVRPPTQP 841 : PAEPLITVEL SYIINGTTDP HCASWDYSRA DASSGDWDTE NCQTLETQAA ETRCQCQHLS TFAVLAQPPK 911 : DLTLELAGSP SVPLVIGCAV SCMALLTLLA IYAAFWRFIK SERSIILLNF CLSILASNIL TLVGQSRVLS 981 : KGVCTMTAAF LHFFFLSSFC WVLTEAWQSY LAVIGRMRTR LVRKRFLCLG WGLPALVVAV SVGFTRTKGY 1051 : GTSSYCWLSL EGGLLYAEVG PAAVIVLVNM LIGIIVFNKL MARDGISDKS KKQRAGSERC PWASLLLPCS 1121 : ACGAVPSPLL SSASARNAMA SLWSSCVVLP LLALTWMSAV LAMTDRRSVL FQALFAVFNS AQGFVITAVH 1191 : CFLRREVQDV VKCQMGVCRA DESEDSPDSC KNGQLQILSD FEKDVDLACQ TVLFKEVNTC NPSTITGTLS 1261 : RLSLDEDEEP KSCLVGPEGS LSFSPLPGNL LVPMAASPGL GEPPPPQEAN PVYMCGEGGL RQLDLTWLRP 1331 : TEPGSEGDYM VLPRRTLSLQ PGGGGCGGED AFRARPEGTP RRAAKTVAHT EGYPSFLSVD HSGLGLGPAY 1401 : GSLQNPYGMT FQPPPPTPSA RQVPEPGERS RTMPRTVPGS TMKMGSLERK KLRYSDLDFE KVMHTRKRHS 1471 : ELYHELNQKF HTFDRYRSQS TAKREKRWSV SSGGAAERSV CTDKPSPGER PSLSQHRRHQ SWSTFKSMTL

1540 : GSLPPKPRER LTLHRAAAWE PTEPPDGDFQ TEV*
```

Figure 2
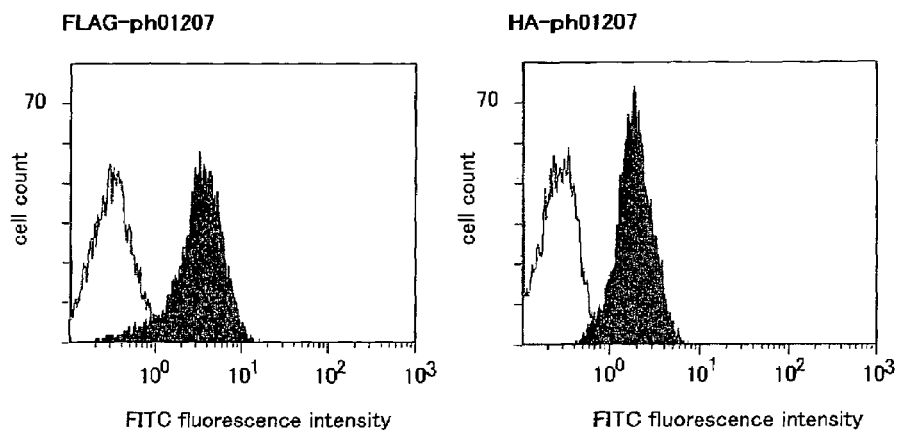
Figure 3
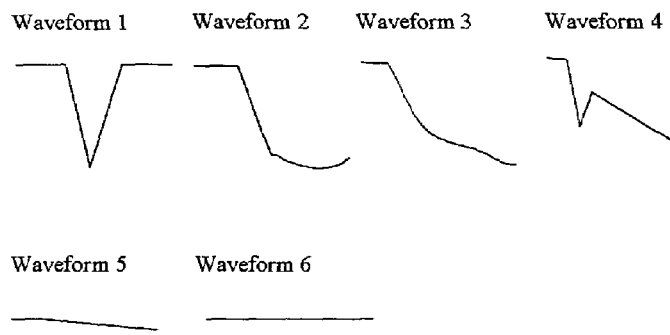
Figure 4-A
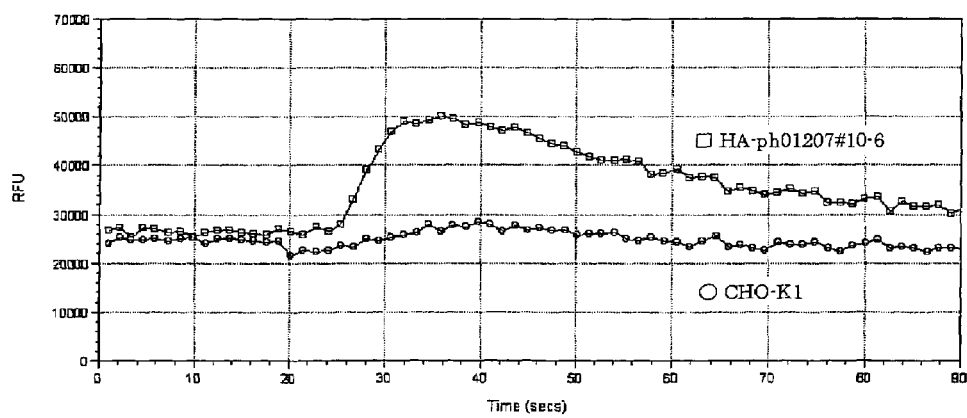

Figure 4-B
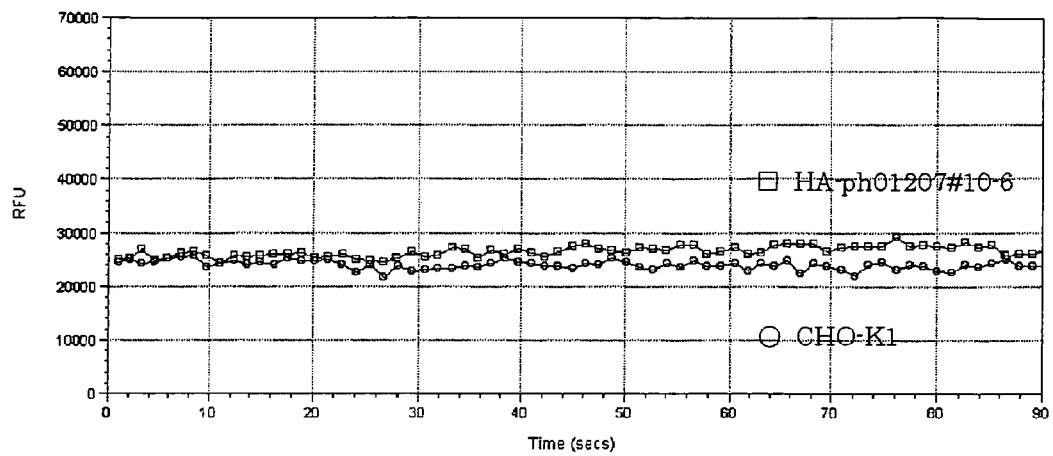
Figure 4-C
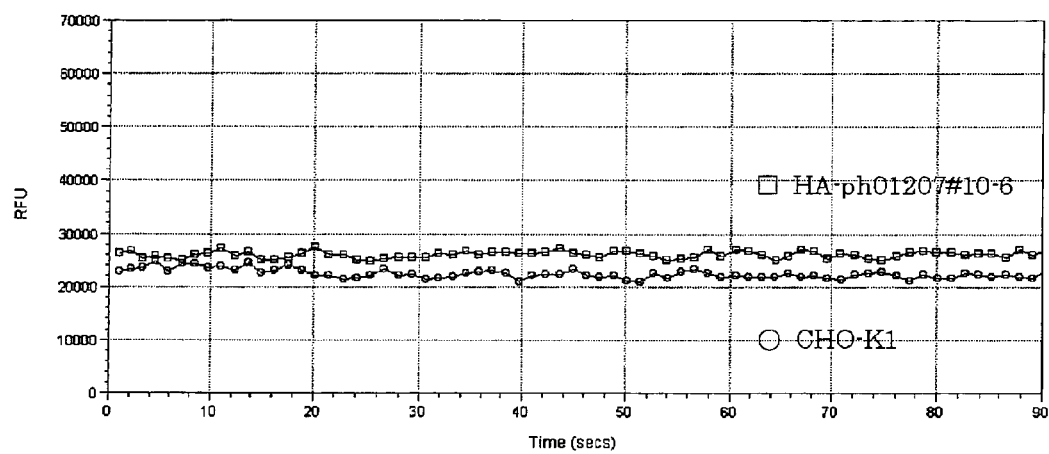
Figure 4-D
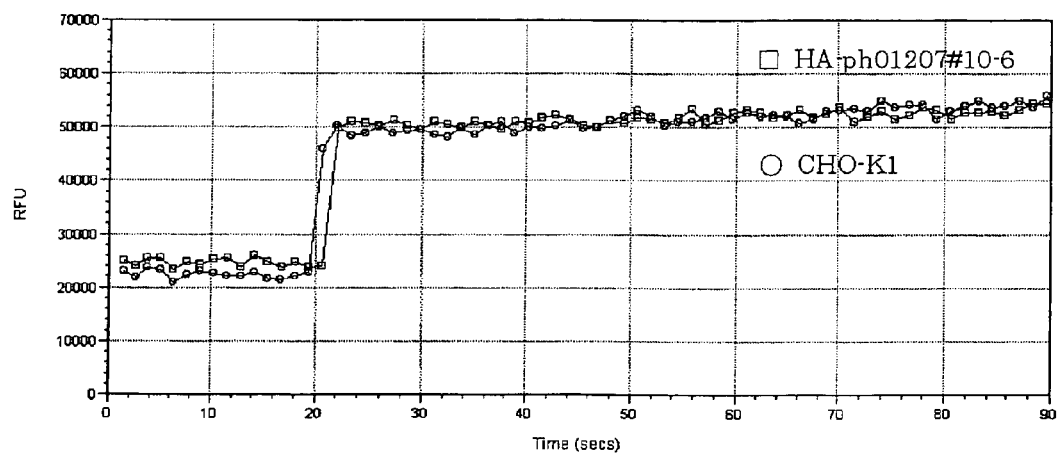

Figure 4-E
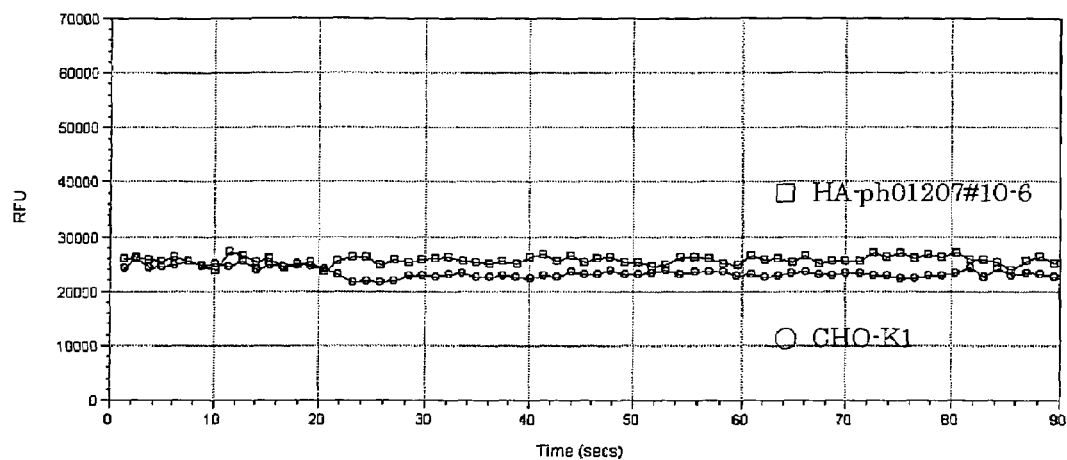
Figure 5-A
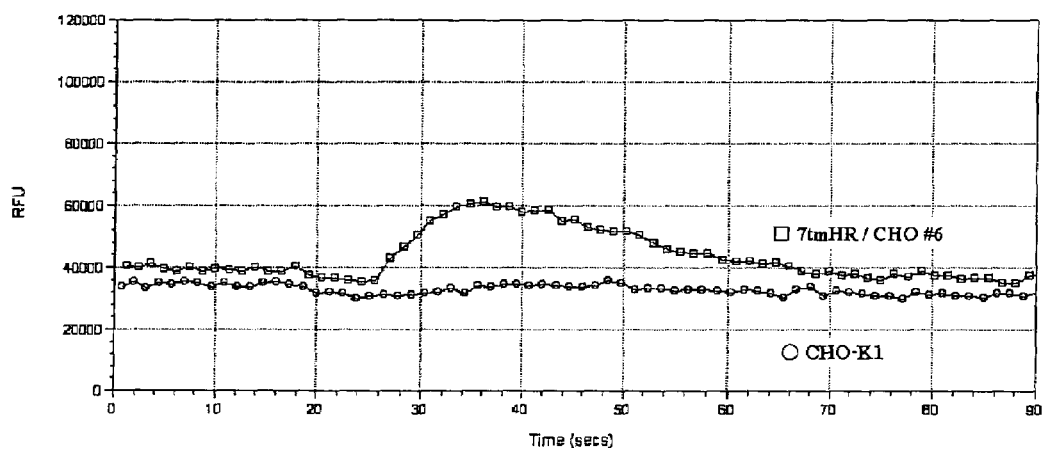
Figure 5-B
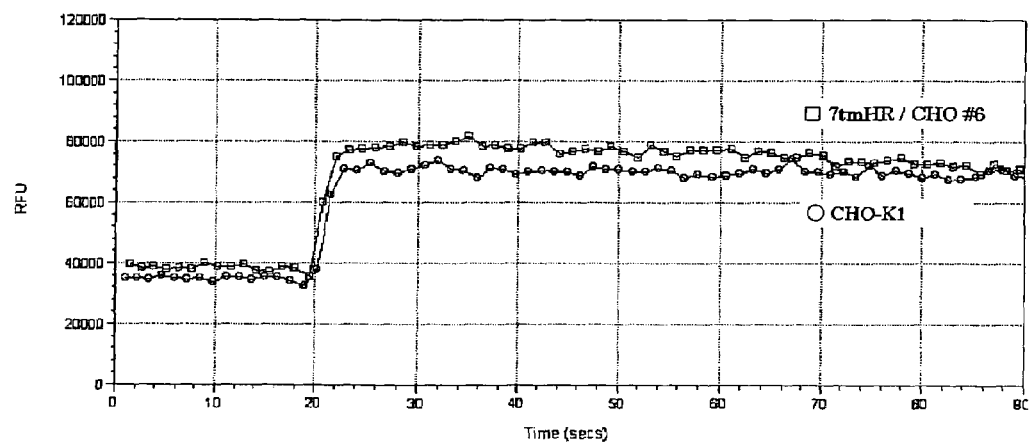

Figure 6-A
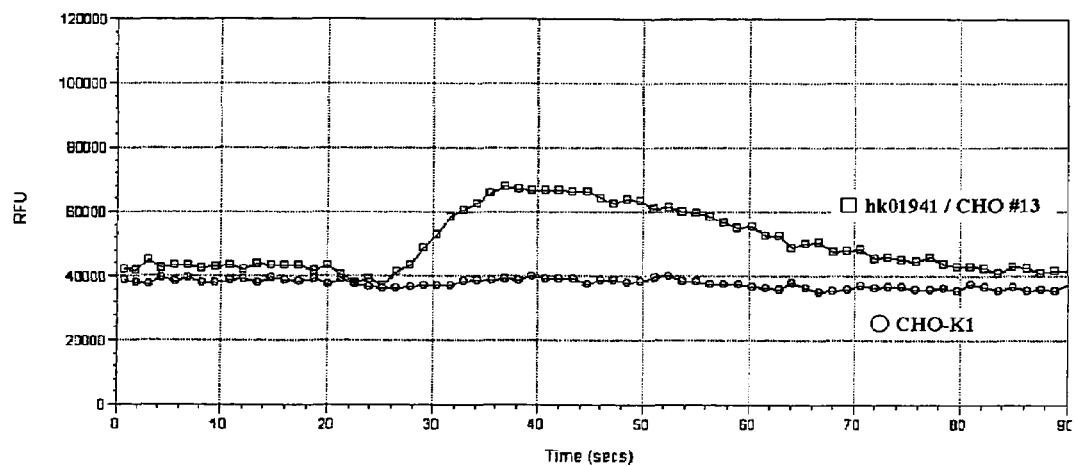
Figure 6-B
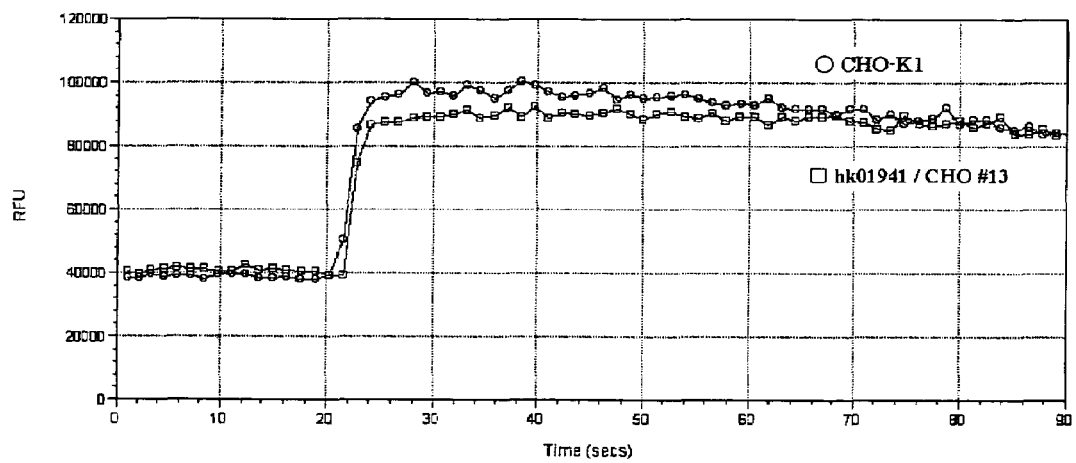
Figure 7-A
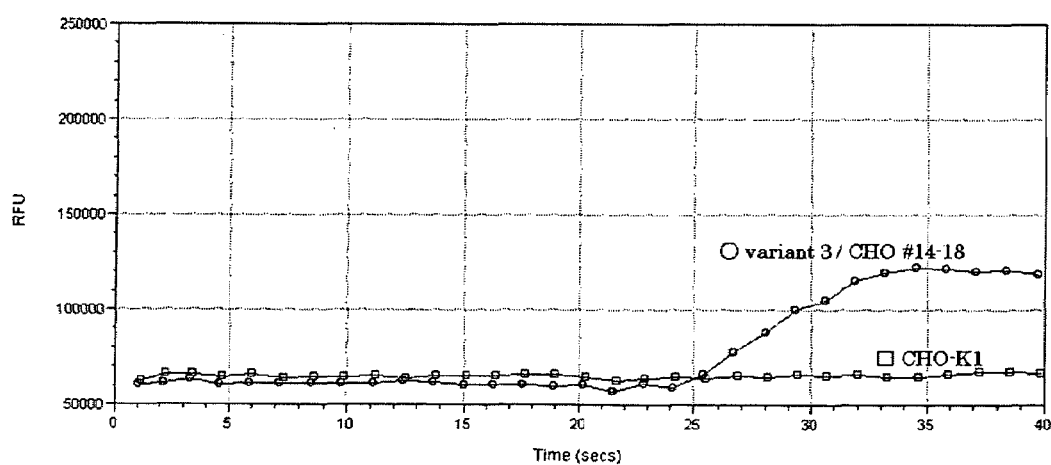

Figure 7-B
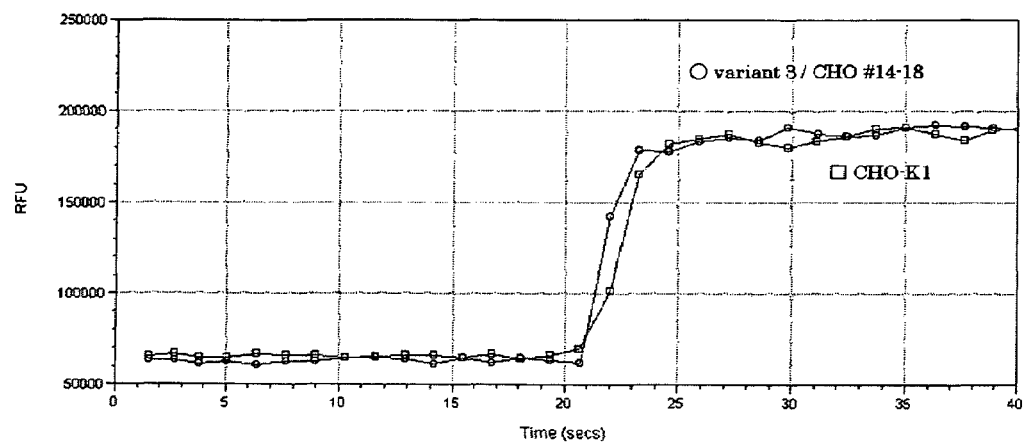
Figure 8-A
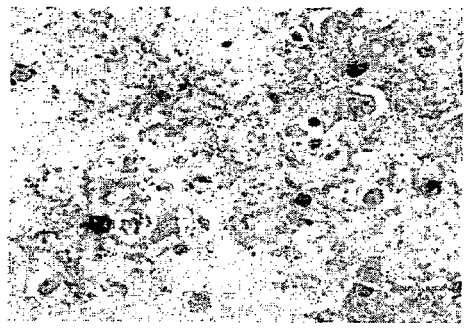
Figure 8-B
Figure 8-C
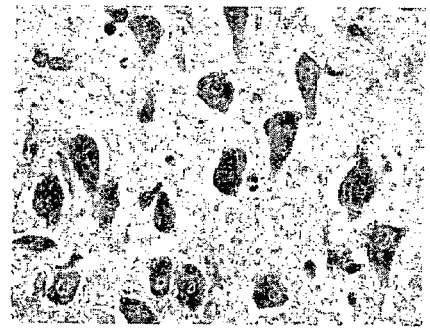

Figure 8-D
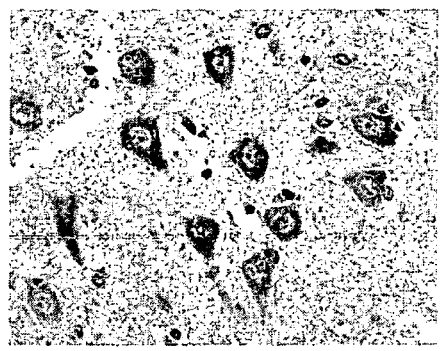
Figure 9-A
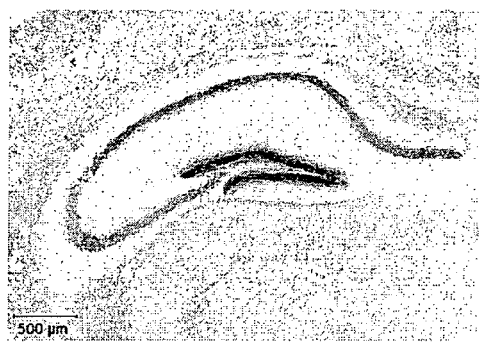
Figure9-B
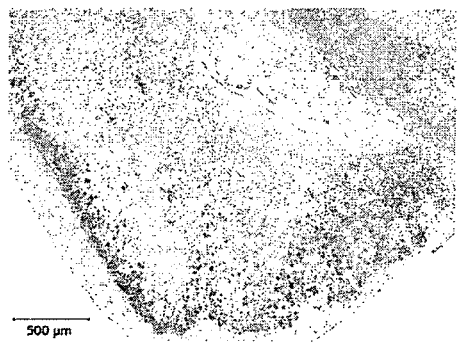
Figure 10
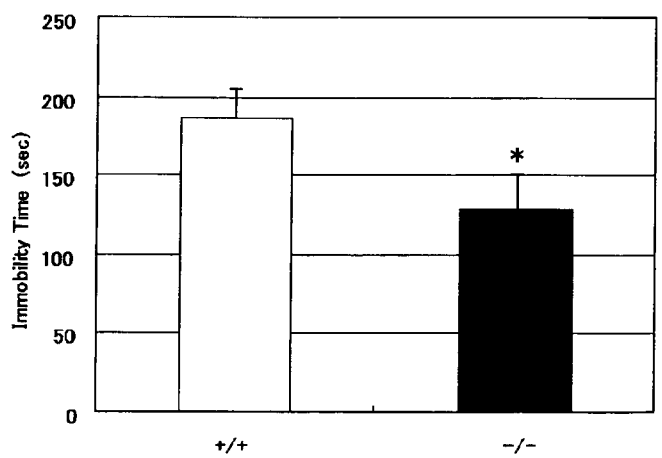

Figure 11-A
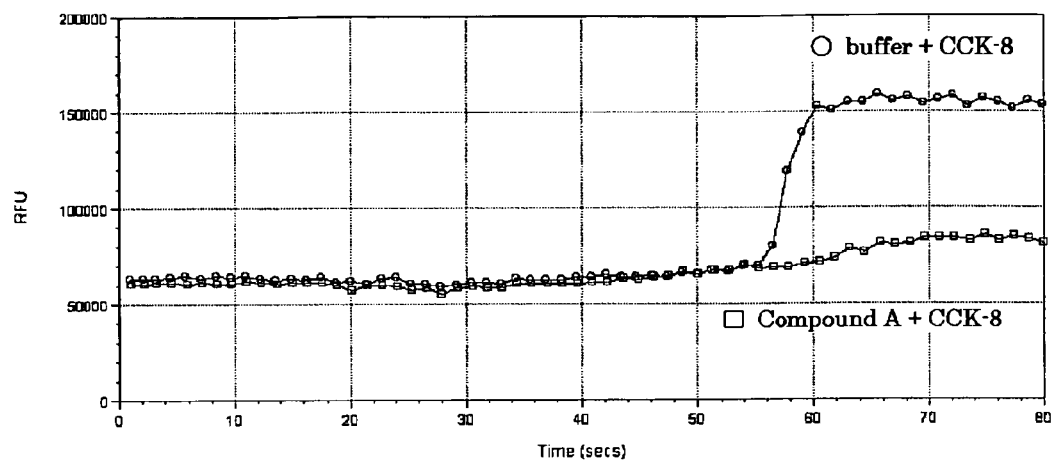
Figure 11-B
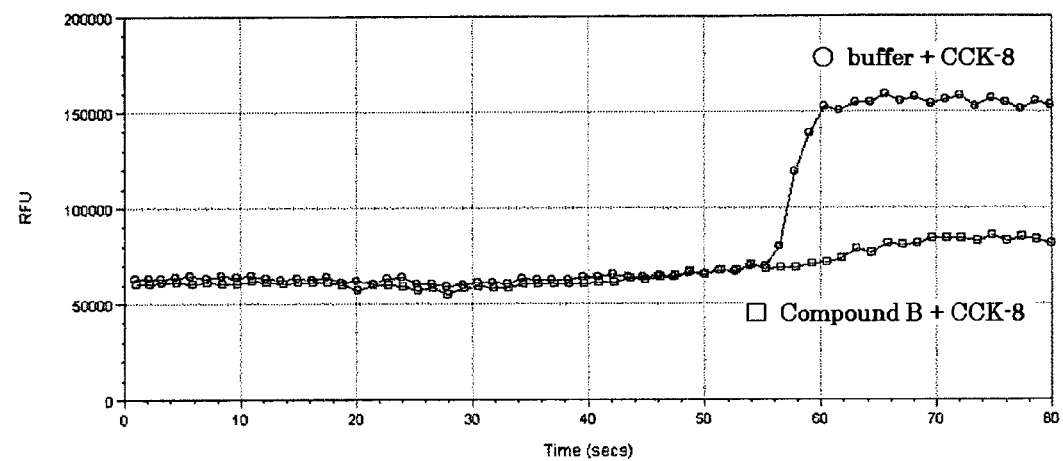
Figure 11-C
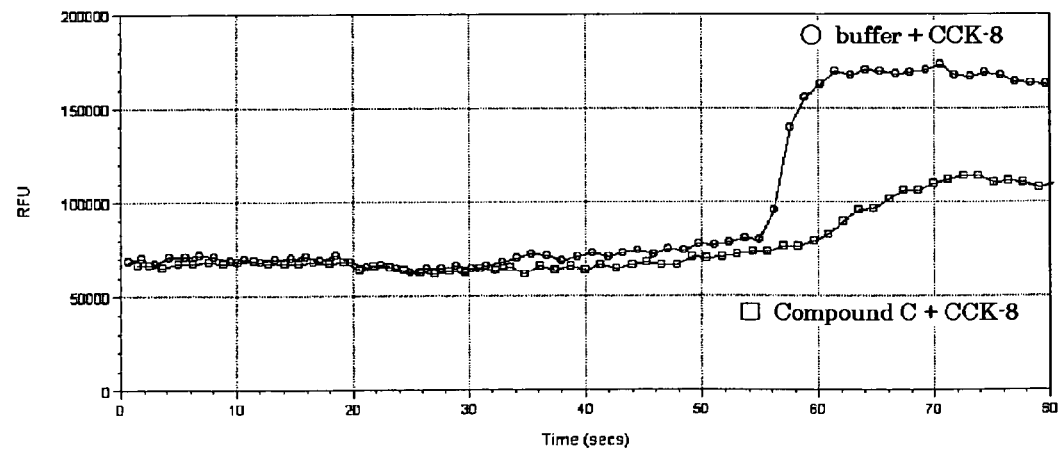

SEQUENCE LISTING

```
<160> NUMBER OF SEQ ID NOS: 24

<210> SEQ ID NO 1
<211> LENGTH: 4557
<212> TYPE: DNA
<213> ORGANISM: homo sapiens
<220> FEATURE:
<221> NAME/KEY: misc_feature
<223> OTHER INFORMATION: DNA encoding a novel functional membrane
      protein receptor

<400> SEQUENCE: 1 atgacccag  cctgtcccct  cttactgtct  gtgattctgt  ccctgcgcct  ggccaccgcc      60 ttcgacccg  cccccagtgc  ctgctctgcc  ctggcctcgg  gtgtgctcta  cggggccttc     120
```

```
tcgctgcagg acctctttcc taccatcgcc tcgggctgct cctggaccct ggagaaccct      180
gaccccacca agtactccct ctacctgcgc ttcaaccgcc aggagcaggt gtgcgcacac      240 tttgccccc  gcctgctgcc cctggaccac tacctggtca actttacctg cctgcggcct      300
agccccgagg aggcggtggc ccaggcggag tcagaggtgg ggcggccaga agaggaggag      360
gcagaggcgg cagcggggtt ggagctgtgc agcggctcag gccccttac  cttcctgcac      420 ttcgacaaga acttcgtgca gctgtgcctg tcggctgagc cctccgaggc cccgcgcctg      480
ctggcgcccg ctgccctagc cttccgcttt gtcgaggtct tgctcatcaa caacaacaac      540
tctagccaat tcacctgtgg tgtgctctgc cgctggagtg aggagtgtgg ccgcgctgcc      600
ggcagggcct gcggctttgc tcagccaggc tgcagctgcc ctggagaggc ggggggccggc     660 tccaccacca ccacatctcc aggccctcct gctgcccaca ccctgtccaa tgccctggtg      720
cccgggggcc cagccccacc tgctgaggcc gatttgcact cggggagcag caatgatctg      780
ttcacaaccg agatgagata tggtgaggag ccggaagagg aaccgaaagt gaaaacccag      840
tggccgaggt ctgcagatga gcctgggcta catggcgc   agacagtgca cggcgtgtgg      900
gaggagtggg ggtcctggag cctgtgctcc cgcagctgcg ggcgggggtc ccggagccgg      960
atgcggacct gcgtgccccc ccagcacggc ggcaaggcct gcgagggtcc tgagctgcag     1020
actaagctct gcagtatggc tgcctgcccg gtggaaggcc agtggttaga atggggtccc     1080
tggggcccat gctccacgtc ctgtgccaat gggacccaac agcgcagccg gaagtgcagc     1140
gtggcgggcc cagcctgggc cacatgcacg ggtgccctca ctgacacccg ggagtgcagc     1200
aacctcgagt gcccggccac tgatagcaag tgggggccat ggaatgcgtg gagcctgtgc     1260
tctaagacgt gtgacacagg ctggcagcgc cgcttccgca tgtgccaggc cacgggcacg     1320
cagggctacc cctgcgaggg caccggagag gaggtgaagc cttgtagtga aagaggtgt      1380 ccagccttcc atgagatgtg cagggatgag tacgtgatgc tgatgacgtg gaagaaggca     1440
gctgctggcg agatcatcta caacaagtgc cccccgaatg cctcagggtc tgccagccgc     1500
cgctgtctcc tcagtgccca aggcgtggcg tactgggggc tgcccagctt tgctcgctgc     1560
atctcccatg agtaccgcta cctgtatctg tcacttaggg agcacctggc caaggggcag     1620
cgcatgctgg caggcgaggg catgtcgcag gtggtgcgca gcctgcagga gctactggcc     1680
cggcgcacct actatagtgg ggacctgctc ttctctgtgg acattctgag gaatgtcact     1740 gacacctta  agagggccac ctacgtgccc tcggctgatg atgtgcagcg cttcttccag     1800
gtggtgagct tcatggtgga tgcggaaaac aaggagaagt gggacgatgc tcagcaggtg     1860
tcccctggct ctgtgcacct gctccgtgtc gtggaggact tcattcacct ggtgggcgat     1920
gctctcaagg ccttccagag ctctctgatt gtcacagata atctagtgat cagcattcag     1980
cgagagcccg tctcagctgt gtccagtgac atcacgttcc ccatgcgggg ccgccggggc     2040
atgaaggact gggtgcggca ctcagaggac cgcctcttcc tgcccaagga ggtgctcagc     2100
ctctcctccc cagggaagcc agccacatct ggggcagcag gcagccctgg caggggagg      2160 ggcccaggaa cggtgcctcc tggcccaggc cactcccacc agcgcctcct cccagcagac     2220
cctgatgagt cctcctactt tgtgatcggt gctgtactct accgcaccct tggcctcatc     2280
ctgccgcctc ccaggccccc gctggccgtc acatcccggg tgatgacagt gactgtgcgc     2340 cccctaccc  agcctccagc tgagcccctc atcactgtgg agctctccta catcatcaat     2400
gggaccacgg atccccattg cgccagctgg gactactcca gagcagatgc cagctcagga     2460
gactgggaca ctgaaaattg ccagaccctg gagacccagg cagctcacac ccgctgccag     2520
```

```
tgccagcacc tgtccacctt tgctgtacta gcccagccgc ccaaggacct gaccctggag    2580
ctggcgggct ccccctcggt ccccctggtg atcggctgtg cagtgtcgtg catggcgctg    2640
ctcaccctgc tcgccatcta tgccgccttt tggaggttca taaaatctga acgctccatc    2700
atcttgctga acttctgcct gtccatcttg gcatccaaca tcctgatcct cgtgggccag    2760
tcccgggtgc tgagcaaggg cgtgtgcacc atgacggctg ccttcctgca cttcttcttt    2820
ctctcctcct tttgctgggt gcttaccgag gcctggcagt cctacctggc tgtcattggg    2880
cggatgcgca cccgcctcgt tcgcaagcgc ttcctctgcc tgggctgggg tctgcctgcc    2940
ctggtggtgg ccgtgtctgt tggctttacc cgaacgaaag gatacggtac atccagctac    3000
tgctggctct ccctggaggg cggcctgctc tacgcctttg tgggccctgc agccgtcatt    3060
gtcctggtga acatgctcat cggaatcatc gtcttcaaca agctcatggc acgtgatggc    3120
atctccgaca atccaagaa gcagagggcc gggtcggagc ggtgccccctg gccagcctg     3180 ctcctcccct gctcagcgtg tggagcggtc cccagccccc tgctcagctc agcctcggcc    3240
aggaacgcca tggcctcact ctggagctcc tgcgtggtgc tgcccctgct ggcgctcacc    3300
tggatgtctg ccgtcctggc tatgacagac cgccgttccg tcctcttcca ggccctcttt    3360
gctgtcttca actccgcgca gggctttgtc atcactgctg tgcactgctt cctgcgccga    3420
gaggtccagg atgtggtgaa gtgccagatg ggggtgtgcc gggctgatga gagcgaagac    3480
tcccctgact cgtgtaagaa cgggcagctg cagatcctgt cagactttga aaaggatgtg    3540
gatctggctt gtcaaacagt gctgttcaag gaggtcaaca cttgcaaccc gtccaccatc    3600
acgggcacac tatcccgcct gtccctggat gaggatgagg agcccaagtc ctgcctcgtg    3660
ggccctgagg gcagcctcag cttctcacca ctgcctggga atatcctggt gcccatggca    3720
gcctcaccag ggctgggggga gcctccgccc cacaggagg ccaaccctgt ttacatgtgt    3780
ggggagggtg gcctgcggca gctggacctc acatggctgc ggcccactga gccaggctct    3840
gagggagact acatggtgct gccccggcgg actttgagcc tgcagcctgg cggtgggggt    3900
ggaggtggtg aggatgcccc cagggcccgg ccggagggga ccccccggcg agctgccaag    3960
acagtggccc acactgaagg ctaccccagc ttcctgtccg tggaccactc gggcctgggg    4020
ctgggccctg cctatggatc tctccagaat ccctatggaa tgaccttcca accgccaccg    4080
ccgacaccca gcgcccgcca agtgcccgag ccaggggagc gcagccggac catgcctcgc    4140
accgtgcccg gctctaccat gaagatgggc tccctggagc gaaagaaatt acggtattca    4200
gacctggact ttgagaaggt gatgcacacc cggaaacggc attcagaact ctaccacgag    4260
ctcaaccaga gttccacac tttcgaccgc taccgcagcc agtccacggc caagagggag    4320
aagcggtgga gtgtgtcctc gggtgggggca gccgagcgga gcgtgtgcac cgataagccc    4380
agccctgggg agcgccccag cttgtcccaa catcggcgcc atcagagctg gagcaccttc    4440 aaaatctatga cactgggctc gctgccccc aagccccgag aacggctgac tctgcaccgg    4500
gcagcagcct gggagcccac agaaccaccg gatggtgact ccagacaga ggtgtga      4557
```

<210> SEQ ID NO 2
<211> LENGTH: 1518
<212> TYPE: PRT
<213> ORGANISM: homo sapiens
<220> FEATURE:
<221> NAME/KEY: MISC_FEATURE
<223> OTHER INFORMATION: Protein encoded by the DNA having a
      nucleotide sequence of SEQ ID NO:1

```
<220> FEATURE:
<221> NAME/KEY: DOMAIN
<222> LOCATION: (297)..(350)
<223> OTHER INFORMATION: TSP-I domain
<220> FEATURE:
<221> NAME/KEY: DOMAIN
<222> LOCATION: (352)..(405)
<223> OTHER INFORMATION: TSP-I domain
<220> FEATURE:
<221> NAME/KEY: DOMAIN
<222> LOCATION: (408)..(461)
<223> OTHER INFORMATION: TSP-I domain
<220> FEATURE:
<221> NAME/KEY: TRANSMEM
<222> LOCATION: (870)..(890)
<223> OTHER INFORMATION: transmembrane domain
<220> FEATURE:
<221> NAME/KEY: TRANSMEM
<222> LOCATION: (899)..(919)
<223> OTHER INFORMATION: transmembrane domain
<220> FEATURE:
<221> NAME/KEY: TRANSMEM
<222> LOCATION: (928)..(948)
<223> OTHER INFORMATION: transmembrane domain
<220> FEATURE:
<221> NAME/KEY: TRANSMEM
<222> LOCATION: (970)..(990)
<223> OTHER INFORMATION: transmembrane domain
<220> FEATURE:
<221> NAME/KEY: TRANSMEM
<222> LOCATION: (1012)..(1032)
<223> OTHER INFORMATION: transmembrane domain
<220> FEATURE:
<221> NAME/KEY: TRANSMEM
<222> LOCATION: (1087)..(1107)
<223> OTHER INFORMATION: transmembrane domain
<220> FEATURE:
<221> NAME/KEY: TRANSMEM
<222> LOCATION: (1114)..(1134)
<223> OTHER INFORMATION: transmembrane domain

<400> SEQUENCE: 2

Met Thr Pro Ala Cys Pro Leu Leu Ser Val Ile Leu Ser Leu Arg
1               5                   10                  15

Leu Ala Thr Ala Phe Asp Pro Ala Pro Ser Ala Cys Ser Ala Leu Ala
            20                  25                  30

Ser Gly Val Leu Tyr Gly Ala Phe Ser Leu Gln Asp Leu Phe Pro Thr
        35                  40                  45

Ile Ala Ser Gly Cys Ser Trp Thr Leu Glu Asn Pro Asp Pro Thr Lys
    50                  55                  60

Tyr Ser Leu Tyr Leu Arg Phe Asn Arg Gln Glu Gln Val Cys Ala His
65                  70                  75                  80

Phe Ala Pro Arg Leu Leu Pro Leu Asp His Tyr Leu Val Asn Phe Thr
                85                  90                  95

Cys Leu Arg Pro Ser Pro Glu Glu Ala Val Ala Gln Ala Glu Ser Glu
            100                 105                 110

Val Gly Arg Pro Glu Glu Glu Ala Glu Ala Ala Gly Leu Glu
        115                 120                 125

Leu Cys Ser Gly Ser Gly Pro Phe Thr Phe Leu His Phe Asp Lys Asn
    130                 135                 140

Phe Val Gln Leu Cys Leu Ser Ala Glu Pro Ser Glu Ala Pro Arg Leu
145                 150                 155                 160

Leu Ala Pro Ala Ala Leu Ala Phe Arg Phe Val Glu Val Leu Leu Ile
                165                 170                 175

Asn Asn Asn Asn Ser Ser Gln Phe Thr Cys Gly Val Leu Cys Arg Trp
            180                 185                 190
```

```
Ser Glu Glu Cys Gly Arg Ala Ala Gly Arg Ala Cys Gly Phe Ala Gln
            195                 200                 205

Pro Gly Cys Ser Cys Pro Gly Glu Ala Gly Ala Gly Ser Thr Thr Thr
        210                 215                 220

Thr Ser Pro Gly Pro Pro Ala Ala His Thr Leu Ser Asn Ala Leu Val
225                 230                 235                 240

Pro Gly Gly Pro Ala Pro Pro Ala Glu Ala Asp Leu His Ser Gly Ser
                245                 250                 255

Ser Asn Asp Leu Phe Thr Thr Glu Met Arg Tyr Gly Glu Glu Pro Glu
            260                 265                 270

Glu Glu Pro Lys Val Lys Thr Gln Trp Pro Arg Ser Ala Asp Glu Pro
        275                 280                 285

Gly Leu Tyr Met Ala Gln Thr Val His Gly Val Trp Glu Glu Trp Gly
            290                 295                 300

Ser Trp Ser Leu Cys Ser Arg Ser Cys Gly Arg Gly Ser Arg Ser Arg
305                 310                 315                 320

Met Arg Thr Cys Val Pro Pro Gln His Gly Gly Lys Ala Cys Glu Gly
                325                 330                 335

Pro Glu Leu Gln Thr Lys Leu Cys Ser Met Ala Ala Cys Pro Val Glu
            340                 345                 350

Gly Gln Trp Leu Glu Trp Gly Pro Trp Gly Pro Cys Ser Thr Ser Cys
        355                 360                 365

Ala Asn Gly Thr Gln Gln Arg Ser Arg Lys Cys Ser Val Ala Gly Pro
            370                 375                 380

Ala Trp Ala Thr Cys Thr Gly Ala Leu Thr Asp Thr Arg Glu Cys Ser
385                 390                 395                 400

Asn Leu Glu Cys Pro Ala Thr Asp Ser Lys Trp Gly Pro Trp Asn Ala
                405                 410                 415

Trp Ser Leu Cys Ser Lys Thr Cys Asp Thr Gly Trp Gln Arg Arg Phe
            420                 425                 430

Arg Met Cys Gln Ala Thr Gly Thr Gln Gly Tyr Pro Cys Glu Gly Thr
        435                 440                 445

Gly Glu Glu Val Lys Pro Cys Ser Glu Lys Arg Cys Pro Ala Phe His
    450                 455                 460

Glu Met Cys Arg Asp Glu Tyr Val Met Leu Met Thr Trp Lys Lys Ala
465                 470                 475                 480

Ala Ala Gly Glu Ile Ile Tyr Asn Lys Cys Pro Pro Asn Ala Ser Gly
                485                 490                 495

Ser Ala Ser Arg Arg Cys Leu Leu Ser Ala Gln Gly Val Ala Tyr Trp
            500                 505                 510

Gly Leu Pro Ser Phe Ala Arg Cys Ile Ser His Glu Tyr Arg Tyr Leu
        515                 520                 525

Tyr Leu Ser Leu Arg Glu His Leu Ala Lys Gly Gln Arg Met Leu Ala
        530                 535                 540

Gly Glu Gly Met Ser Gln Val Val Arg Ser Leu Gln Glu Leu Leu Ala
545                 550                 555                 560

Arg Arg Thr Tyr Tyr Ser Gly Asp Leu Leu Phe Ser Val Asp Ile Leu
            565                 570                 575

Arg Asn Val Thr Asp Thr Phe Lys Arg Ala Thr Tyr Val Pro Ser Ala
            580                 585                 590

Asp Asp Val Gln Arg Phe Phe Gln Val Val Ser Phe Met Val Asp Ala
        595                 600                 605

Glu Asn Lys Glu Lys Trp Asp Asp Ala Gln Gln Val Ser Pro Gly Ser
```

-continued

```
            610                 615                 620
Val His Leu Leu Arg Val Val Glu Asp Phe Ile His Leu Val Gly Asp
625                 630                 635                 640

Ala Leu Lys Ala Phe Gln Ser Ser Leu Ile Val Thr Asp Asn Leu Val
                645                 650                 655

Ile Ser Ile Gln Arg Glu Pro Val Ser Ala Val Ser Ser Asp Ile Thr
                660                 665                 670

Phe Pro Met Arg Gly Arg Arg Gly Met Lys Asp Trp Val Arg His Ser
                675                 680                 685

Glu Asp Arg Leu Phe Leu Pro Lys Glu Val Leu Ser Leu Ser Ser Pro
690                 695                 700

Gly Lys Pro Ala Thr Ser Gly Ala Ala Gly Ser Pro Gly Arg Gly Arg
705                 710                 715                 720

Gly Pro Gly Thr Val Pro Pro Gly Pro Gly His Ser His Gln Arg Leu
                725                 730                 735

Leu Pro Ala Asp Pro Asp Glu Ser Ser Tyr Phe Val Ile Gly Ala Val
                740                 745                 750

Leu Tyr Arg Thr Leu Gly Leu Ile Leu Pro Pro Arg Pro Pro Leu
                755                 760                 765

Ala Val Thr Ser Arg Val Met Thr Val Thr Val Arg Pro Pro Thr Gln
                770                 775                 780

Pro Pro Ala Glu Pro Leu Ile Thr Val Glu Leu Ser Tyr Ile Ile Asn
785                 790                 795                 800

Gly Thr Thr Asp Pro His Cys Ala Ser Trp Asp Tyr Ser Arg Ala Asp
                805                 810                 815

Ala Ser Ser Gly Asp Trp Asp Thr Glu Asn Cys Gln Thr Leu Glu Thr
                820                 825                 830

Gln Ala Ala His Thr Arg Cys Gln Cys Gln His Leu Ser Thr Phe Ala
                835                 840                 845

Val Leu Ala Gln Pro Pro Lys Asp Leu Thr Leu Glu Leu Ala Gly Ser
850                 855                 860

Pro Ser Val Pro Leu Val Ile Gly Cys Ala Val Ser Cys Met Ala Leu
865                 870                 875                 880

Leu Thr Leu Leu Ala Ile Tyr Ala Ala Phe Trp Arg Phe Ile Lys Ser
                885                 890                 895

Glu Arg Ser Ile Ile Leu Leu Asn Phe Cys Leu Ser Ile Leu Ala Ser
                900                 905                 910

Asn Ile Leu Ile Leu Val Gly Gln Ser Arg Val Leu Ser Lys Gly Val
                915                 920                 925

Cys Thr Met Thr Ala Ala Phe Leu His Phe Phe Phe Leu Ser Ser Phe
930                 935                 940

Cys Trp Val Leu Thr Glu Ala Trp Gln Ser Tyr Leu Ala Val Ile Gly
945                 950                 955                 960

Arg Met Arg Thr Arg Leu Val Arg Lys Arg Phe Leu Cys Leu Gly Trp
                965                 970                 975

Gly Leu Pro Ala Leu Val Val Ala Val Ser Val Gly Phe Thr Arg Thr
                980                 985                 990

Lys Gly Tyr Gly Thr Ser Ser Tyr Cys Trp Leu Ser Leu Glu Gly Gly
                995                 1000                1005

Leu Leu Tyr Ala Phe Val Gly Pro Ala Ala Val Ile Val Leu Val
                1010                1015                1020

Asn Met Leu Ile Gly Ile Ile Val Phe Asn Lys Leu Met Ala Arg
                1025                1030                1035
```

-continued

```
Asp Gly Ile Ser Asp Lys Ser Lys Lys Gln Arg Ala Gly Ser Glu
    1040                1045                1050

Arg Cys Pro Trp Ala Ser Leu Leu Leu Pro Cys Ser Ala Cys Gly
    1055                1060                1065

Ala Val Pro Ser Pro Leu Leu Ser Ser Ala Ser Ala Arg Asn Ala
    1070                1075                1080

Met Ala Ser Leu Trp Ser Ser Cys Val Val Leu Pro Leu Leu Ala
    1085                1090                1095

Leu Thr Trp Met Ser Ala Val Leu Ala Met Thr Asp Arg Arg Ser
    1100                1105                1110

Val Leu Phe Gln Ala Leu Phe Ala Val Phe Asn Ser Ala Gln Gly
    1115                1120                1125

Phe Val Ile Thr Ala Val His Cys Phe Leu Arg Arg Glu Val Gln
    1130                1135                1140

Asp Val Val Lys Cys Gln Met Gly Val Cys Arg Ala Asp Glu Ser
    1145                1150                1155

Glu Asp Ser Pro Asp Ser Cys Lys Asn Gly Gln Leu Gln Ile Leu
    1160                1165                1170

Ser Asp Phe Glu Lys Asp Val Asp Leu Ala Cys Gln Thr Val Leu
    1175                1180                1185

Phe Lys Glu Val Asn Thr Cys Asn Pro Ser Thr Ile Thr Gly Thr
    1190                1195                1200

Leu Ser Arg Leu Ser Leu Asp Glu Asp Glu Pro Lys Ser Cys
    1205                1210                1215

Leu Val Gly Pro Glu Gly Ser Leu Ser Phe Ser Pro Leu Pro Gly
    1220                1225                1230

Asn Ile Leu Val Pro Met Ala Ala Ser Pro Gly Leu Gly Glu Pro
    1235                1240                1245

Pro Pro Pro Gln Glu Ala Asn Pro Val Tyr Met Cys Gly Glu Gly
    1250                1255                1260

Gly Leu Arg Gln Leu Asp Leu Thr Trp Leu Arg Pro Thr Glu Pro
    1265                1270                1275

Gly Ser Glu Gly Asp Tyr Met Val Leu Pro Arg Arg Thr Leu Ser
    1280                1285                1290

Leu Gln Pro Gly Gly Gly Gly Gly Gly Glu Asp Ala Pro Arg
    1295                1300                1305

Ala Arg Pro Glu Gly Thr Pro Arg Arg Ala Ala Lys Thr Val Ala
    1310                1315                1320

His Thr Glu Gly Tyr Pro Ser Phe Leu Ser Val Asp His Ser Gly
    1325                1330                1335

Leu Gly Leu Gly Pro Ala Tyr Gly Ser Leu Gln Asn Pro Tyr Gly
    1340                1345                1350

Met Thr Phe Gln Pro Pro Pro Thr Pro Ser Ala Arg Gln Val
    1355                1360                1365

Pro Glu Pro Gly Glu Arg Ser Arg Thr Met Pro Arg Thr Val Pro
    1370                1375                1380

Gly Ser Thr Met Lys Met Gly Ser Leu Glu Arg Lys Lys Leu Arg
    1385                1390                1395

Tyr Ser Asp Leu Asp Phe Glu Lys Val Met His Thr Arg Lys Arg
    1400                1405                1410

His Ser Glu Leu Tyr His Glu Leu Asn Gln Lys Phe His Thr Phe
    1415                1420                1425
```

```
Asp Arg Tyr Arg Ser Gln Ser Thr Ala Lys Arg Glu Lys Arg Trp
    1430                1435                1440

Ser Val Ser Ser Gly Gly Ala Ala Glu Arg Ser Val Cys Thr Asp
    1445                1450                1455

Lys Pro Ser Pro Gly Glu Arg Pro Ser Leu Ser Gln His Arg Arg
    1460                1465                1470

His Gln Ser Trp Ser Thr Phe Lys Ser Met Thr Leu Gly Ser Leu
    1475                1480                1485

Pro Pro Lys Pro Arg Glu Arg Leu Thr Leu His Arg Ala Ala Ala
    1490                1495                1500

Trp Glu Pro Thr Glu Pro Pro Asp Gly Asp Phe Gln Thr Glu Val
    1505                1510                1515

<210> SEQ ID NO 3
<211> LENGTH: 4
<212> TYPE: PRT
<213> ORGANISM: homo sapiens
<220> FEATURE:
<221> NAME/KEY: MISC_FEATURE
<222> LOCATION: (1)..(4)
<223> OTHER INFORMATION: Partial amino acid sequence that exists in
      each C -terminal region of the peptide having the amino acid
      sequence of SEQ ID NO:2, human BAI1 and human BAI2,

<400> SEQUENCE: 3

Gln Thr Glu Val
1

<210> SEQ ID NO 4
<211> LENGTH: 28
<212> TYPE: DNA
<213> ORGANISM: Artificial
<220> FEATURE:
<223> OTHER INFORMATION: Designed oligonucleotide for using as a primer

<400> SEQUENCE: 4
ggggacaagt ttgtacaaaa aagcaggc                                         28

<210> SEQ ID NO 5
<211> LENGTH: 28
<212> TYPE: DNA
<213> ORGANISM: Artificial
<220> FEATURE:
<223> OTHER INFORMATION: Designed oligonucleotide for using as a primer

<400> SEQUENCE: 5
ggggaccact ttgtacaaga aagctggg                                         28

<210> SEQ ID NO 6
<211> LENGTH: 31
<212> TYPE: DNA
<213> ORGANISM: Artificial
<220> FEATURE:
<223> OTHER INFORMATION: Designed oligonucleotide for using as a primer

<400> SEQUENCE: 6
aaaaagcagg ctggatgacc ccagcctgtc c                                     31

<210> SEQ ID NO 7
<211> LENGTH: 32
<212> TYPE: DNA
<213> ORGANISM: Artificial
<220> FEATURE:
<223> OTHER INFORMATION: Designed oligonucleotide for using as a primer
```

<400> SEQUENCE: 7
agaaagctgg gtgcactcac acctctgtct gg                                      32

<210> SEQ ID NO 8
<211> LENGTH: 36
<212> TYPE: DNA
<213> ORGANISM: Artificial
<220> FEATURE:
<223> OTHER INFORMATION: Designed oligonucleotide for using as a primer

<400> SEQUENCE: 8
tacaaaaaag caggcttcga ccccgccccc agtgcc                                  36

<210> SEQ ID NO 9
<211> LENGTH: 33
<212> TYPE: DNA
<213> ORGANISM: Artificial
<220> FEATURE:
<223> OTHER INFORMATION: Designed oligonucleotide for using as a primer

<400> SEQUENCE: 9
ggggtcgaag cctgcttttt tgtacaaagt tgg                                     33

<210> SEQ ID NO 10
<211> LENGTH: 25
<212> TYPE: DNA
<213> ORGANISM: Artificial
<220> FEATURE:
<223> OTHER INFORMATION: Designed oligonucleotide for using as a primer

<400> SEQUENCE: 10
tcgcgttaac gctagcatgg atctc                                              25

<210> SEQ ID NO 11
<211> LENGTH: 24
<212> TYPE: DNA
<213> ORGANISM: Artificial
<220> FEATURE:
<223> OTHER INFORMATION: Designed oligonucleotide for using as a primer

<400> SEQUENCE: 11
gtaacatcag agattttgag acac                                               24

<210> SEQ ID NO 12
<211> LENGTH: 125
<212> TYPE: DNA
<213> ORGANISM: Artificial
<220> FEATURE:
<223> OTHER INFORMATION: Synthesized oligonucleotide

<400> SEQUENCE: 12
gggggaattc accatggcct taccagtgac cgccttgctc ctgccgctgg ccttgctgct        60
ccacgccgcc aggccggatt acgcttctta cccatacgat gttccagatt acgctgtcga       120
cgggg                                                                   125

<210> SEQ ID NO 13
<211> LENGTH: 125
<212> TYPE: DNA
<213> ORGANISM: Artificial
<220> FEATURE:
<223> OTHER INFORMATION: Synthesized oligonucleotide

<400> SEQUENCE: 13
ccccgtcgac agcgtaatct ggaacatcgt atgggtaaga agcgtaatcc ggcctggcgg        60

```
cgtggagcag caaggccagc ggcaggagca aggcggtcac tggtaaggcc atggtgaatt    120
ccccc                                                                125

<210> SEQ ID NO 14
<211> LENGTH: 8
<212> TYPE: PRT
<213> ORGANISM: Homo sapiens
<220> FEATURE:
<221> NAME/KEY: MISC_FEATURE
<223> OTHER INFORMATION: CCK-8S
<220> FEATURE:
<221> NAME/KEY: MOD_RES
<222> LOCATION: (2)..(2)
<223> OTHER INFORMATION: SULFATATION

<400> SEQUENCE: 14

Asp Tyr Met Gly Trp Met Asp Phe
1               5

<210> SEQ ID NO 15
<211> LENGTH: 4389
<212> TYPE: DNA
<213> ORGANISM: homo sapiens
<220> FEATURE:
<221> NAME/KEY: misc_feature
<223> OTHER INFORMATION: A splice variant of the DNA having the
      nucleotide sequence of SEQ ID NO:1

<400> SEQUENCE: 15
atgaccccag cctgtcccct cttactgtct gtgattctgt ccctgcgcct ggccaccgcc     60
ttcgaccccg cccccagtgc ctgctctgcc ctggcctcgg gtgtgctcta cggggccttc    120
tcgctgcagg acctctttcc taccatcgcc tcgggctgct cctggaccct ggagaaccct    180
gaccccacca gtactccct ctacctgcgc ttcaaccgcc aggagcaggt gtgcgcacac    240
tttgcccccc gcctgctgcc cctggaccac tacctggtca actttacctg cctgcggcct    300
agccccgagg aggcggtggc ccaggcggag tcagaggtgg ggcggccaga agaggaggag    360
gcagaggcgc agcggggtt ggagctgtgc agcggctcag gccccttttac cttcctgcac    420 ttcgacaaga acttcgtgca gctgtgcctg tcggctgagc cctccgaggc cccgcgcctg    480
ctggcgcccg ctgccctagc cttccgctttt gtcgaggtct tgctcatcaa caacaacaac    540
tctagccaat tcacctgtgg tgtgctctgc cgctggagtg aggagtgtgg ccgcgctgcc    600
ggcagggcct gcggctttgc tcagccaggc tgcagctgcc ctggagaggc ggggccggc    660 tccaccacca ccacatctcc aggccctcct gctgcccaca ccctgtccaa tgccctggtg    720
cccgggggcc cagcccccacc tgctgaggcc gatttgcact cggggagcag caatgatctg    780
ttcacaaccg agatgagata tggtgaggag ccggaagagg aaccgaaagt gaaaacccag    840
tggccgaggt ctgcagatga gcctgggcta tacatggcgc agacagtgga aggccagtgg    900
ttagaatggg gtccctgggg cccatgctcc acgtcctgtg ccaatgggac ccaacagcgc    960
agccggaagt gcagcgtggc gggcccagcc tgggccacat gcacgggtgc cctcactgac   1020
acccgggagt gcagcaacct cgagtgcccg gccactgata gcaagtgggg gccatggaat   1080
gcgtggagcc tgtgctctaa gacgtgtgac acaggctggc agcgcccgctt ccgcatgtgc   1140 caggccacgg gcacgcaggg ctaccccttgc gagggcaccg agaggaggt gaagccttgt   1200 agtgagaaga ggtgtccagc cttccatgag atgtgcaggg atgagtacgt gatgctgatg   1260
acgtggaaga aggcagctgc tggcgagatc atctacaaca gtgccccccc gaatgcctca   1320
```

```
gggtctgcca gccgccgctg tctcctcagt gcccaaggcg tggcgtactg ggggctgccc    1380
agctttgctc gctgcatctc ccatgagtac cgctacctgt atctgtcact tagggagcac    1440
ctggccaagg ggcagcgcat gctggcaggc gagggcatgt cgcaggtggt gcgcagcctg    1500
caggagctac tggcccggcg cacctactat agtggggacc tgctcttctc tgtggacatt    1560
ctgaggaatg tcactgacac ctttaagagg gccacctacg tgccctcggc tgatgatgtg    1620
cagcgcttct tccaggtggt gagcttcatg gtggatgcgg aaaacaagga gaagtgggac    1680
gatgctcagc aggtgtcccc tggctctgtg cacctgctcc gtgtcgtgga ggacttcatt    1740
cacctggtgg gcgatgctct caaggccttc cagagctctc tgattgtcac agataatcta    1800
gtgatcagca ttcagcgaga gcccgtctca gctgtgtcca gtgacatcac gttccccatg    1860
cggggccgcc ggggcatgaa ggactgggtg cggcactcag aggaccgcct cttcctgccc    1920
aaggaggtgc tcagcctctc ctccccaggg aagccagcca catctggggc agcaggcagc    1980
cctggcaggg gaggggccc aggaacggtg cctcctggcc caggccactc ccaccagcgc    2040
ctcctcccag cagaccctga tgagtcctcc tactttgtga tcggtgctgt actctaccgc    2100
acccttggcc tcatcctgcc gcctcccagg ccccgctgg ccgtcacatc ccgggtgatg    2160
acagtgactg tgcgcccccc tacccagcct ccagctgagc ccctcatcac tgtggagctc    2220
tcctacatca tcaatgggac cacggatccc cattgcgcca gctgggacta ctccagagca    2280
gatgccagct caggagactg ggacactgaa aattgccaga ccctggagac ccaggcagct    2340
cacacccgct gccagtgcca gcacctgtcc acctttgctg tactagccca gccgcccaag    2400
gacctgaccc tggagctggc gggctccccc tcggtccccc tggtgatcgg ctgtgcagtg    2460
tcgtgcatgg cgctgctcac cctgctcgcc atctatgccg cctttttggag gttcataaaa    2520
tctgaacgct ccatcatctt gctgaacttc tgcctgtcca tcttggcatc caacatcctg    2580
atcctcgtgg gccagtcccg ggtgctgagc aagggcgtgt gcaccatgac ggctgccttc    2640
ctgcacttct tctttctctc ctccttttgc tgggtgctta ccgaggcctg gcagtcctac    2700
ctggctgtca ttgggcggat gcgcacccgc ctcgttcgca gcgcttcct ctgcctgggc    2760
tggggtctgc ctgccctggt ggtggccgtg tctgttggct ttacccgaac gaaaggatac    2820
ggtacatcca gctactgctg gctctccctg gagggcggcc tgctctacgc ctttgtgggc    2880
cctgcagccg tcattgtcct ggtgaacatg ctcatcggaa tcatcgtctt caacaagctc    2940
atggcacgtg atggcatctc cgacaaatcc aagaagcaga gggccgggtc ggagcggtgc    3000
ccctgggcca gcctgctcct cccctgctca gcgtgtggag cggtccccag cccctgctc    3060
agctcagcct cggccaggaa cgccatggcc tcactctgga gctcctgcgt ggtgctgccc    3120
ctgctggcgc tcacctggat gtctgccgtc ctggctatga cagaccgccg ttccgtcctc    3180
ttccaggccc tctttgctgt cttcaactcc gcgcagggct tgtcatcac tgctgtgcac    3240
tgcttcctgc gccgagaggt ccaggatgtg gtgaagtgcc agatggggt gtgccgggct    3300
gatgagagcg aagactcccc tgactcgtgt aagaacgggc agctgcagat cctgtcagac    3360
tttgaaaagg atgtggatct ggcttgtcaa acagtgctgt tcaaggaggt caacacttgc    3420
aacccgtcca ccatcacggg cacactatcc cgcctgtccc tggatgagga tgaggagccc    3480
aagtcctgcc tcgtgggccc tgagggcagc ctcagcttct caccactgcc tgggaatatc    3540
ctggtgccca tggcagcctc accagggctg ggggagcctc cgcccccaca ggaggccaac    3600
cctgtttaca tgtgtgggga gggtggcctg cggcagctgg acctcacatg gctgcggccc    3660
actgagccag gctctgaggg agactacatg gtgctgcccc ggcggacttt gagcctgcag    3720
```

```
cctggcggtg ggggtggagg tggtgaggat gcccccaggg cccggccgga ggggacccc    3780 cggcgagctg ccaagacagt ggcccacact gaaggctacc ccagcttcct gtccgtggac    3840
cactcgggcc tggggctggg ccctgcctat ggatctctcc agaatcccta tggaatgacc    3900
ttccaaccgc caccgccgac acccagcgcc cgccaagtgc ccgagccagg ggagcgcagc    3960
cggaccatgc ctcgcaccgt gcccggctct accatgaaga tgggctccct ggagcgaaag    4020
aaattacggt attcagacct ggactttgag aaggtgatgc acacccggaa acggcattca    4080
gaactctacc acgagctcaa ccagaagttc cacactttcg accgctaccg cagccagtcc    4140
acggccaaga gggagaagcg gtggagtgtg tcctcgggtg gggcagccga gcggagcgtg    4200
tgcaccgata agcccagccc tggggagcgc cccagcttgt cccaacatcg gcgccatcag    4260
agctggagca ccttcaaatc tatgacactg ggctcgctgc ccccaagcc ccgagaacgg     4320 ctgactctgc accgggcagc agcctgggag cccacagaac caccggatgg tgacttccag    4380
acagaggtg                                                             4389
```

```
<210> SEQ ID NO 16
<211> LENGTH: 1463
<212> TYPE: PRT
<213> ORGANISM: homo sapiens
<220> FEATURE:
<221> NAME/KEY: misc_feature
<223> OTHER INFORMATION: Protein encoded by the DNA having a
      nucleotide sequence of SEQ ID NO:15
<220> FEATURE:
<221> NAME/KEY: DOMAIN
<222> LOCATION: (297)..(350)
<223> OTHER INFORMATION: TSP-I domain
<220> FEATURE:
<221> NAME/KEY: DOMAIN
<222> LOCATION: (353)..(406)
<223> OTHER INFORMATION: TSP-I domain
<220> FEATURE:
<221> NAME/KEY: TRANSMEM
<222> LOCATION: (815)..(835)
<223> OTHER INFORMATION: transmembrane domain
<220> FEATURE:
<221> NAME/KEY: TRANSMEM
<222> LOCATION: (844)..(864)
<223> OTHER INFORMATION: transmembrane domain
<220> FEATURE:
<221> NAME/KEY: TRANSMEM
<222> LOCATION: (873)..(893)
<223> OTHER INFORMATION: transmembrane domain
<220> FEATURE:
<221> NAME/KEY: TRANSMEM
<222> LOCATION: (915)..(935)
<223> OTHER INFORMATION: transmembrane domain
<220> FEATURE:
<221> NAME/KEY: TRANSMEM
<222> LOCATION: (957)..(977)
<223> OTHER INFORMATION: transmembrane domain
<220> FEATURE:
<221> NAME/KEY: TRANSMEM
<222> LOCATION: (1032)..(1052)
<223> OTHER INFORMATION: transmembrane domain
<220> FEATURE:
<221> NAME/KEY: TRANSMEM
<222> LOCATION: (1059)..(1079)
<223> OTHER INFORMATION: transmembrane domain

<400> SEQUENCE: 16

Met Thr Pro Ala Cys Pro Leu Leu Leu Ser Val Ile Leu Ser Leu Arg
1               5                   10                  15

Leu Ala Thr Ala Phe Asp Pro Ala Pro Ser Ala Cys Ser Ala Leu Ala
            20                  25                  30
```

```
Ser Gly Val Leu Tyr Gly Ala Phe Ser Leu Gln Asp Leu Phe Pro Thr
         35                  40                  45

Ile Ala Ser Gly Cys Ser Trp Thr Leu Glu Asn Pro Asp Pro Thr Lys
 50                  55                  60

Tyr Ser Leu Tyr Leu Arg Phe Asn Arg Gln Glu Gln Val Cys Ala His
 65                  70                  75                  80

Phe Ala Pro Arg Leu Leu Pro Leu Asp His Tyr Leu Val Asn Phe Thr
                 85                  90                  95

Cys Leu Arg Pro Ser Pro Glu Glu Ala Val Ala Gln Ala Glu Ser Glu
                100                 105                 110

Val Gly Arg Pro Glu Glu Glu Ala Glu Ala Ala Gly Leu Glu
                115                 120                 125

Leu Cys Ser Gly Ser Gly Pro Phe Thr Phe Leu His Phe Asp Lys Asn
130                 135                 140

Phe Val Gln Leu Cys Leu Ser Ala Glu Pro Ser Glu Ala Pro Arg Leu
145                 150                 155                 160

Leu Ala Pro Ala Ala Leu Ala Phe Arg Phe Val Glu Val Leu Leu Ile
                165                 170                 175

Asn Asn Asn Ser Ser Gln Phe Thr Cys Gly Val Leu Cys Arg Trp
                180                 185                 190

Ser Glu Glu Cys Gly Arg Ala Ala Gly Arg Ala Cys Gly Phe Ala Gln
                195                 200                 205

Pro Gly Cys Ser Cys Pro Gly Glu Ala Gly Ala Gly Ser Thr Thr Thr
                210                 215                 220

Thr Ser Pro Gly Pro Pro Ala Ala His Thr Leu Ser Asn Ala Leu Val
225                 230                 235                 240

Pro Gly Gly Pro Ala Pro Pro Ala Glu Ala Asp Leu His Ser Gly Ser
                245                 250                 255

Ser Asn Asp Leu Phe Thr Thr Glu Met Arg Tyr Gly Glu Glu Pro Glu
                260                 265                 270

Glu Glu Pro Lys Val Lys Thr Gln Trp Pro Arg Ser Ala Asp Glu Pro
                275                 280                 285

Gly Leu Tyr Met Ala Gln Thr Val Glu Gly Gln Trp Leu Glu Trp Gly
                290                 295                 300

Pro Trp Gly Pro Cys Ser Thr Ser Cys Ala Asn Gly Thr Gln Gln Arg
305                 310                 315                 320

Ser Arg Lys Cys Ser Val Ala Gly Pro Ala Trp Ala Thr Cys Thr Gly
                325                 330                 335

Ala Leu Thr Asp Thr Arg Glu Cys Ser Asn Leu Glu Cys Pro Ala Thr
                340                 345                 350

Asp Ser Lys Trp Gly Pro Trp Asn Ala Trp Ser Leu Cys Ser Lys Thr
                355                 360                 365

Cys Asp Thr Gly Trp Gln Arg Arg Phe Arg Met Cys Gln Ala Thr Gly
                370                 375                 380

Thr Gln Gly Tyr Pro Cys Glu Gly Thr Gly Glu Glu Val Lys Pro Cys
385                 390                 395                 400

Ser Glu Lys Arg Cys Pro Ala Phe His Glu Met Cys Arg Asp Glu Tyr
                405                 410                 415

Val Met Leu Met Thr Trp Lys Lys Ala Ala Gly Glu Ile Ile Tyr
                420                 425                 430

Asn Lys Cys Pro Pro Asn Ala Ser Gly Ser Ala Ser Arg Arg Cys Leu
                435                 440                 445

Leu Ser Ala Gln Gly Val Ala Tyr Trp Gly Leu Pro Ser Phe Ala Arg
```

-continued

```
            450                 455                 460
Cys Ile Ser His Glu Tyr Arg Tyr Leu Tyr Leu Ser Leu Arg Glu His
465                 470                 475                 480

Leu Ala Lys Gly Gln Arg Met Leu Ala Gly Glu Gly Met Ser Gln Val
                485                 490                 495

Val Arg Ser Leu Gln Glu Leu Leu Ala Arg Arg Thr Tyr Tyr Ser Gly
                500                 505                 510

Asp Leu Leu Phe Ser Val Asp Ile Leu Arg Asn Val Thr Asp Thr Phe
                515                 520                 525

Lys Arg Ala Thr Tyr Val Pro Ser Ala Asp Val Gln Arg Phe Phe
530                 535                 540

Gln Val Val Ser Phe Met Val Asp Ala Glu Asn Lys Glu Lys Trp Asp
545                 550                 555                 560

Asp Ala Gln Gln Val Ser Pro Gly Ser Val His Leu Leu Arg Val Val
                565                 570                 575

Glu Asp Phe Ile His Leu Val Gly Asp Ala Leu Lys Ala Phe Gln Ser
                580                 585                 590

Ser Leu Ile Val Thr Asp Asn Leu Val Ile Ser Ile Gln Arg Glu Pro
                595                 600                 605

Val Ser Ala Val Ser Ser Asp Ile Thr Phe Pro Met Arg Gly Arg Arg
                610                 615                 620

Gly Met Lys Asp Trp Val Arg His Ser Glu Asp Arg Leu Phe Leu Pro
625                 630                 635                 640

Lys Glu Val Leu Ser Leu Ser Pro Gly Lys Pro Ala Thr Ser Gly
                645                 650                 655

Ala Ala Gly Ser Pro Gly Arg Gly Arg Gly Pro Gly Thr Val Pro Pro
                660                 665                 670

Gly Pro Gly His Ser His Gln Arg Leu Leu Pro Ala Asp Pro Asp Glu
                675                 680                 685

Ser Ser Tyr Phe Val Ile Gly Ala Val Leu Tyr Arg Thr Leu Gly Leu
                690                 695                 700

Ile Leu Pro Pro Pro Arg Pro Pro Leu Ala Val Thr Ser Arg Val Met
705                 710                 715                 720

Thr Val Thr Val Arg Pro Pro Thr Gln Pro Pro Ala Glu Pro Leu Ile
                725                 730                 735

Thr Val Glu Leu Ser Tyr Ile Ile Asn Gly Thr Thr Asp Pro His Cys
                740                 745                 750

Ala Ser Trp Asp Tyr Ser Arg Ala Asp Ala Ser Ser Gly Asp Trp Asp
                755                 760                 765

Thr Glu Asn Cys Gln Thr Leu Glu Thr Gln Ala Ala His Thr Arg Cys
770                 775                 780

Gln Cys Gln His Leu Ser Thr Phe Ala Val Leu Ala Gln Pro Pro Lys
785                 790                 795                 800

Asp Leu Thr Leu Glu Leu Ala Gly Ser Pro Ser Val Pro Leu Val Ile
                805                 810                 815

Gly Cys Ala Val Ser Cys Met Ala Leu Leu Thr Leu Leu Ala Ile Tyr
                820                 825                 830

Ala Ala Phe Trp Arg Phe Ile Lys Ser Glu Arg Ser Ile Ile Leu Leu
                835                 840                 845

Asn Phe Cys Leu Ser Ile Leu Ala Ser Asn Ile Leu Ile Leu Val Gly
850                 855                 860

Gln Ser Arg Val Leu Ser Lys Gly Val Cys Thr Met Thr Ala Ala Phe
865                 870                 875                 880
```

-continued

```
Leu His Phe Phe Phe Leu Ser Ser Phe Cys Trp Val Leu Thr Glu Ala
            885                 890                 895

Trp Gln Ser Tyr Leu Ala Val Ile Gly Arg Met Arg Thr Arg Leu Val
            900                 905                 910

Arg Lys Arg Phe Leu Cys Leu Gly Trp Gly Leu Pro Ala Leu Val Val
            915                 920                 925

Ala Val Ser Val Gly Phe Thr Arg Thr Lys Gly Tyr Gly Thr Ser Ser
            930                 935                 940

Tyr Cys Trp Leu Ser Leu Glu Gly Gly Leu Leu Tyr Ala Phe Val Gly
945                 950                 955                 960

Pro Ala Ala Val Ile Val Leu Val Asn Met Leu Ile Gly Ile Ile Val
            965                 970                 975

Phe Asn Lys Leu Met Ala Arg Asp Gly Ile Ser Asp Lys Ser Lys Lys
            980                 985                 990

Gln Arg Ala Gly Ser Glu Arg Cys Pro Trp Ala Ser Leu Leu Leu Pro
            995                 1000                1005

Cys Ser Ala Cys Gly Ala Val Pro Ser Pro Leu Leu Ser Ser Ala
            1010                1015                1020

Ser Ala Arg Asn Ala Met Ala Ser Leu Trp Ser Ser Cys Val Val
            1025                1030                1035

Leu Pro Leu Leu Ala Leu Thr Trp Met Ser Ala Val Leu Ala Met
            1040                1045                1050

Thr Asp Arg Arg Ser Val Leu Phe Gln Ala Leu Phe Ala Val Phe
            1055                1060                1065

Asn Ser Ala Gln Gly Phe Val Ile Thr Ala Val His Cys Phe Leu
            1070                1075                1080

Arg Arg Glu Val Gln Asp Val Lys Cys Gln Met Gly Val Cys
            1085                1090                1095

Arg Ala Asp Glu Ser Glu Asp Ser Pro Asp Ser Cys Lys Asn Gly
            1100                1105                1110

Gln Leu Gln Ile Leu Ser Asp Phe Glu Lys Asp Val Asp Leu Ala
            1115                1120                1125

Cys Gln Thr Val Leu Phe Lys Glu Val Asn Thr Cys Asn Pro Ser
            1130                1135                1140

Thr Ile Thr Gly Thr Leu Ser Arg Leu Ser Leu Asp Glu Asp Glu
            1145                1150                1155

Glu Pro Lys Ser Cys Leu Val Gly Pro Glu Gly Ser Leu Ser Phe
            1160                1165                1170

Ser Pro Leu Pro Gly Asn Ile Leu Val Pro Met Ala Ala Ser Pro
            1175                1180                1185

Gly Leu Gly Glu Pro Pro Pro Gln Glu Ala Asn Pro Val Tyr
            1190                1195                1200

Met Cys Gly Glu Gly Gly Leu Arg Gln Leu Asp Leu Thr Trp Leu
            1205                1210                1215

Arg Pro Thr Glu Pro Gly Ser Glu Gly Asp Tyr Met Val Leu Pro
            1220                1225                1230

Arg Arg Thr Leu Ser Leu Gln Pro Gly Gly Gly Gly Gly Gly
            1235                1240                1245

Glu Asp Ala Pro Arg Ala Arg Pro Glu Gly Thr Pro Arg Arg Ala
            1250                1255                1260

Ala Lys Thr Val Ala His Thr Glu Gly Tyr Pro Ser Phe Leu Ser
            1265                1270                1275
```

-continued

| | | | | | | | | | |
|---|---|---|---|---|---|---|---|---|---|
| Val | Asp | His | Ser | Gly | Leu | Gly | Leu | Gly | Pro | Ala | Tyr | Gly | Ser | Leu |
| 1280 | | | | 1285 | | | | 1290 | |

Val Asp His Ser Gly Leu Gly Leu Gly Pro Ala Tyr Gly Ser Leu
    1280                1285                1290

Gln Asn Pro Tyr Gly Met Thr Phe Gln Pro Pro Pro Thr Pro
    1295                1300                1305

Ser Ala Arg Gln Val Pro Glu Pro Gly Glu Arg Ser Arg Thr Met
    1310                1315                1320

Pro Arg Thr Val Pro Gly Ser Thr Met Lys Met Gly Ser Leu Glu
    1325                1330                1335

Arg Lys Lys Leu Arg Tyr Ser Asp Leu Asp Phe Glu Lys Val Met
    1340                1345                1350

His Thr Arg Lys Arg His Ser Glu Leu Tyr His Glu Leu Asn Gln
    1355                1360                1365

Lys Phe His Thr Phe Asp Arg Tyr Arg Ser Gln Ser Thr Ala Lys
    1370                1375                1380

Arg Glu Lys Arg Trp Ser Val Ser Ser Gly Gly Ala Ala Glu Arg
    1385                1390                1395

Ser Val Cys Thr Asp Lys Pro Ser Pro Gly Glu Arg Pro Ser Leu
    1400                1405                1410

Ser Gln His Arg Arg His Gln Ser Trp Ser Thr Phe Lys Ser Met
    1415                1420                1425

Thr Leu Gly Ser Leu Pro Pro Lys Pro Arg Glu Arg Leu Thr Leu
    1430                1435                1440

His Arg Ala Ala Ala Trp Glu Pro Thr Glu Pro Pro Asp Gly Asp
    1445                1450                1455

Phe Gln Thr Glu Val
    1460

<210> SEQ ID NO 17
<211> LENGTH: 4554
<212> TYPE: DNA
<213> ORGANISM: homo sapiens
<220> FEATURE:
<221> NAME/KEY: misc_feature
<223> OTHER INFORMATION: A splice variant of the DNA having the
      nucleotide sequence of SEQ ID NO:1

<400> SEQUENCE: 17
atgaccccag cctgtcccct cttactgtct gtgattctgt ccctgcgcct ggccaccgcc     60
ttcgaccccg cccccagtgc ctgctctgcc ctggcctcgg gtgtgctcta cggggccttc    120
tcgctgcagg acctctttcc taccatcgcc tcgggctgct cctggaccct ggagaaccct    180
gaccccacca gtactccct ctacctgcgc ttcaaccgcc aggagcaggt gtgcgcacac    240
tttgcccccc gcctgctgcc cctggaccac tacctggtca ctttacctg cctgcggcct    300 agccccgagg aggcggtggc ccaggcggag tcagaggtgg gcggccaga agaggaggag    360 gcagaggcgc agcggggtt ggagctgtgc agcggctcag gccccttac cttcctgcac    420 ttcgacaaga acttcgtgca gctgtgcctg tcggctgagc cctccgaggc ccgcgcctg    480 ctggcgcccg ctgccctagc cttccgcttt gtcgaggtct tgctcatcaa caacaacaac    540
tctagccaat tcacctgtgg tgtgctctgc cgctggagtg aggagtgtgg ccgcgctgcc    600
ggcagggcct gcggctttgc tcagccaggc tgcagctgcc ctggagaggc gggggccggc    660
tccaccacca ccacatctcc aggccctcct gctgcccaca ccctgtccaa tgccctggtg    720 ccgggggcc cagccccacc tgctgaggcc gatttgcact cggggagcag caatgatctg    780
ttcacaaccg agatgagata tggtgaggag ccggaagagg aaccgaaagt gaaaacccag    840

-continued

```
tggccgaggt ctgcagatga gcctgggcta tacatggcgc agacaggcga cccggcggct    900
gaggagtggt ccccgtggag cgtgtgttcc ctgacgtgtg ggcagggtct gcaggtgcgg    960
acccgctcct gtgtgtcctc ccctatggg accctgtgca gcgggcccct gcgggagacc   1020
aggccctgca acaattcagc cacctgccca gtggaaggcc agtggttaga atgggtccc    1080
tggggcccat gctccacgtc ctgtgccaat gggaccccaac agcgcagccg gaagtgcagc  1140
gtggcgggcc cagcctgggc cacatgcacg ggtgccctca ctgacacccg ggagtgcagc   1200
aacctcgagt gcccggccac tgatagcaag tgggggccat ggaatgcgtg gagcctgtgc   1260
tctaagacgt gtgacacagg ctggcagcgc cgcttccgca tgtgccaggc cacgggcacg   1320
cagggctacc cctgcgaggg caccggagag gaggtgaagc cttgtagtga aagaggtgt    1380
ccagccttcc atgagatgtg cagggatgag tacgtgatgc tgatgacgtg gaagaaggca   1440
gctgctggcg agatcatcta caacaagtgc ccccgaatg cctcagggtc tgccagccgc    1500
cgctgtctcc tcagtgccca aggcgtggcg tactgggggc tgcccagctt tgctcgctgc   1560
atctcccatg agtaccgcta cctgtatctg tcacttaggg agcacctggc caaggggcag   1620
cgcatgctgg caggcgaggg catgtcgcag gtggtgcgca gcctgcagga gctactggcc   1680
cggcgcacct actatagtgg ggacctgctc ttctctgtgg acattctgag gaatgtcact   1740
gacacccttta agagggccac ctacgtgccc tcggctgatg atgtgcagcg cttcttccag   1800
gtggtgagct tcatggtgga tgcggaaaac aaggagaagt gggacgatgc tcagcaggtg   1860
tccccctggct ctgtgcacct gctccgtgtc gtggaggact tcattcacct ggtgggcgat   1920
gctctcaagg ccttccagag ctctctgatt gtcacagata atctagtgat cagcattcag   1980
cgagagcccg tctcagctgt gtccagtgac atcacgttcc ccatgcgggg ccgccggggc   2040
atgaaggact gggtgcggca ctcagaggac cgcctcttcc tgcccaagga ggtgctcagc   2100
ctctcctccc cagggaagcc agccacatct ggggcagcag gcagccctgg caggggagg   2160
ggcccaggaa cggtgcctcc tggcccaggc cactcccacc agcgcctcct cccagcagac   2220
cctgatgagt cctcctactt tgtgatcggt gctgtactct accgcaccct tggcctcatc   2280
ctgccgcctc caggccccc gctggccgtc acatcccggg tgatgacagt gactgtgcgc   2340
cccccctaccc agcctccagc tgagcccctc atcactgtgg agctctccta catcatcaat   2400
gggaccacgg atccccattg cgccagctgg gactactcca gagcagatgc cagctcagga   2460
gactgggaca ctgaaaattg ccagaccctg gagacccagg cagctcacac ccgctgccag   2520
tgccagcacc tgtccacctt tgctgtacta gcccagccgc ccaaggacct gaccctggag   2580
ctggcgggct ccccctcggt ccccctggtg atcggctgtg cagtgtcgtg catggcgctg   2640
ctcacccctgc tcgccatcta tgccgccttt tggaggttca taaaatctga acgctccatc   2700
atcttgctga acttctgcct gtccatcttg gcatccaaca tcctgatcct cgtgggccag   2760
tcccgggtgc tgagcaaggg cgtgtgcacc atgacggctg ccttcctgca cttcttcttt   2820
ctctcctcct tttgctgggt gcttaccgag gcctggcagt cctacctggc tgtcattggg   2880
cggatgcgca cccgcctcgt tcgcaagcgc ttcctctgcc tgggctgggg tctgcctgcc   2940
ctggtggtgg ccgtgtctgt tggctttacc cgaacgaaag gatacggtac atccagctac   3000
tgctggctct ccctggaggg cggcctgctc tacgcctttg tgggccctgc agccgtcatt   3060
gtcctggtga acatgctcat cggaatcatc gtcttcaaca agctcatggc acgtgatggc   3120
atctccgaca aatccaagaa gcagagggcc gggtcggagc ggtgcccctg gccagcctg   3180
```

```
ctcctcccct gctcagcgtg tggagcggtc cccagccccc tgctcagctc agcctcggcc    3240
aggaacgcca tggcctcact ctggagctcc tgcgtggtgc tgcccctgct ggcgctcacc    3300
tggatgtctg ccgtcctggc tatgacagac cgccgttccg tcctcttcca ggccctcttt    3360
gctgtcttca actccgcgca gggctttgtc atcactgctg tgcactgctt cctgcgccga    3420
gaggtccagg atgtggtgaa gtgccagatg ggggtgtgcc gggctgatga gagcgaagac    3480
tcccctgact cgtgtaagaa cgggcagctg cagatcctgt cagactttga aaaggatgtg    3540
gatctggctt gtcaaacagt gctgttcaag gaggtcaaca cttgcaaccc gtccaccatc    3600
acgggcacac tatcccgcct gtccctggat gaggatgagg agcccaagtc ctgcctcgtg    3660
ggccctgagg gcagcctcag cttctcacca ctgcctggga atatcctggt gcccatggca    3720
gcctcaccag ggctggggga gcctccgccc cacaggagg ccaaccctgt ttacatgtgt    3780
ggggagggtg gcctgcggca gctggacctc acatggctgc ggcccactga gccaggctct    3840
gagggagact acatggtgct gccccggcgg actttgagcc tgcagcctgg cggtgggggt    3900
ggaggtggtg aggatgcccc cagggcccgg ccggagggga ccccccggcg agctgccaag    3960
acagtggccc acactgaagg ctaccccagc ttcctgtccg tggaccactc gggcctgggg    4020
ctgggccctg cctatggatc tctccagaat ccctatggaa tgaccttcca accgccaccg    4080
ccgacaccca cgcccccgcca agtgcccgag ccaggggagc gcagccggac catgcctcgc    4140
accgtgcccg gctctaccat gaagatgggc tccctggagc gaaagaaatt acggtattca    4200
gacctggact ttgagaaggt gatgcacacc cggaaacggc attcagaact ctaccacgag    4260
ctcaaccaga agttccacac tttcgaccgc taccgcagcc agtccacggc caagagggag    4320
aagcggtgga gtgtgtcctc gggtggggca gccgagcgga gcgtgtgcac cgataagccc    4380
agccctgggg agcgccccag cttgtcccaa catcggcgcc atcagagctg gagcaccttc    4440
aaatctatga cactgggctc gctgcccccc aagccccgag aacggctgac tctgcaccgg    4500
gcagcagcct gggagcccac agaaccaccg gatggtgact ccagacaga ggtg           4554
```

<210> SEQ ID NO 18
<211> LENGTH: 1518
<212> TYPE: PRT
<213> ORGANISM: homo sapiens
<220> FEATURE:
<221> NAME/KEY: misc_feature
<223> OTHER INFORMATION: Protein encoded by the DNA having a
      nucleotide sequence of SEQ ID NO:17
<220> FEATURE:
<221> NAME/KEY: DOMAIN
<222> LOCATION: (297)..(350)
<223> OTHER INFORMATION: TSP-I domain
<220> FEATURE:
<221> NAME/KEY: DOMAIN
<222> LOCATION: (352)..(405)
<223> OTHER INFORMATION: TSP-I domain
<220> FEATURE:
<221> NAME/KEY: DOMAIN
<222> LOCATION: (408)..(461)
<223> OTHER INFORMATION: TSP-I domain
<220> FEATURE:
<221> NAME/KEY: TRANSMEM
<222> LOCATION: (870)..(890)
<223> OTHER INFORMATION: transmembrane domain
<220> FEATURE:
<221> NAME/KEY: TRANSMEM
<222> LOCATION: (899)..(919)
<223> OTHER INFORMATION: transmembrane domain
<220> FEATURE:
<221> NAME/KEY: TRANSMEM
<222> LOCATION: (928)..(948)
<223> OTHER INFORMATION: transmembrane domain

```
<220> FEATURE:
<221> NAME/KEY: TRANSMEM
<222> LOCATION: (970)..(990)
<223> OTHER INFORMATION: transmembrane domain
<220> FEATURE:
<221> NAME/KEY: TRANSMEM
<222> LOCATION: (1012)..(1032)
<223> OTHER INFORMATION: transmembrane domain
<220> FEATURE:
<221> NAME/KEY: TRANSMEM
<222> LOCATION: (1087)..(1107)
<223> OTHER INFORMATION: transmembrane domain
<220> FEATURE:
<221> NAME/KEY: TRANSMEM
<222> LOCATION: (1114)..(1134)
<223> OTHER INFORMATION: transmembrane domain

<400> SEQUENCE: 18

Met Thr Pro Ala Cys Pro Leu Leu Leu Ser Val Ile Leu Ser Leu Arg
1               5                   10                  15

Leu Ala Thr Ala Phe Asp Pro Ala Pro Ser Ala Cys Ser Ala Leu Ala
            20                  25                  30

Ser Gly Val Leu Tyr Gly Ala Phe Ser Leu Gln Asp Leu Phe Pro Thr
        35                  40                  45

Ile Ala Ser Gly Cys Ser Trp Thr Leu Glu Asn Pro Asp Pro Thr Lys
    50                  55                  60

Tyr Ser Leu Tyr Leu Arg Phe Asn Arg Gln Glu Gln Val Cys Ala His
65                  70                  75                  80

Phe Ala Pro Arg Leu Leu Pro Leu Asp His Tyr Leu Val Asn Phe Thr
                85                  90                  95

Cys Leu Arg Pro Ser Pro Glu Glu Ala Val Ala Gln Ala Glu Ser Glu
            100                 105                 110

Val Gly Arg Pro Glu Glu Glu Glu Ala Glu Ala Ala Ala Gly Leu Glu
        115                 120                 125

Leu Cys Ser Gly Ser Gly Pro Phe Thr Phe Leu His Phe Asp Lys Asn
    130                 135                 140

Phe Val Gln Leu Cys Leu Ser Ala Glu Pro Ser Glu Ala Pro Arg Leu
145                 150                 155                 160

Leu Ala Pro Ala Ala Leu Ala Phe Arg Phe Val Glu Val Leu Leu Ile
                165                 170                 175

Asn Asn Asn Asn Ser Ser Gln Phe Thr Cys Gly Val Leu Cys Arg Trp
            180                 185                 190

Ser Glu Glu Cys Gly Arg Ala Ala Gly Arg Ala Cys Gly Phe Ala Gln
        195                 200                 205

Pro Gly Cys Ser Cys Pro Gly Glu Ala Gly Ala Gly Ser Thr Thr Thr
    210                 215                 220

Thr Ser Pro Gly Pro Pro Ala Ala His Thr Leu Ser Asn Ala Leu Val
225                 230                 235                 240

Pro Gly Gly Pro Ala Pro Pro Ala Glu Ala Asp Leu His Ser Gly Ser
                245                 250                 255

Ser Asn Asp Leu Phe Thr Thr Glu Met Arg Tyr Gly Glu Glu Pro Glu
            260                 265                 270

Glu Glu Pro Lys Val Lys Thr Gln Trp Pro Arg Ser Ala Asp Glu Pro
        275                 280                 285

Gly Leu Tyr Met Ala Gln Thr Gly Asp Pro Ala Ala Glu Glu Trp Ser
    290                 295                 300

Pro Trp Ser Val Cys Ser Leu Thr Cys Gly Gln Gly Leu Gln Val Arg
305                 310                 315                 320
```

-continued

```
Thr Arg Ser Cys Val Ser Ser Pro Tyr Gly Thr Leu Cys Ser Gly Pro
            325                 330                 335

Leu Arg Glu Thr Arg Pro Cys Asn Asn Ser Ala Thr Cys Pro Val Glu
            340                 345                 350

Gly Gln Trp Leu Glu Trp Gly Pro Trp Gly Pro Cys Ser Thr Ser Cys
            355                 360                 365

Ala Asn Gly Thr Gln Gln Arg Ser Arg Lys Cys Ser Val Ala Gly Pro
            370                 375                 380

Ala Trp Ala Thr Cys Thr Gly Ala Leu Thr Asp Thr Arg Glu Cys Ser
385                 390                 395                 400

Asn Leu Glu Cys Pro Ala Thr Asp Ser Lys Trp Gly Pro Trp Asn Ala
                405                 410                 415

Trp Ser Leu Cys Ser Lys Thr Cys Asp Thr Gly Trp Gln Arg Arg Phe
            420                 425                 430

Arg Met Cys Gln Ala Thr Gly Thr Gln Gly Tyr Pro Cys Glu Gly Thr
        435                 440                 445

Gly Glu Glu Val Lys Pro Cys Ser Glu Lys Arg Cys Pro Ala Phe His
    450                 455                 460

Glu Met Cys Arg Asp Glu Tyr Val Met Leu Met Thr Trp Lys Lys Ala
465                 470                 475                 480

Ala Ala Gly Glu Ile Ile Tyr Asn Lys Cys Pro Pro Asn Ala Ser Gly
                485                 490                 495

Ser Ala Ser Arg Arg Cys Leu Leu Ser Ala Gln Gly Val Ala Tyr Trp
            500                 505                 510

Gly Leu Pro Ser Phe Ala Arg Cys Ile Ser His Glu Tyr Arg Tyr Leu
        515                 520                 525

Tyr Leu Ser Leu Arg Glu His Leu Ala Lys Gly Gln Arg Met Leu Ala
    530                 535                 540

Gly Glu Gly Met Ser Gln Val Val Arg Ser Leu Gln Glu Leu Leu Ala
545                 550                 555                 560

Arg Arg Thr Tyr Tyr Ser Gly Asp Leu Leu Phe Ser Val Asp Ile Leu
                565                 570                 575

Arg Asn Val Thr Asp Thr Phe Lys Arg Ala Thr Tyr Val Pro Ser Ala
            580                 585                 590

Asp Asp Val Gln Arg Phe Phe Gln Val Val Ser Phe Met Val Asp Ala
        595                 600                 605

Glu Asn Lys Glu Lys Trp Asp Asp Ala Gln Gln Val Ser Pro Gly Ser
    610                 615                 620

Val His Leu Leu Arg Val Val Glu Asp Phe Ile His Leu Val Gly Asp
625                 630                 635                 640

Ala Leu Lys Ala Phe Gln Ser Ser Leu Ile Val Thr Asp Asn Leu Val
                645                 650                 655

Ile Ser Ile Gln Arg Glu Pro Val Ser Ala Val Ser Ser Asp Ile Thr
            660                 665                 670

Phe Pro Met Arg Gly Arg Gly Met Lys Asp Trp Val Arg His Ser
        675                 680                 685

Glu Asp Arg Leu Phe Leu Pro Lys Glu Val Leu Ser Leu Ser Ser Pro
    690                 695                 700

Gly Lys Pro Ala Thr Ser Gly Ala Ala Gly Ser Pro Gly Arg Gly Arg
705                 710                 715                 720

Gly Pro Gly Thr Val Pro Pro Gly Pro His Ser His Gln Arg Leu
                725                 730                 735

Leu Pro Ala Asp Pro Asp Glu Ser Ser Tyr Phe Val Ile Gly Ala Val
```

-continued

```
                740                 745                 750
Leu Tyr Arg Thr Leu Gly Leu Ile Leu Pro Pro Arg Pro Pro Leu
            755                 760                 765
Ala Val Thr Ser Arg Val Met Thr Val Thr Val Arg Pro Pro Thr Gln
            770                 775                 780
Pro Pro Ala Glu Pro Leu Ile Thr Val Glu Leu Ser Tyr Ile Ile Asn
785             790                 795                 800
Gly Thr Thr Asp Pro His Cys Ala Ser Trp Asp Tyr Ser Arg Ala Asp
                805                 810                 815
Ala Ser Ser Gly Asp Trp Asp Thr Glu Asn Cys Gln Thr Leu Glu Thr
            820                 825                 830
Gln Ala Ala His Thr Arg Cys Gln Cys Gln His Leu Ser Thr Phe Ala
            835                 840                 845
Val Leu Ala Gln Pro Pro Lys Asp Leu Thr Leu Glu Leu Ala Gly Ser
850             855                 860
Pro Ser Val Pro Leu Val Ile Gly Cys Ala Val Ser Cys Met Ala Leu
865                 870                 875                 880
Leu Thr Leu Leu Ala Ile Tyr Ala Ala Phe Trp Arg Phe Ile Lys Ser
                885                 890                 895
Glu Arg Ser Ile Ile Leu Leu Asn Phe Cys Leu Ser Ile Leu Ala Ser
                900                 905                 910
Asn Ile Leu Ile Leu Val Gly Gln Ser Arg Val Leu Ser Lys Gly Val
            915                 920                 925
Cys Thr Met Thr Ala Ala Phe Leu His Phe Phe Phe Leu Ser Ser Phe
            930                 935                 940
Cys Trp Val Leu Thr Glu Ala Trp Gln Ser Tyr Leu Ala Val Ile Gly
945                 950                 955                 960
Arg Met Arg Thr Arg Leu Val Arg Lys Arg Phe Leu Cys Leu Gly Trp
                965                 970                 975
Gly Leu Pro Ala Leu Val Val Ala Val Ser Val Gly Phe Thr Arg Thr
            980                 985                 990
Lys Gly Tyr Gly Thr Ser Ser Tyr  Cys Trp Leu Ser Leu  Glu Gly Gly
            995                 1000                1005
Leu Leu  Tyr Ala Phe Val Gly  Pro Ala Ala Val Ile  Val Leu Val
            1010                1015                1020
Asn Met  Leu Ile Gly Ile Ile  Val Phe Asn Lys Leu  Met Ala Arg
            1025                1030                1035
Asp Gly  Ile Ser Asp Lys Ser  Lys Lys Gln Arg Ala  Gly Ser Glu
            1040                1045                1050
Arg Cys  Pro Trp Ala Ser Leu  Leu Leu Pro Cys Ser  Ala Cys Gly
            1055                1060                1065
Ala Val  Pro Ser Pro Leu Leu  Ser Ser Ala Ser Ala  Arg Asn Ala
            1070                1075                1080
Met Ala  Ser Leu Trp Ser Ser  Cys Val Val Leu Pro  Leu Leu Ala
            1085                1090                1095
Leu Thr  Trp Met Ser Ala Val  Leu Ala Met Thr Asp  Arg Arg Ser
            1100                1105                1110
Val Leu  Phe Gln Ala Leu Phe  Ala Val Phe Asn Ser  Ala Gln Gly
            1115                1120                1125
Phe Val  Ile Thr Ala Val His  Cys Phe Leu Arg Arg  Glu Val Gln
            1130                1135                1140
Asp Val  Val Lys Cys Gln Met  Gly Val Cys Arg Ala  Asp Glu Ser
            1145                1150                1155
```

```
Glu Asp Ser Pro Asp Ser Cys Lys Asn Gly Gln Leu Gln Ile Leu
    1160            1165                1170

Ser Asp Phe Glu Lys Asp Val Asp Leu Ala Cys Gln Thr Val Leu
    1175            1180                1185

Phe Lys Glu Val Asn Thr Cys Asn Pro Ser Thr Ile Thr Gly Thr
    1190            1195                1200

Leu Ser Arg Leu Ser Leu Asp Glu Asp Glu Glu Pro Lys Ser Cys
    1205            1210                1215

Leu Val Gly Pro Glu Gly Ser Leu Ser Phe Ser Pro Leu Pro Gly
    1220            1225                1230

Asn Ile Leu Val Pro Met Ala Ala Ser Pro Gly Leu Gly Glu Pro
    1235            1240                1245

Pro Pro Pro Gln Glu Ala Asn Pro Val Tyr Met Cys Gly Glu Gly
    1250            1255                1260

Gly Leu Arg Gln Leu Asp Leu Thr Trp Leu Arg Pro Thr Glu Pro
    1265            1270                1275

Gly Ser Glu Gly Asp Tyr Met Val Leu Pro Arg Arg Thr Leu Ser
    1280            1285                1290

Leu Gln Pro Gly Gly Gly Gly Gly Gly Glu Asp Ala Pro Arg
    1295            1300                1305

Ala Arg Pro Glu Gly Thr Pro Arg Arg Ala Ala Lys Thr Val Ala
    1310            1315                1320

His Thr Glu Gly Tyr Pro Ser Phe Leu Ser Val Asp His Ser Gly
    1325            1330                1335

Leu Gly Leu Gly Pro Ala Tyr Gly Ser Leu Gln Asn Pro Tyr Gly
    1340            1345                1350

Met Thr Phe Gln Pro Pro Pro Thr Pro Ser Ala Arg Gln Val
    1355            1360                1365

Pro Glu Pro Gly Glu Arg Ser Arg Thr Met Pro Arg Thr Val Pro
    1370            1375                1380

Gly Ser Thr Met Lys Met Gly Ser Leu Glu Arg Lys Lys Leu Arg
    1385            1390                1395

Tyr Ser Asp Leu Asp Phe Glu Lys Val Met His Thr Arg Lys Arg
    1400            1405                1410

His Ser Glu Leu Tyr His Glu Leu Asn Gln Lys Phe His Thr Phe
    1415            1420                1425

Asp Arg Tyr Arg Ser Gln Ser Thr Ala Lys Arg Glu Lys Arg Trp
    1430            1435                1440

Ser Val Ser Ser Gly Gly Ala Ala Glu Arg Ser Val Cys Thr Asp
    1445            1450                1455

Lys Pro Ser Pro Gly Glu Arg Pro Ser Leu Ser Gln His Arg Arg
    1460            1465                1470

His Gln Ser Trp Ser Thr Phe Lys Ser Met Thr Leu Gly Ser Leu
    1475            1480                1485

Pro Pro Lys Pro Arg Glu Arg Leu Thr Leu His Arg Ala Ala Ala
    1490            1495                1500

Trp Glu Pro Thr Glu Pro Pro Asp Gly Asp Phe Gln Thr Glu Val
    1505            1510                1515

<210> SEQ ID NO 19
<211> LENGTH: 4719
<212> TYPE: DNA
<213> ORGANISM: homo sapiens
<220> FEATURE:
```

<220> FEATURE:
<221> NAME/KEY: misc_feature
<223> OTHER INFORMATION: A splice variant of the DNA having the
      nucleotide sequence of SEQ ID NO:1.
<220> FEATURE:
<221> NAME/KEY: misc_feature
<223> OTHER INFORMATION: A splice variant of the DNA having the
      nucleotide sequence of SEQ ID NO:1

<400> SEQUENCE: 19

| | | | | | |
|---|---|---|---|---|---|
| atgacccag | cctgtccct | cttactgtct | gtgattctgt | ccctgcgcct | ggccaccgcc | 60 |
| ttcgaccccg | cccccagtgc | ctgctctgcc | ctggcctcgg | gtgtgctcta | cggggccttc | 120 |
| tcgctgcagg | acctctttcc | taccatcgcc | tcgggctgct | cctggaccct | ggagaaccct | 180 |
| gaccccacca | agtactccct | ctacctgcgc | ttcaaccgcc | aggagcaggt | gtgcgcacac | 240 |
| tttgccccc | gctgctgcc | cctggaccac | tacctggtca | actttacctg | cctgcggcct | 300 |
| agccccgagg | aggcggtggc | ccaggcggag | tcagaggtgg | ggcggccaga | agaggaggag | 360 |
| gcagaggcg | cagcgggtt | ggagctgtgc | agcggctcag | gccccttac | cttcctgcac | 420 |
| tcgacaaga | acttcgtgca | gctgtgcctg | tcggctgagc | cctccgaggc | ccgcgcctg | 480 |
| ctggcgcccg | ctgccctagc | cttccgcttt | gtcgaggtct | tgctcatcaa | caacaacaac | 540 |
| tctagccaat | tcacctgtgg | tgtgctctgc | cgctggagtg | aggagtgtgg | ccgcgctgcc | 600 |
| ggcagggcct | gcggctttgc | tcagccaggc | tgcagctgcc | ctggagaggc | ggggccggc | 660 |
| tccaccacca | ccacatctcc | aggccctcct | gctgcccaca | ccctgtccaa | tgccctggtg | 720 |
| cccggggcc | cagccccacc | tgctgaggcc | gatttgcact | cggggagcag | caatgatctg | 780 |
| ttcacaaccg | agatgagata | tggtgaggag | ccggaagagg | aaccgaaagt | gaaaacccag | 840 |
| tggccgaggt | ctgcagatga | gcctgggcta | tacatggcgc | agacaggcga | ccggcggct | 900 |
| gaggagtggt | ccccgtggag | cgtgtgttcc | ctgacgtgtg | ggcagggtct | gcaggtgcgg | 960 |
| acccgctcct | gtgtgtcctc | ccctatggg | accctgtgca | gcgggcccct | gcgggagacc | 1020 |
| aggccctgca | acaattcagc | cacctgccca | gtgcacggcg | tgtgggagga | gtgggggtcc | 1080 |
| tggagcctgt | gctcccgcag | ctgcgggcgg | gggtcccgga | gccggatgcg | gacctgcgtg | 1140 |
| ccccccagc | acggcggcaa | ggcctgcgag | ggtcctgagc | tgcagactaa | gctctgcagt | 1200 |
| atggctgcct | gccgtgga | aggccagtgg | ttagaatggg | gtccctgggg | cccatgctcc | 1260 |
| acgtcctgtg | ccaatgggac | ccaacagcgc | agccggaagt | gcagcgtggc | gggcccagcc | 1320 |
| tgggccacat | gcacgggtgc | cctcactgac | acccggagt | gcagcaacct | cgagtgcccg | 1380 |
| gccactgata | gcaagtgggg | gccatggaat | gcgtggagcc | tgtgctctaa | gacgtgtgac | 1440 |
| acaggctggc | agcgccgctt | ccgcatgtgc | caggccacgg | gcacgcaggg | ctaccctgc | 1500 |
| gagggcaccg | gagaggaggt | gaagccttgt | agtgagaaga | ggtgtccagc | cttccatgag | 1560 |
| atgtgcaggg | atgagtacgt | gatgctgatg | acgtggaaga | aggcagctgc | tggcgagatc | 1620 |
| atctacaaca | agtgccccc | gaatgcctca | gggtctgcca | gccgccgctg | tctcctcagt | 1680 |
| gcccaaggcg | tggcgtactg | ggggctgccc | agctttgctc | gctgcatctc | ccatgagtac | 1740 |
| cgctacctgt | atctgtcact | tagggagcac | ctggccaagg | ggcagcgcat | gctggcaggc | 1800 |
| gagggcatgt | cgcaggtggt | gcgcagcctg | caggagctac | tggcccggcg | cacctactat | 1860 |
| agtggggacc | tgctcttctc | tgtggacatt | ctgaggaatg | tcactgacac | ctttaagagg | 1920 |
| gccacctacg | tgcctcggc | tgatgatgtg | cagcgcttct | tccaggtggt | gagcttcatg | 1980 |
| gtggatgcg | aaaacaagga | gaagtgggac | gatgctcagc | aggtgtcccc | tggctctgtg | 2040 |
| cacctgctcc | gtgtcgtgga | ggacttcatt | cacctggtgg | gcgatgctct | caaggccttc | 2100 |

```
cagagctctc tgattgtcac agataatcta gtgatcagca ttcagcgaga gcccgtctca    2160
gctgtgtcca gtgacatcac gttccccatg cggggccgcc ggggcatgaa ggactgggtg    2220
cggcactcag aggaccgcct cttcctgccc aaggaggtgc tcagcctctc ctccccaggg    2280
aagccagcca catctggggc agcaggcagc cctggcaggg ggaggggccc aggaacggtg    2340
cctcctggcc caggccactc ccaccagcgc ctcctcccag cagaccctga tgagtcctcc    2400
tactttgtga tcggtgctgt actctaccgc acccttggcc tcatcctgcc gcctcccagg    2460
cccccgctgg ccgtcacatc ccgggtgatg acagtgactg tgcgcccccc tacccagcct    2520
ccagctgagc ccctcatcac tgtggagctc tcctacatca tcaatgggac cacggatccc    2580
cattgcgcca gctgggacta ctccagagca gatgccagct caggagactg ggacactgaa    2640
aattgccaga ccctggagac ccaggcagct cacacccgct gccagtgcca gcacctgtcc    2700
acctttgctg tactagccca gccgcccaag gacctgaccc tggagctggc gggctccccc    2760
tcggtccccc tggtgatcgg ctgtgcagtg tcgtgcatgg cgctgctcac cctgctcgcc    2820
atctatgccg cctttggag gttcataaaa tctgaacgct ccatcatctt gctgaacttc    2880
tgcctgtcca tcttggcatc caacatcctg atcctcgtgg gccagtcccg ggtgctgagc    2940
aagggcgtgt gcaccatgac ggctgccttc ctgcacttct tctttctctc ctccttttgc    3000
tgggtgctta ccgaggcctg gcagtcctac ctggctgtca ttgggcggat gcgcacccgc    3060
ctcgttcgca agcgcttcct ctgcctgggc tggggtctgc ctgccctggt ggtggccgtg    3120
tctgttggct ttacccgaac gaaaggatac ggtacatcca gctactgctg gctctccctg    3180
gagggcggcc tgctctacgc ctttgtgggc cctgcagccg tcattgtcct ggtgaacatg    3240
ctcatcggaa tcatcgtctt caacaagctc atggcacgtg atggcatctc cgacaaatcc    3300
aagaagcaga gggccgggtc ggagcggtgc ccctgggcca gctgctcct cccctgctca    3360
gcgtgtggag cggtccccag cccctgctc agctcagcct cggccaggaa cgccatggcc    3420
tcactctgga gctcctgcgt ggtgctgccc ctgctggcgc tcacctggat gtctgccgtc    3480
ctggctatga cagaccgccg ttccgtcctc ttccaggccc tctttgctgt cttcaactcc    3540
gcgcagggct tgtcatcac tgctgtgcac tgcttcctgc gccgagaggt ccaggatgtg    3600
gtgaagtgcc agatggggt gtgccgggct gatgagagcg aagactcccc tgactcgtgt    3660
aagaacgggc agctgcagat cctgtcagac tttgaaaagg atgtggatct ggcttgtcaa    3720
acagtgctgt tcaaggaggt caacacttgc aacccgtcca ccatcacggg cacactatcc    3780
cgcctgtccc tggatgagga tgaggagccc aagtcctgcc tcgtgggccc tgagggcagc    3840
ctcagcttct caccactgcc tgggaatatc tggtgccca tggcagcctc accagggctg    3900
ggggagcctc cgcccccaca ggaggccaac cctgtttaca tgtgtgggga gggtggcctg    3960
cggcagctgg acctcacatg gctgcggccc actgagccag gctctgaggg agactacatg    4020
gtgctgcccc ggcggacttt gagcctgcag cctggcggtg ggggtggagg tggtgaggat    4080
gcccccaggg cccggccgga ggggaccccc cggcgagctg ccaagacagt ggcccacact    4140
gaaggctacc ccagcttcct gtccgtggac cactcgggcc tggggctggg ccctgcctat    4200
ggatctctcc agaatcccta tggaatgacc ttccaaccgc caccgccgac acccagcgcc    4260
cgccaagtgc ccgagccagg ggagcgcagc cggaccatgc ctcgcaccgt gccgggctct    4320
accatgaaga tgggctccct ggagcgaaag aaattacggt attcagacct ggactttgag    4380
aaggtgatgc acacccggaa acggcattca gaactctacc acgagctcaa ccagaagttc    4440
```

-continued

| | |
|---|---|
| cacactttcg accgctaccg cagccagtcc acggccaaga gggagaagcg gtggagtgtg | 4500 |
| tcctcgggtg gggcagccga gcggagcgtg tgcaccgata agcccagccc tggggagcgc | 4560 |
| cccagcttgt cccaacatcg gcgccatcag agctggagca ccttcaaatc tatgacactg | 4620 |
| ggctcgctgc cccccaagcc ccgagaacgg ctgactctgc accgggcagc agcctgggag | 4680 |
| cccacagaac caccggatgg tgacttccag acagaggtg | 4719 |

```
<210> SEQ ID NO 20
<211> LENGTH: 1573
<212> TYPE: PRT
<213> ORGANISM: homo sapiens
<220> FEATURE:
<221> NAME/KEY: misc_feature
<223> OTHER INFORMATION: Protein encoded by the DNA having a
      nucleotide sequence of SEQ ID NO:19
<220> FEATURE:
<221> NAME/KEY: DOMAIN
<222> LOCATION: (297)..(350)
<223> OTHER INFORMATION: TSP-I domain
<220> FEATURE:
<221> NAME/KEY: DOMAIN
<222> LOCATION: (352)..(405)
<223> OTHER INFORMATION: TSP-I domain
<220> FEATURE:
<221> NAME/KEY: DOMAIN
<222> LOCATION: (407)..(460)
<223> OTHER INFORMATION: TSP-I domain
<220> FEATURE:
<221> NAME/KEY: DOMAIN
<222> LOCATION: (463)..(516)
<223> OTHER INFORMATION: TSP-I domain
<220> FEATURE:
<221> NAME/KEY: TRANSMEM
<222> LOCATION: (925)..(945)
<223> OTHER INFORMATION: transmembrane domain
<220> FEATURE:
<221> NAME/KEY: TRANSMEM
<222> LOCATION: (954)..(974)
<223> OTHER INFORMATION: transmembrane domain
<220> FEATURE:
<221> NAME/KEY: TRANSMEM
<222> LOCATION: (983)..(1003)
<223> OTHER INFORMATION: transmembrane domain
<220> FEATURE:
<221> NAME/KEY: TRANSMEM
<222> LOCATION: (1025)..(1045)
<223> OTHER INFORMATION: transmembrane domain
<220> FEATURE:
<221> NAME/KEY: TRANSMEM
<222> LOCATION: (1067)..(1087)
<223> OTHER INFORMATION: transmembrane domain
<220> FEATURE:
<221> NAME/KEY: TRANSMEM
<222> LOCATION: (1142)..(1162)
<223> OTHER INFORMATION: transmembrane domain
<220> FEATURE:
<221> NAME/KEY: TRANSMEM
<222> LOCATION: (1169)..(1189)
<223> OTHER INFORMATION: transmembrane domain

<400> SEQUENCE: 20

Met Thr Pro Ala Cys Pro Leu Leu Leu Ser Val Ile Leu Ser Leu Arg
1               5                   10                  15

Leu Ala Thr Ala Phe Asp Pro Ala Pro Ser Ala Cys Ser Ala Leu Ala
            20                  25                  30

Ser Gly Val Leu Tyr Gly Ala Phe Ser Leu Gln Asp Leu Phe Pro Thr
        35                  40                  45

Ile Ala Ser Gly Cys Ser Trp Thr Leu Glu Asn Pro Asp Pro Thr Lys
    50                  55                  60

Tyr Ser Leu Tyr Leu Arg Phe Asn Arg Gln Glu Gln Val Cys Ala His
```

```
              65                  70                  75                  80
Phe Ala Pro Arg Leu Leu Pro Leu Asp His Tyr Leu Val Asn Phe Thr
                     85                  90                  95
Cys Leu Arg Pro Ser Pro Glu Glu Ala Val Ala Gln Ala Glu Ser Glu
                    100                 105                 110
Val Gly Arg Pro Glu Glu Glu Ala Glu Ala Ala Gly Leu Glu
                115                 120                 125
Leu Cys Ser Gly Ser Gly Pro Phe Thr Phe Leu His Phe Asp Lys Asn
        130                 135                 140
Phe Val Gln Leu Cys Leu Ser Ala Glu Pro Ser Glu Ala Pro Arg Leu
145                 150                 155                 160
Leu Ala Pro Ala Ala Leu Ala Phe Arg Phe Val Glu Val Leu Leu Ile
                165                 170                 175
Asn Asn Asn Asn Ser Ser Gln Phe Thr Cys Gly Val Leu Cys Arg Trp
                180                 185                 190
Ser Glu Glu Cys Gly Arg Ala Ala Gly Arg Ala Cys Gly Phe Ala Gln
                195                 200                 205
Pro Gly Cys Ser Cys Pro Gly Glu Ala Gly Ala Gly Ser Thr Thr Thr
            210                 215                 220
Thr Ser Pro Gly Pro Pro Ala Ala His Thr Leu Ser Asn Ala Leu Val
225                 230                 235                 240
Pro Gly Gly Pro Ala Pro Ala Glu Ala Asp Leu His Ser Gly Ser
                    245                 250                 255
Ser Asn Asp Leu Phe Thr Thr Glu Met Arg Tyr Gly Glu Glu Pro Glu
                260                 265                 270
Glu Glu Pro Lys Val Lys Thr Gln Trp Pro Arg Ser Ala Asp Glu Pro
            275                 280                 285
Gly Leu Tyr Met Ala Gln Thr Gly Asp Pro Ala Ala Glu Glu Trp Ser
        290                 295                 300
Pro Trp Ser Val Cys Ser Leu Thr Cys Gly Gln Gly Leu Gln Val Arg
305                 310                 315                 320
Thr Arg Ser Cys Val Ser Ser Pro Tyr Gly Thr Leu Cys Ser Gly Pro
                325                 330                 335
Leu Arg Glu Thr Arg Pro Cys Asn Asn Ser Ala Thr Cys Pro Val His
            340                 345                 350
Gly Val Trp Glu Glu Trp Gly Ser Trp Ser Leu Cys Ser Arg Ser Cys
        355                 360                 365
Gly Arg Gly Ser Arg Ser Arg Met Arg Thr Cys Val Pro Pro Gln His
    370                 375                 380
Gly Gly Lys Ala Cys Glu Gly Pro Glu Leu Gln Thr Lys Leu Cys Ser
385                 390                 395                 400
Met Ala Ala Cys Pro Val Glu Gly Gln Trp Leu Glu Trp Gly Pro Trp
                405                 410                 415
Gly Pro Cys Ser Thr Ser Cys Ala Asn Gly Thr Gln Arg Ser Arg
            420                 425                 430
Lys Cys Ser Val Ala Gly Pro Ala Trp Ala Thr Cys Thr Gly Ala Leu
        435                 440                 445
Thr Asp Thr Arg Glu Cys Ser Asn Leu Glu Cys Pro Ala Thr Asp Ser
    450                 455                 460
Lys Trp Gly Pro Trp Asn Ala Trp Ser Leu Cys Ser Lys Thr Cys Asp
465                 470                 475                 480
Thr Gly Trp Gln Arg Arg Phe Arg Met Cys Gln Ala Thr Gly Thr Gln
                485                 490                 495
```

-continued

```
Gly Tyr Pro Cys Glu Gly Thr Gly Glu Val Lys Pro Cys Ser Glu
            500                 505                 510
Lys Arg Cys Pro Ala Phe His Glu Met Cys Arg Asp Glu Tyr Val Met
            515                 520                 525
Leu Met Thr Trp Lys Lys Ala Ala Gly Glu Ile Ile Tyr Asn Lys
            530                 535                 540
Cys Pro Pro Asn Ala Ser Gly Ser Ala Ser Arg Arg Cys Leu Leu Ser
545                 550                 555                 560
Ala Gln Gly Val Ala Tyr Trp Gly Leu Pro Ser Phe Ala Arg Cys Ile
                565                 570                 575
Ser His Glu Tyr Arg Tyr Leu Tyr Leu Ser Leu Arg Glu His Leu Ala
            580                 585                 590
Lys Gly Gln Arg Met Leu Ala Gly Glu Gly Met Ser Gln Val Val Arg
            595                 600                 605
Ser Leu Gln Glu Leu Leu Ala Arg Arg Thr Tyr Tyr Ser Gly Asp Leu
            610                 615                 620
Leu Phe Ser Val Asp Ile Leu Arg Asn Val Thr Asp Thr Phe Lys Arg
625                 630                 635                 640
Ala Thr Tyr Val Pro Ser Ala Asp Asp Val Gln Arg Phe Phe Gln Val
                645                 650                 655
Val Ser Phe Met Val Asp Ala Glu Asn Lys Glu Lys Trp Asp Asp Ala
            660                 665                 670
Gln Gln Val Ser Pro Gly Ser Val His Leu Leu Arg Val Val Glu Asp
            675                 680                 685
Phe Ile His Leu Val Gly Asp Ala Leu Lys Ala Phe Gln Ser Ser Leu
            690                 695                 700
Ile Val Thr Asp Asn Leu Val Ile Ser Ile Gln Arg Glu Pro Val Ser
705                 710                 715                 720
Ala Val Ser Ser Asp Ile Thr Phe Pro Met Arg Gly Arg Arg Gly Met
                725                 730                 735
Lys Asp Trp Val Arg His Ser Glu Asp Arg Leu Phe Leu Pro Lys Glu
            740                 745                 750
Val Leu Ser Leu Ser Ser Pro Gly Lys Pro Ala Thr Ser Gly Ala Ala
            755                 760                 765
Gly Ser Pro Gly Arg Gly Arg Gly Pro Gly Thr Val Pro Pro Gly Pro
            770                 775                 780
Gly His Ser His Gln Arg Leu Leu Pro Ala Asp Pro Asp Glu Ser Ser
785                 790                 795                 800
Tyr Phe Val Ile Gly Ala Val Leu Tyr Arg Thr Leu Gly Leu Ile Leu
                805                 810                 815
Pro Pro Pro Arg Pro Leu Ala Val Thr Ser Arg Val Met Thr Val
            820                 825                 830
Thr Val Arg Pro Pro Thr Gln Pro Pro Ala Glu Pro Leu Ile Thr Val
            835                 840                 845
Glu Leu Ser Tyr Ile Ile Asn Gly Thr Thr Asp Pro His Cys Ala Ser
            850                 855                 860
Trp Asp Tyr Ser Arg Ala Asp Ala Ser Ser Gly Asp Trp Asp Thr Glu
865                 870                 875                 880
Asn Cys Gln Thr Leu Glu Thr Gln Ala Ala His Thr Arg Cys Gln Cys
                885                 890                 895
Gln His Leu Ser Thr Phe Ala Val Leu Ala Gln Pro Pro Lys Asp Leu
            900                 905                 910
```

```
Thr Leu Glu Leu Ala Gly Ser Pro Ser Val Pro Leu Ile Gly Cys
        915                 920                 925

Ala Val Ser Cys Met Ala Leu Leu Thr Leu Leu Ala Ile Tyr Ala Ala
        930                 935                 940

Phe Trp Arg Phe Ile Lys Ser Glu Arg Ser Ile Ile Leu Leu Asn Phe
945                 950                 955                 960

Cys Leu Ser Ile Leu Ala Ser Asn Ile Leu Ile Leu Val Gly Gln Ser
                965                 970                 975

Arg Val Leu Ser Lys Gly Val Cys Thr Met Thr Ala Ala Phe Leu His
            980                 985                 990

Phe Phe Phe Leu Ser Ser Phe Cys Trp Val Leu Thr Glu Ala Trp Gln
                995                 1000                1005

Ser Tyr Leu Ala Val Ile Gly Arg Met Arg Thr Arg Leu Val Arg
        1010                1015                1020

Lys Arg Phe Leu Cys Leu Gly Trp Gly Leu Pro Ala Leu Val Val
        1025                1030                1035

Ala Val Ser Val Gly Phe Thr Arg Thr Lys Gly Tyr Gly Thr Ser
        1040                1045                1050

Ser Tyr Cys Trp Leu Ser Leu Glu Gly Gly Leu Leu Tyr Ala Phe
        1055                1060                1065

Val Gly Pro Ala Ala Val Ile Val Leu Val Asn Met Leu Ile Gly
        1070                1075                1080

Ile Ile Val Phe Asn Lys Leu Met Ala Arg Asp Gly Ile Ser Asp
        1085                1090                1095

Lys Ser Lys Lys Gln Arg Ala Gly Ser Glu Arg Cys Pro Trp Ala
        1100                1105                1110

Ser Leu Leu Pro Cys Ser Ala Cys Gly Ala Val Pro Ser Pro
        1115                1120                1125

Leu Leu Ser Ser Ala Ser Ala Arg Asn Ala Met Ala Ser Leu Trp
        1130                1135                1140

Ser Ser Cys Val Val Leu Pro Leu Leu Ala Leu Thr Trp Met Ser
        1145                1150                1155

Ala Val Leu Ala Met Thr Asp Arg Arg Ser Val Leu Phe Gln Ala
        1160                1165                1170

Leu Phe Ala Val Phe Asn Ser Ala Gln Gly Phe Val Ile Thr Ala
        1175                1180                1185

Val His Cys Phe Leu Arg Arg Glu Val Gln Asp Val Val Lys Cys
        1190                1195                1200

Gln Met Gly Val Cys Arg Ala Asp Glu Ser Glu Asp Ser Pro Asp
        1205                1210                1215

Ser Cys Lys Asn Gly Gln Leu Gln Ile Leu Ser Asp Phe Glu Lys
        1220                1225                1230

Asp Val Asp Leu Ala Cys Gln Thr Val Leu Phe Lys Glu Val Asn
        1235                1240                1245

Thr Cys Asn Pro Ser Thr Ile Thr Gly Thr Leu Ser Arg Leu Ser
        1250                1255                1260

Leu Asp Glu Asp Glu Glu Pro Lys Ser Cys Leu Val Gly Pro Glu
        1265                1270                1275

Gly Ser Leu Ser Phe Ser Pro Leu Pro Gly Asn Ile Leu Val Pro
        1280                1285                1290

Met Ala Ala Ser Pro Gly Leu Gly Glu Pro Pro Pro Gln Glu
        1295                1300                1305

Ala Asn Pro Val Tyr Met Cys Gly Glu Gly Gly Leu Arg Gln Leu
```

-continued

```
              1310               1315                1320
Asp Leu Thr Trp Leu Arg Pro Thr Glu Pro Gly Ser Glu Gly Asp
       1325                1330                1335

Tyr Met Val Leu Pro Arg Arg Thr Leu Ser Leu Gln Pro Gly Gly
       1340                1345                1350

Gly Gly Gly Gly Gly Glu Asp Ala Pro Arg Ala Arg Pro Glu Gly
       1355                1360                1365

Thr Pro Arg Arg Ala Ala Lys Thr Val Ala His Thr Glu Gly Tyr
       1370                1375                1380

Pro Ser Phe Leu Ser Val Asp His Ser Gly Leu Gly Leu Gly Pro
       1385                1390                1395

Ala Tyr Gly Ser Leu Gln Asn Pro Tyr Gly Met Thr Phe Gln Pro
       1400                1405                1410

Pro Pro Pro Thr Pro Ser Ala Arg Gln Val Pro Glu Pro Gly Glu
       1415                1420                1425

Arg Ser Arg Thr Met Pro Arg Thr Val Pro Gly Ser Thr Met Lys
       1430                1435                1440

Met Gly Ser Leu Glu Arg Lys Lys Leu Arg Tyr Ser Asp Leu Asp
       1445                1450                1455

Phe Glu Lys Val Met His Thr Arg Lys Arg His Ser Glu Leu Tyr
       1460                1465                1470

His Glu Leu Asn Gln Lys Phe His Thr Phe Asp Arg Tyr Arg Ser
       1475                1480                1485

Gln Ser Thr Ala Lys Arg Glu Lys Arg Trp Ser Val Ser Ser Gly
       1490                1495                1500

Gly Ala Ala Glu Arg Ser Val Cys Thr Asp Lys Pro Ser Pro Gly
       1505                1510                1515

Glu Arg Pro Ser Leu Ser Gln His Arg Arg His Gln Ser Trp Ser
       1520                1525                1530

Thr Phe Lys Ser Met Thr Leu Gly Ser Leu Pro Pro Lys Pro Arg
       1535                1540                1545

Glu Arg Leu Thr Leu His Arg Ala Ala Ala Trp Glu Pro Thr Glu
       1550                1555                1560

Pro Pro Asp Gly Asp Phe Gln Thr Glu Val
       1565                1570

<210> SEQ ID NO 21
<211> LENGTH: 5399
<212> TYPE: DNA
<213> ORGANISM: homo sapiens
<220> FEATURE:
<221> NAME/KEY: misc_feature
<223> OTHER INFORMATION: A splice variant of the DNA having the
      nucleotide sequence of SEQ ID NO:1, which encodes hBAI2

<400> SEQUENCE: 21
gccgcgcggg agagcgggag cctcggccct ccgcgcggct gcagctacct accctgcgcc      60
cggccaggtc cccgacttag ggatggcaaa cttgcgcccc gtggccgccc cgccagcgc     120 cggcccccgc tcctgctgct gacggcgccc aggaaatcca cagcagtgat acatgtgacg     180
tccacactga cagtgccctc ctgtgggcat ggctcaggtt gtgcgcagtt cctggcacac     240
tggctgtaac tccgcccctt tctctccctc tcagtaaagc aagattacgc ggtgacatgc     300
ctcacagctg atcacgacac acggggatgg agagcaagag ttatgagaa tacaggttgg      360 atgggcaagg acataggat gaccccagcc tgtcccctct tactgtctgt gattctgtcc      420
```

```
ctgcgcctgg ccaccgcctt cgaccccgcc cccagtgcct gctctgccct ggcctcgggt    480
gtgctctacg gggccttctc gctgcaggac ctctttccta ccatcgcctc gggctgctcc    540
tggaccctgg agaaccctga ccccaccaag tactccctct acctgcgctt caaccgccag    600
gagcaggtgt gcgcacactt tgcccccgc ctgctgcccc tggaccacta cctggtcaac    660
tttacctgcc tgcggcctag ccccgaggag gcggtggccc aggcggagtc agaggtgggg    720
cggccagaag aggaggaggc agaggcggca gcggggttgg agctgtgcag cggctcaggc    780 cccttacct tcctgcactt cgacaagaac ttcgtgcagc tgtgcctgtc ggctgagccc    840
tccgaggccc cgcgcctgct ggcgcccgct gccctagcct ccgctttgt cgaggtcttg    900 ctcatcaaca caacaactc tagccaattc acctgtggtg tgctctgccg ctggagtgag    960
gagtgtggcc gcgctgccgg cagggcctgc ggctttgctc agccaggctg cagctgccct   1020
ggagaggcgg gggccggctc caccaccacc acatctccag gccctcctgc tgcccacacc   1080
ctgtccaatg ccctggtgcc cggggggccca gccccacctg ctgaggccga tttgcactcg   1140
gggagcagca atgatctgtt cacaaccgag atgagatatg gtgaggagcc ggaagaggaa   1200
ccgaaagtga aacccagtg gccgaggtct gcagatgagc ctgggctata catggcgcag   1260
acaggcgacc cggcggctga ggagtggtcc ccgtggagcg tgtgttccct gacgtgtggg   1320
cagggtctgc aggtgcggac ccgctcctgt gtgtcctccc cctatgggac cctgtgcagc   1380
gggcccctgc gggagaccag gccctgcaac aattcagcca cctgcccagt gcacggcgtg   1440
tgggaggagt gggggtcctg gagcctgtgc tcccgcagct gcgggcgggg gtcccggagc   1500
cggatgcgga cctgcgtgcc cccccagcac ggcggcaagg cctgcgaggg tcctgagctg   1560
cagactaagc tctgcagtat ggctgcctgc ccggtggaag gccagtggtt agaatggggt   1620
ccctggggcc catgctccac gtcctgtgcc aatgggaccc aacagcgcag ccggaagtgc   1680
agcgtggcgg gccagccctg gccacatgc acgggtgccc tcactgacac ccgggagtgc   1740
agcaacctcg agtgcccggc cactgatagc aagtggggc catggaatgc gtggagcctg   1800
tgctctaaga cgtgtgacac aggctggcag cgccgcttcc gcatgtgcca ggccacgggc   1860
acgcagggct accccctgcga gggcaccgga gaggaggtga agccttgtag tgagaagagg   1920
tgtccagcct tccatgagat gtgcagggat gagtacgtga tgctgatgac gtggaagaag   1980
gcagctgctg gcgagatcat ctacaacaag tgccccccga atgcctcagg gtctgccagc   2040
cgccgctgtc tcctcagtgc ccaaggcgtg gcgtactggg ggctgccag ctttgctcgc   2100 tgcatctccc atgagtaccg ctacctgtat ctgtcactta gggagcacct ggccaagggg   2160
cagcgcatgc tggcaggcga gggcatgtcg caggtggtgc gcagcctgca ggagctactg   2220 gccccggcgca cctactatag tggggacctg ctcttctctg tggacattct gaggaatgtc   2280
actgacacct ttaagagggc cacctacgtg ccctcggctg atgatgtgca gcgcttcttc   2340
caggtggtga gcttcatggt ggatgcggaa aacaaggaga agtgggacga tgctcagcag   2400
gtgtcccctg gctctgtgca cctgctccgt gtcgtggagg acttcattca cctggtgggc   2460
gatgctctca aggccttcca gagctctctg attgtcacag ataatctagt gatcagcatt   2520
cagcgagagc ccgtctcagc tgtgtccagt gacatcacgt tccccatgcg gggccgccgg   2580
ggcatgaagg actgggtgcg gcactcagag accgcctct tcctgcccaa ggaggtgctc   2640
agcctctcct ccccagggaa gccagccaca tctggggcag caggcagccc tggcagggg   2700 aggggcccag gaacggtgcc tcctggccca ggcactccc accagcgcct cctcccagca   2760
gaccctgatg agtcctccta ctttgtgatc ggtgctgtac tctaccgcac ccttggcctc   2820
```

```
atcctgccgc ctcccaggcc cccgctggcc gtcacatccc gggtgatgac agtgactgtg   2880 cgcccccta  cccagcctcc agctgagccc ctcatcactg tggagctctc ctacatcatc   2940
aatgggacca cggatcccca ttgcgccagc tgggactact ccagagcaga tgccagctca   3000
ggagactggg acactgaaaa ttgccagacc ctggagaccc aggcagctca caccgctgc    3060 cagtgccagc acctgtccac cttttgctgta ctagcccagc cgcccaagga cctgaccctg  3120
gagctggcgg gctcccctc  ggtccccctg gtgatcggct gtgcagtgtc gtgcatggcg   3180
ctgctcaccc tgctcgccat ctatgccgcc ttttggaggt tcataaaatc tgaacgctcc   3240
atcatcttgc tgaacttctg cctgtccatc ttggcatcca acatcctgat cctcgtgggc   3300
cagtcccggg tgctgagcaa gggcgtgtgc accatgacgg ctgccttcct gcacttcttc   3360
tttctctcct ccttttgctg ggtgcttacc gaggcctggc agtcctacct ggctgtcatt   3420
gggcggatgc gcacccgcct cgttcgcaag cgcttcctct gcctgggctg gggtctgcct   3480
gccctggtgg tggccgtgtc tgttggcttt acccgaacga aaggatacgg tacatccagc   3540
tactgctggc tctccctgga gggcggcctg ctctacgcct ttgtgggccc tgcagccgtc   3600
attgtcctgg tgaacatgct catcggaatc atcgtcttca acaagctcat ggcacgtgat   3660
ggcatctccg acaaatccaa gaagcagagg gccgggtcgg agcggtgccc ctgggccagc   3720
ctgctcctcc cctgctcagc gtgtggagcg gtccccagcc ccctgctcag ctcagcctcg   3780
gccaggaacg ccatggcctc actctggagc tcctgcgtgg tgctgcccct gctggcgctc   3840
acctggatgt ctgccgtcct ggctatgaca gaccgccgtt ccgtcctctt ccaggccctc   3900
tttgctgtct tcaactccgc gcagggcttt gtcatcactg ctgtgcactg cttcctgcgc   3960
cgagaggtcc aggatgtggt gaagtgccag atggggggtgt gccgggctga tgagagcgaa   4020
gactcccctg actcgtgtaa gaacgggcag ctgcagatcc tgtcagactt tgaaaaggat   4080
gtggatctgg cttgtcaaac agtgctgttc aaggaggtca acacttgcaa cccgtccacc   4140
atcacgggca cactatcccg cctgtccctg gatgaggatg aggagcccaa gtcctgcctc   4200
gtgggccctg agggcagcct cagcttctca ccactgcctg gaatatcct  ggtgccatg    4260 gcagcctcac cagggctggg ggagcctccg cccccacagg aggccaaccc tgtttacatg   4320
tgtggggagg gtgccctgcg gcagctggac ctcacatggc tgcggcccac tgagccaggc   4380
tctgagggag actacatggt gctgccccgg cggactttga gcctgcagcc tggcggtggg   4440
ggtggaggtg gtgaggatgc ccccagggcc cggcccgagg ggaccccccg gcgagctgcc   4500
aagacagtgg cccacactga aggctacccc agcttcctgt ccgtggacca ctcgggcctg   4560
gggctgggcc ctgcctatgg atctctccag aatccctatg gaatgacctt ccaaccgcca   4620
ccgccgacac ccagcgcccg ccaagtgccc gagccagggg agcgcagccg gaccatgcct   4680
cgcaccgtgc ccggctctac catgaagatg ggctccctgg agcgaaagaa attacggtat   4740
tcagacctgg actttgaggt gatgcacacc cggaaacggc attcagaact ctaccacgag   4800
ctcaaccaga agttccacac tttcgaccgc taccgcagcc agtccacggc caagagggag   4860
aagcggtgga gtgtgtcctc gggtggggcg gccgagcgga gcgtgtgcac cgataagccc   4920
agccctgggg agcgcccag  cttgtcccaa catcggcgcc atcagagctg gagcaccttc   4980
aaatctatga cactgggctc gctgcccccc aagccccgag aacggctgac tctgcaccgg   5040
gcagcagcct gggagcccac agaaccaccg gatggtgact ccagacaga  ggtgtgagtg   5100 ccacgctgga ctgcccactg catataaata tatatatctc tctattttca cactccactt   5160
```

-continued

```
tggaactacc caggagccag cgccctctcc cctctcccga gggctgggca gggaggcgcc    5220
gtggactcag ccaggctggg ggagccggac atggcttggc ctggggtccc agggcccttc    5280
cttgtttctc agaggcccct cagccactgg aacccatct tcagcccagc ctgtccgtcc     5340
ctgtcccggg ctggggaggg gggagggaa ctttgttggg aataaacttc actctgtgg      5399
```

```
<210> SEQ ID NO 22
<211> LENGTH: 1572
<212> TYPE: PRT
<213> ORGANISM: homo sapiens
<220> FEATURE:
<221> NAME/KEY: misc_feature
<223> OTHER INFORMATION: Protein encoded by the DNA having a
      nucleotide sequence of SEQ ID NO:21
<220> FEATURE:
<221> NAME/KEY: DOMAIN
<222> LOCATION: (297)..(350)
<223> OTHER INFORMATION: TSP-I domain
<220> FEATURE:
<221> NAME/KEY: DOMAIN
<222> LOCATION: (352)..(405)
<223> OTHER INFORMATION: TSP-I domain
<220> FEATURE:
<221> NAME/KEY: DOMAIN
<222> LOCATION: (407)..(460)
<223> OTHER INFORMATION: TSP-I domain
<220> FEATURE:
<221> NAME/KEY: DOMAIN
<222> LOCATION: (463)..(516)
<223> OTHER INFORMATION: TSP-I domain
<220> FEATURE:
<221> NAME/KEY: TRANSMEM
<222> LOCATION: (925)..(945)
<223> OTHER INFORMATION: transmembrane domain
<220> FEATURE:
<221> NAME/KEY: TRANSMEM
<222> LOCATION: (954)..(974)
<223> OTHER INFORMATION: transmembrane domain
<220> FEATURE:
<221> NAME/KEY: TRANSMEM
<222> LOCATION: (983)..(1003)
<223> OTHER INFORMATION: transmembrane domain
<220> FEATURE:
<221> NAME/KEY: TRANSMEM
<222> LOCATION: (1025)..(1045)
<223> OTHER INFORMATION: transmembrane domain
<220> FEATURE:
<221> NAME/KEY: TRANSMEM
<222> LOCATION: (1067)..(1087)
<223> OTHER INFORMATION: transmembrane domain
<220> FEATURE:
<221> NAME/KEY: TRANSMEM
<222> LOCATION: (1142)..(1162)
<223> OTHER INFORMATION: transmembrane domain
<220> FEATURE:
<221> NAME/KEY: TRANSMEM
<222> LOCATION: (1169)..(1189)
<223> OTHER INFORMATION: transmembrane domain

<400> SEQUENCE: 22
```

```
Met Thr Pro Ala Cys Pro Leu Leu Ser Val Ile Leu Ser Leu Arg
1               5                   10                  15

Leu Ala Thr Ala Phe Asp Pro Ala Pro Ser Ala Cys Ser Ala Leu Ala
            20                  25                  30

Ser Gly Val Leu Tyr Gly Ala Phe Ser Leu Gln Asp Leu Phe Pro Thr
        35                  40                  45

Ile Ala Ser Gly Cys Ser Trp Thr Leu Glu Asn Pro Asp Pro Thr Lys
    50                  55                  60

Tyr Ser Leu Tyr Leu Arg Phe Asn Arg Gln Glu Gln Val Cys Ala His
65                  70                  75                  80
```

```
Phe Ala Pro Arg Leu Leu Pro Leu Asp His Tyr Leu Val Asn Phe Thr
            85                  90                  95

Cys Leu Arg Pro Ser Pro Glu Glu Ala Val Ala Gln Ala Glu Ser Glu
            100                 105                 110

Val Gly Arg Pro Glu Glu Glu Ala Glu Ala Ala Gly Leu Glu
            115                 120                 125

Leu Cys Ser Gly Ser Gly Pro Phe Thr Phe Leu His Phe Asp Lys Asn
            130                 135                 140

Phe Val Gln Leu Cys Leu Ser Ala Glu Pro Ser Glu Ala Pro Arg Leu
145                 150                 155                 160

Leu Ala Pro Ala Ala Leu Ala Phe Arg Phe Val Glu Val Leu Leu Ile
            165                 170                 175

Asn Asn Asn Asn Ser Ser Gln Phe Thr Cys Gly Val Leu Cys Arg Trp
            180                 185                 190

Ser Glu Glu Cys Gly Arg Ala Ala Gly Arg Ala Cys Gly Phe Ala Gln
            195                 200                 205

Pro Gly Cys Ser Cys Pro Gly Glu Ala Gly Ala Gly Ser Thr Thr Thr
210                 215                 220

Thr Ser Pro Gly Pro Pro Ala Ala His Thr Leu Ser Asn Ala Leu Val
225                 230                 235                 240

Pro Gly Gly Pro Ala Pro Pro Ala Glu Ala Asp Leu His Ser Gly Ser
            245                 250                 255

Ser Asn Asp Leu Phe Thr Thr Glu Met Arg Tyr Gly Glu Glu Pro Glu
            260                 265                 270

Glu Glu Pro Lys Val Lys Thr Gln Trp Pro Arg Ser Ala Asp Glu Pro
            275                 280                 285

Gly Leu Tyr Met Ala Gln Thr Gly Asp Pro Ala Ala Glu Glu Trp Ser
            290                 295                 300

Pro Trp Ser Val Cys Ser Leu Thr Cys Gly Gln Gly Leu Gln Val Arg
305                 310                 315                 320

Thr Arg Ser Cys Val Ser Ser Pro Tyr Gly Thr Leu Cys Ser Gly Pro
            325                 330                 335

Leu Arg Glu Thr Arg Pro Cys Asn Asn Ser Ala Thr Cys Pro Val His
            340                 345                 350

Gly Val Trp Glu Glu Trp Gly Ser Trp Ser Leu Cys Ser Arg Ser Cys
            355                 360                 365

Gly Arg Gly Ser Arg Ser Arg Met Arg Thr Cys Val Pro Pro Gln His
            370                 375                 380

Gly Gly Lys Ala Cys Glu Gly Pro Glu Leu Gln Thr Lys Leu Cys Ser
385                 390                 395                 400

Met Ala Ala Cys Pro Val Glu Gly Gln Trp Leu Glu Trp Gly Pro Trp
                    405                 410                 415

Gly Pro Cys Ser Thr Ser Cys Ala Asn Gly Thr Gln Gln Arg Ser Arg
            420                 425                 430

Lys Cys Ser Val Ala Gly Pro Ala Trp Ala Thr Cys Thr Gly Ala Leu
            435                 440                 445

Thr Asp Thr Arg Glu Cys Ser Asn Leu Glu Cys Pro Ala Thr Asp Ser
450                 455                 460

Lys Trp Gly Pro Trp Asn Ala Trp Ser Leu Cys Ser Lys Thr Cys Asp
465                 470                 475                 480

Thr Gly Trp Gln Arg Arg Phe Arg Met Cys Gln Ala Thr Gly Thr Gln
            485                 490                 495

Gly Tyr Pro Cys Glu Gly Thr Gly Glu Glu Val Lys Pro Cys Ser Glu
```

-continued

```
                500                 505                 510
Lys Arg Cys Pro Ala Phe His Glu Met Cys Arg Asp Glu Tyr Val Met
            515                 520                 525

Leu Met Thr Trp Lys Lys Ala Ala Gly Glu Ile Ile Tyr Asn Lys
        530                 535                 540

Cys Pro Pro Asn Ala Ser Gly Ser Ala Ser Arg Arg Cys Leu Leu Ser
545                 550                 555                 560

Ala Gln Gly Val Ala Tyr Trp Gly Leu Pro Ser Phe Ala Arg Cys Ile
                565                 570                 575

Ser His Glu Tyr Arg Tyr Leu Tyr Leu Ser Leu Arg Glu His Leu Ala
            580                 585                 590

Lys Gly Gln Arg Met Leu Ala Gly Glu Met Ser Gln Val Val Arg
        595                 600                 605

Ser Leu Gln Glu Leu Leu Ala Arg Arg Thr Tyr Tyr Ser Gly Asp Leu
        610                 615                 620

Leu Phe Ser Val Asp Ile Leu Arg Asn Val Thr Asp Thr Phe Lys Arg
625                 630                 635                 640

Ala Thr Tyr Val Pro Ser Ala Asp Val Gln Arg Phe Phe Gln Val
                645                 650                 655

Val Ser Phe Met Val Asp Ala Glu Asn Lys Glu Lys Trp Asp Asp Ala
                660                 665                 670

Gln Gln Val Ser Pro Gly Ser Val His Leu Leu Arg Val Val Glu Asp
            675                 680                 685

Phe Ile His Leu Val Gly Asp Ala Leu Lys Ala Phe Gln Ser Ser Leu
        690                 695                 700

Ile Val Thr Asp Asn Leu Val Ile Ser Ile Gln Arg Glu Pro Val Ser
705                 710                 715                 720

Ala Val Ser Ser Asp Ile Thr Phe Pro Met Arg Gly Arg Arg Gly Met
                725                 730                 735

Lys Asp Trp Val Arg His Ser Glu Asp Arg Leu Phe Leu Pro Lys Glu
            740                 745                 750

Val Leu Ser Leu Ser Ser Pro Gly Lys Pro Ala Thr Ser Gly Ala Ala
        755                 760                 765

Gly Ser Pro Gly Arg Gly Arg Gly Pro Gly Thr Val Pro Pro Gly Pro
        770                 775                 780

Gly His Ser His Gln Arg Leu Leu Pro Ala Asp Pro Asp Glu Ser Ser
785                 790                 795                 800

Tyr Phe Val Ile Gly Ala Val Leu Tyr Arg Thr Leu Gly Leu Ile Leu
                805                 810                 815

Pro Pro Pro Arg Pro Pro Leu Ala Val Thr Ser Arg Val Met Thr Val
                820                 825                 830

Thr Val Arg Pro Pro Thr Gln Pro Pro Ala Glu Pro Leu Ile Thr Val
            835                 840                 845

Glu Leu Ser Tyr Ile Ile Asn Gly Thr Thr Asp Pro His Cys Ala Ser
        850                 855                 860

Trp Asp Tyr Ser Arg Ala Asp Ala Ser Ser Gly Asp Trp Asp Thr Glu
865                 870                 875                 880

Asn Cys Gln Thr Leu Glu Thr Gln Ala Ala His Thr Arg Cys Gln Cys
                885                 890                 895

Gln His Leu Ser Thr Phe Ala Val Leu Ala Gln Pro Pro Lys Asp Leu
            900                 905                 910

Thr Leu Glu Leu Ala Gly Ser Pro Ser Val Pro Leu Val Ile Gly Cys
        915                 920                 925
```

```
Ala Val Ser Cys Met Ala Leu Leu Thr Leu Leu Ala Ile Tyr Ala Ala
    930                 935                 940

Phe Trp Arg Phe Ile Lys Ser Glu Arg Ser Ile Ile Leu Leu Asn Phe
945                 950                 955                 960

Cys Leu Ser Ile Leu Ala Ser Asn Ile Leu Ile Leu Val Gly Gln Ser
                965                 970                 975

Arg Val Leu Ser Lys Gly Val Cys Thr Met Thr Ala Ala Phe Leu His
                980                 985                 990

Phe Phe Phe Leu Ser Ser Phe Cys Trp Val Leu Thr Glu Ala Trp Gln
            995                 1000                1005

Ser Tyr Leu Ala Val Ile Gly Arg Met Arg Thr Arg Leu Val Arg
        1010                1015                1020

Lys Arg Phe Leu Cys Leu Gly Trp Gly Leu Pro Ala Leu Val Val
        1025                1030                1035

Ala Val Ser Val Gly Phe Thr Arg Thr Lys Gly Tyr Gly Thr Ser
        1040                1045                1050

Ser Tyr Cys Trp Leu Ser Leu Glu Gly Gly Leu Leu Tyr Ala Phe
        1055                1060                1065

Val Gly Pro Ala Ala Val Ile Val Leu Val Asn Met Leu Ile Gly
        1070                1075                1080

Ile Ile Val Phe Asn Lys Leu Met Ala Arg Asp Gly Ile Ser Asp
        1085                1090                1095

Lys Ser Lys Lys Gln Arg Ala Gly Ser Glu Arg Cys Pro Trp Ala
        1100                1105                1110

Ser Leu Leu Leu Pro Cys Ser Ala Cys Gly Ala Val Pro Ser Pro
        1115                1120                1125

Leu Leu Ser Ser Ala Ser Ala Arg Asn Ala Met Ala Ser Leu Trp
        1130                1135                1140

Ser Ser Cys Val Val Leu Pro Leu Leu Ala Leu Thr Trp Met Ser
        1145                1150                1155

Ala Val Leu Ala Met Thr Asp Arg Arg Ser Val Leu Phe Gln Ala
        1160                1165                1170

Leu Phe Ala Val Phe Asn Ser Ala Gln Gly Phe Val Ile Thr Ala
        1175                1180                1185

Val His Cys Phe Leu Arg Arg Glu Val Gln Asp Val Val Lys Cys
        1190                1195                1200

Gln Met Gly Val Cys Arg Ala Asp Glu Ser Glu Asp Ser Pro Asp
        1205                1210                1215

Ser Cys Lys Asn Gly Gln Leu Gln Ile Leu Ser Asp Phe Glu Lys
        1220                1225                1230

Asp Val Asp Leu Ala Cys Gln Thr Val Leu Phe Lys Glu Val Asn
        1235                1240                1245

Thr Cys Asn Pro Ser Thr Ile Thr Gly Thr Leu Ser Arg Leu Ser
        1250                1255                1260

Leu Asp Glu Asp Glu Glu Pro Lys Ser Cys Leu Val Gly Pro Glu
        1265                1270                1275

Gly Ser Leu Ser Phe Ser Pro Leu Pro Gly Asn Ile Leu Val Pro
        1280                1285                1290

Met Ala Ala Ser Pro Gly Leu Gly Glu Pro Pro Pro Gln Glu
        1295                1300                1305

Ala Asn Pro Val Tyr Met Cys Gly Glu Gly Gly Leu Arg Gln Leu
        1310                1315                1320
```

-continued

Asp Leu Thr Trp Leu Arg Pro Thr Glu Pro Gly Ser Glu Gly Asp
1325                1330                1335

Tyr Met Val Leu Pro Arg Arg Thr Leu Ser Leu Gln Pro Gly Gly
1340                1345                1350

Gly Gly Gly Gly Gly Glu Asp Ala Pro Arg Ala Arg Pro Glu Gly
1355                1360                1365

Thr Pro Arg Arg Ala Ala Lys Thr Val Ala His Thr Glu Gly Tyr
1370                1375                1380

Pro Ser Phe Leu Ser Val Asp His Ser Gly Leu Gly Leu Gly Pro
1385                1390                1395

Ala Tyr Gly Ser Leu Gln Asn Pro Tyr Gly Met Thr Phe Gln Pro
1400                1405                1410

Pro Pro Pro Thr Pro Ser Ala Arg Gln Val Pro Glu Pro Gly Glu
1415                1420                1425

Arg Ser Arg Thr Met Pro Arg Thr Val Pro Gly Ser Thr Met Lys
1430                1435                1440

Met Gly Ser Leu Glu Arg Lys Lys Leu Arg Tyr Ser Asp Leu Asp
1445                1450                1455

Phe Glu Val Met His Thr Arg Lys Arg His Ser Glu Leu Tyr His
1460                1465                1470

Glu Leu Asn Gln Lys Phe His Thr Phe Asp Arg Tyr Arg Ser Gln
1475                1480                1485

Ser Thr Ala Lys Arg Glu Lys Arg Trp Ser Val Ser Ser Gly Gly
1490                1495                1500

Ala Ala Glu Arg Ser Val Cys Thr Asp Lys Pro Ser Pro Gly Glu
1505                1510                1515

Arg Pro Ser Leu Ser Gln His Arg Arg His Gln Ser Trp Ser Thr
1520                1525                1530

Phe Lys Ser Met Thr Leu Gly Ser Leu Pro Pro Lys Pro Arg Glu
1535                1540                1545

Arg Leu Thr Leu His Arg Ala Ala Ala Trp Glu Pro Thr Glu Pro
1550                1555                1560

Pro Asp Gly Asp Phe Gln Thr Glu Val
1565                1570

<210> SEQ ID NO 23
<211> LENGTH: 21
<212> TYPE: DNA
<213> ORGANISM: Artificial
<220> FEATURE:
<223> OTHER INFORMATION: Designed oligonucleotide for using as a primer

<400> SEQUENCE: 23
gacctctttc ctaccatcgc c                                                 21

<210> SEQ ID NO 24
<211> LENGTH: 19
<212> TYPE: DNA
<213> ORGANISM: Artificial
<220> FEATURE:
<223> OTHER INFORMATION: Designed oligonucleotide for using as a primer

<400> SEQUENCE: 24
cacaggctcc acgcattcc                                                    19

ASSAY EMPLOYING A G-PROTEIN COUPLED RECEPTOR THAT IS ACTIVATED BY CCK-8S

The present application is a continuation-in-part of International Application No. PCT/JP2004/017239, filed on Nov. 19, 2004, and International Application No. PCT/JP2006/309118, filed May 1, 2006, which, in turn, claim priority from Japanese Patent Application No. 2003-389624, filed Nov. 19, 2003; Japanese Patent Application No. 2004-130371, filed Apr. 26, 2004; Japanese Patent Application No. 2004-304780, filed Oct. 19, 2004; and Japanese Patent Application No. 2005-134367, filed May 2, 2005.

TECHNICAL FIELD

The present invention relates to a gene encoding a G-protein coupled receptor and the gene product thereof. More specifically, this invention relates to a gene encoding a G-protein coupled receptor for which cholecystokinin octapeptide sulfated form (hereunder, may also be referred to as "CCK-8S") acts as a ligand, and the gene product thereof. Further specifically, this invention relates to a DNA encoding a protein having a function as a G-protein coupled receptor or the complementary strand thereof, a DNA comprising a partial base sequence of the DNA, a recombinant vector containing the above DNA or the complementary strand thereof, and a transformant having the recombinant vector introduced therein. The invention also relates to a protein having a function as a G-protein coupled receptor, and an antibody against the protein. The invention further relates to a method for producing the protein. The invention also relates to a method of identifying a compound that inhibits or promotes a function of the protein and/or expression of a DNA encoding the protein. The invention further relates to a method of identifying an agonist and a ligand of the above protein. The invention further relates to an agonist or a ligand identified by the aforementioned identification method. The invention still further relates to a preventive agent and/or therapeutic agent for a disease attributable to a decrease in CCK-8S and/or a decrease in the function thereof (e.g. dementia (including Alzheimer's disease), anxiety disorders, obesity and diabetes), that comprises at least an agonist of the above protein. The present invention also relates to a method for preventing and/or a method for treating a disease attributable to a decrease in CCK-8S and/or a decrease in the function thereof, which is characterized by use of at least an agonist of the above protein. Furthermore, the present invention relates to a preventive agent and/or a therapeutic agent for a disease associated with angiogenesis (for example, cerebral infarction, cerebral contusion or tumor disease) or a medicinal composition, which comprises at least one selected from the DNA, the protein, the recombinant vector, the transformant and the antibody as described above. The invention also relates to a preventive agent and/or a therapeutic agent for a disease associated with angiogenesis which comprises a compound that inhibits and/or promotes a function of the above protein and/or expression of the above DNA. The invention further relates to a method for preventing and/or a method for treating a disease associated with angiogenesis which is characterized by use of at least one selected from the DNA, the protein, the recombinant vector, the transformant and the antibody as described above. The invention further relates to a method for preventing and/or a method for treating a disease associated with angiogenesis which is characterized by use of a compound that inhibits and/or promotes a function of the above protein and/or expression of the above DNA. The invention further relates to a quantitative or qualitative method for assaying the above protein or DNA, an assay method for diagnosis which comprises assaying the above protein or DNA, and a method for diagnosing a disease attributable to an abnormality in the above protein or DNA, such as a disease associated with angiogenesis, which is characterized by use of the above assay means. The invention also relates to a reagent kit and a diagnostic kit that comprise at least one selected from the DNA, the protein, the recombinant vector, the transformant and the antibody as described above. The invention further relates to a method of identifying a ligand of the above described protein.

Further, the present invention relates to a method for identifying a compound having antidepressant action. Specifically, the present invention relates to a method for identifying a compound having antidepressant action which is an antagonist of any one protein selected from the group consisting of a protein encoded by a DNA represented by a base sequence described in SEQ ID NO: 1 of the sequence listing and a homolog of the protein. Further, the present invention relates to a DNA encoding the homolog or a complementary strand thereof, a recombinant vector containing the DNA or the complementary strand thereof, and a transformant in which the recombinant vector is introduced. Furthermore, the present invention relates to a protein translated from a DNA encoding the splicing variant and a method for producing the protein. Besides, the present invention relates to a reagent kit comprising at least one selected from a DNA represented by the base sequence described by SEQ ID NO: 1 of the sequence listing and a homolog of the DNA, a recombinant vector containing any one DNA selected from the DNA and a homolog of the DNA, a transformant in which the recombinant vector is introduced, a protein encoded by the DNA, and an antibody recognizing the protein. Further, the present invention relates to an agent for improving depression state comprising a compound that inhibits the function and/or expression of any one protein selected from the group consisting of a protein encoded by a DNA represented by the base sequence described in SEQ ID NO: 1 of the sequence listing and a homolog of the protein. Besides, the present invention relates to a method for improving depression state comprising inhibiting the function and/or expression of any one protein selected from the group consisting of a protein encoded by a DNA represented by the base sequence described in SEQ ID NO: 1 of the sequence listing and a homolog of the protein. Further, the present invention relates to an agent for preventing and/or treating depression comprising an effective amount of the agent for improving the depression state. Further, the present invention relates to a method for preventing and/or treating depression comprising using the agent for improving the depression state and the method for improving the depression state. Besides, the present invention relates to a method for quantitatively or qualitatively assaying a DNA represented by the base sequence described in SEQ ID NO: 1 and a homolog of the DNA, or the complementary strand thereof, or a protein encoded by the DNA. Further, the present invention relates to an assay method for use in diagnosing depression or a method for diagnosing depression, comprising performing quantitative or qualitative analysis with employing a DNA selected from the group consisting of a DNA represented by a base sequence described in SEQ ID NO: 1 of the sequence listing and a homolog of the DNA, and/or, the protein encoded by the DNA, as a marker

BACKGROUND ART

The membrane protein receptor is a protein that has a domain for penetrating the lipid double layer of a biological membrane to be present in a cell membrane, and specifically recognizes various physiological active substances to transmit and express their actions. The physiological active substance specifically binding to the membrane protein receptor is generally referred to as a ligand. The ligand is exemplified by a peptide hormone, a neurotransmitter, a growth factor and the like. The binding of the ligand to the membrane protein receptor causes a cell response via formation of second messenger, change in intracellular ion concentration, phosphorylation of proteins and the like. A series of reactions involving in changes such as formation of second messenger in cells, change in intracellular ion concentration and phosphorylation of proteins by binding of a ligand to the membrane protein receptor are generally referred to as a signal transduction, and a process for the series of reactions is referred to as a signal transduction pathway.

G-protein coupled receptor (hereunder, may be abbreviated as GPCR) is a glycoprotein that is present in cell membrane that is one kind of seven-span transmembrane receptor that has the structural characteristic of having seven cell membrane spanning domains, and it constitutes a super family with a many members. One thousand or more GPCR genes have already been identified, and studies are proceeding in relation to the three dimensional structure of GPCR, lignads for GPCR, intracellular signal transduction pathways through GPCR, and the functions thereof and the like.

GPCR is a receptor for light, odor and flavor and, at the same time, is also a hormone and neurotransmitter receptor and serves as an important sensor of cells in living organisms ranging from yeasts to humans.

When GPCR receives stimulation from a ligand it binds with G protein that is present inside the cell. G protein is a protein that couples with GPCR and has a function as a signal transduction factor. G protein is broadly classified into a several kinds of families based on functions to various factors (hereunder, referred to as "effector") involved in signal transduction in the intracellular signal transduction pathways and difference in the genes encoding the protein. The G proteins that belong to each family are trimers comprising three subunits called α, β and γ, and normally guanosine 5'-diphosphate (GDP) is bound specifically to α-subunit. GDP-bound G protein is an inactive form that does not exhibit an action to an effector. When GPCR is stimulated by a ligand, an exchange reaction occurs between GDP binding to G protein and guanosine 5'-triphosphate (GTP) present in the cell, whereby the GDP is released from G protein and G protein then binds to GTP to form GTP-bound G protein. GTP-bound G protein is referred to as an active form, and it rapidly dissociates into α-subunit bound with GTP (αGTP) and a dimer (βγ) comprising β- and γ-subunits. αGTP and βγ directly act on an effector (for example, a calcium ion channel or a potassium ion channel) to activate the intracellular signal transduction pathway, and as a result, induce various cellular responses.

Amongst the GPCR superfamily, human brain angiogenesis inhibitor 2 (hereunder, abbreviated as hBAI2) is classified into class B (secretin like) and its gene is registered in GenBank under accession number AB 005298.

Although a report (Non-Patent Literature 1) exists relating to the sequence information and expression distribution of hBAI2, neither the function of hBAI2 nor its involvement in disease has been reported. However, based on a structural comparison with BAI1, a homolog of BAI2, it is considered that thrombospondin type I domain (hereunder referred to as "TSP-I domain") is present in the extracellular domain (Non-Patent Literature 2). TSP-I domain is a characteristic domain recognized in a region comprising the amino acid sequence from position 385 to position 522 in thrombospondin, and it is known to be involved in the extracellular matrix of thrombospondin and as an important function domain for angiogenesis inhibiting ability.

Regarding hBAI1, it has been reported that its expression is specifically high in human brain tissue, that a domain having angiogenesis inhibitory ability is present in the extracellular region, that there is a possibility that it is subject to expression control by p53 and the like, suggesting the possibility that this gene is involved in some way in a mechanism relating to angiogenesis in the brain (Non-Patent Literature 1-4).

Regarding mouse BAI2 that is a gene associated with hBAI2, it is reported that a negative correlation is observed in the expression amount between BAI2 and vascular endothelial growth factor (VEGF) in brain tissue of cerebral ischemia model rat, and it is considered that, similarly to hBAI1, mouse BAI2 may be involved in angiogenesis. Specifically, expression of BAI2 was decreased after suffering the hypoxic state which was followed by increase of expression of VEGF. Further, a splicing variant of mouse BAI2 is reported to exist (non-patent document 3).

Even though it is predicted from the sequence information that both hBAI1 and hBAI2 belong to the GPCR family, no report can be found that mentions their functions as GPCR, including information regarding a ligand.

Meanwhile, cholecystokinin (hereunder, abbreviated as "CCK") is known as a gastrointestinal hormone released from endocrine cell in duodenal mucous membrane. CCK is secreted accompanying intake of fat, and promotes gallbladder contraction and pancreatic enzyme secretion. It exhibits actions in the digestive organs including gallbladder contraction, promotion of pancreatic enzyme secretion and stimulation of intestinal movement. CCK is also considered a signaling substance that imparts a sensation of satiety to cerebral neurons.

CCK is known to be sulfated at the seventh tyrosine residue from the C-terminal side. By post-translational processing of CCK, fragments of several lengths that have different cleavage sites on the N-terminal side, such as CCK-4, CCK-8, CCK-12, CCK-33 and CCK-58, are produced. It has been verified that the physiological activity and amount of each of these fragments are different. Further, cerulein that is extracted from the skin of frog has been reported as a compound that has a similar chemical structure to CCK and which exhibits the same biological activity.

CCK is widely distributed in the brain and, for example, it has been observed in large amounts in brain cortex, hippocampus, amygdaloid body, and hypothalamus, and its action in the central nerves, such as involvement in anxiety, analgesia, sedation, food intake control, memory and learning is also reported. CCK is partially co-localized with DA (Dopamine) and GABA (γ-aminobutyric acid), and its interaction with 5HT (serotonin; 5-hydroxytryptamine)-functioned nervous system and the like has also been reported. It has also been reported that release of CCK is regulated by GABA. CCK-8 and CCK-4 have mainly been reported as CCK exhibiting bioactivity that is present in the brain. CCK-8 that is present in the brain is a cholecystokinin octapeptide sulfated form (CCK-8S) in which the seventh tyrosine residue from the C-terminal side is sulfated.

Recently, it has been reported that CCK is essential for memory retention. For example, it has been clarified that absence of CCK-8S makes it difficult to recall memory to conscious level and translate it into action, and that CCK-4 (a C-terminal tetrapeptide of CCK-33) obstructs mnemonic retrieval.

CCK-A receptor and CCK-B receptor have been reported as CCK receptors. These are both G-protein coupled receptors. Expression of CCK-A receptor is detected in tissues and cells originating in the alimentary canal, and in leukocytes and the like in the blood. CCK-A receptor is involved in alimentary regulation in the intracellular signal transduction pathway, for example, through promotion of effectors such as phospholipase C and adenyl cyclase. Meanwhile, expression of CCK-B receptor is detected in tissues and cells originating in the brain and alimentary canal, and in leukocytes and the like in the blood. CCK-B receptor is also referred to as "gastrin receptor", and is involved in alimentary regulation and cell proliferation in the intracellular signal transduction pathway, for example, through promotion of effectors such as phospholipase C and intracellular calcium ion influx. In recent years, attention is being focused on the relation between CCK-B receptor and anxiety.

Non-Patent Literature 1: Shiratsuchi, T. et al., "Cytogenetics and cell genetics", 1997, Vol. 79, p. 103-108.

Non-Patent Literature 2: Nishimori, H. et al., "Oncogene", 1997, Vol. 15, p. 2145-2150.

Non-Patent Literature 3: Kee, H. J. et al., "Journal of Cerebral Blood Flow and Metabolism", 2002, Vol. 22, p. 1054-1067.

Non-Patent Literature 4: Kaur, B. et al., "American Journal of Pathology", 2003, Vol. 162, p. 19-27.

DISCLOSURE OF THE INVENTION

GPCR serves as an important sensor of cells in vivo, and is a leading target molecule in the developing remedies for various diseases. Although a large number of GPCRs have already been found, identification of a novel GPCR can be expected to make a large contribution in the field of pharmaceutical development.

An object of the present invention is to provide a gene encoding a novel protein having an equivalent function to GPCR and the protein. Further, another object of the present invention is to provide a method for producing the protein. Furthermore, the other object of the present invention is to provide a recombinant vector containing the gene and a transformant in which the recombinant vector is introduced. A still further object of the present invention is to provide an antibody against the protein. A further object of the present invention is to provide a means for identifying a compound that inhibits or promotes the function of the protein. Further, the other object of the present invention is to find out a relation of the gene and protein to a disease, and to provide an effective means for prevention and/or treatment of the disease. That is, a still further object of the present invention is to provide a medicinal composition that can be used for a disease caused by an abnormality in the function of the protein and/or the expression of the gene encoding the protein, as well as a method for diagnosing the disease and an assay method and a reagent kit for diagnosing the disease. Furthermore, the other object of the present invention is to provide a method for identifying a compound for use in prevention and/or treatment of the disease.

The present inventors conducted concentrated studies to solve the above problems and found a protein that works as a functional membrane protein receptor having a seven-span transmembrane domain and can be considered to be a GPCR as well as a gene encoding the protein, and succeeded in acquiring the gene product thereof using the gene. The present inventors demonstrated that the protein was expressed on cell membrane in animal cells that was transfected with the gene, and that a cell response was produced by ligand stimulation through intracellular signal transduction. It was also clarified that the protein interacted with a protein involved in intracellular signal transduction in the C-terminal region thereof, and also that it had three TSP-I domains that were known to be associated with an angiogenesis inhibiting function in its amino acid sequence. Further, it was demonstrated that CCK-8S acted as a ligand of the functional membrane protein receptor.

In addition, the present inventors also found out a splicing variant of the gene. Then, it was demonstrated in the present invention that a protein encoded by the splicing variant of the gene was expressed on a cell membrane of an animal cell as a protein encoded by the gene did, and caused a cell response by the ligand stimulation through an intracellular signal transduction.

Further, the present invention demonstrated that an experimental system, in which an animal cell expressing the gene was stimulated by the ligand to cause a cell response, can be used to identify a compound that inhibits the function of a protein encoded by the gene, i.e., the cell response.

Further, the present inventors discovered that the gene is strongly expressed in the brain tissues, particularly in brain cortex, hippocampus, and amygdaloid body. Further, it has discovered that the gene and a splicing variant thereof are involved in depression.

The present invention was achieved base on these findings.

Thus, the present invention relates to a DNA selected from the group consisting of:

(i) a DNA consisting of a base sequence represented by SEQ ID NO: 1 of the sequence listing or a complementary strand thereof;

(ii) a DNA containing the DNA of (i) or a complementary strand thereof;

(iii) a DNA having homology of at least 70% with the base sequence of the DNA of (i) or (ii) and encoding a protein having an equivalent function to a G-protein coupled receptor, or a complementary strand thereof;

(iv) a DNA comprising a base sequence having a variation including a deletion, a substitution and an addition of one to several nucleotides in the base sequence of the DNA according to any one of (i) to (iii) and encoding a protein having an equivalent function to a G-protein coupled receptor, or a complementary strand thereof; and (v) a DNA hybridizing under stringent conditions with the DNA according to any one of (i) to (iv) and encoding a protein having an equivalent function to a G-protein coupled receptor, or a complementary strand thereof.

The present invention also relates to a DNA consisting of a partial base sequence of the aforementioned DNA.

The present invention further relates to a DNA represented by the base sequence described in SEQ ID NO: 15 of the sequence listing or a complementary strand thereof.

The present invention still further relates to a DNA represented by the base sequence described in SEQ ID NO: 17 of the sequence listing or a complementary strand thereof.

The present invention also relates to the aforementioned DNA, wherein the equivalent function to a G-protein coupled receptor is an equivalent function to a G-protein coupled receptor that is caused by binding with a ligand, which is a peptide selected from the group consisting of:

(i) cholecystokinin octapeptide sulfated form (SEQ ID NO: 14, hereunder abbreviated as "CCK-8S");
(ii) a peptide comprising an amino acid sequence having a variation including a deletion, a substitution and an addition of one to several amino acids in the amino acid sequence of CCK-8S, and an equivalent function to CCK-8S; and
(iii) a peptide containing the peptide according to (i) or (ii) and having an equivalent function to CCK-8S.

The present invention further relates to a recombinant vector containing any one of the aforementioned DNAs or the complementary strand thereof.

The present invention still further relates to a transformant that was introduced with a recombinant vector that contains any one of the aforementioned DNAs.

The present invention also relates to a cell line deposited under accession number FERM BP-10101.

The present invention further relates to a protein encoded by any one of the aforementioned DNAs.

The present invention still further relates to a protein selected from the group consisting of:
(i) a protein consisting of an amino acid sequence represented by SEQ ID NO: 2 of the sequence listing;
(ii) a protein containing the protein of (i);
(iii) a protein having homology of at least 70% with the amino acid sequence of the protein of (i) or (ii) and having an equivalent function to a G-protein coupled receptor; and
(iv) a protein comprising an amino acid sequence having a variation including a deletion, a substitution and an addition of one to several amino acids in the amino acid sequence of the protein according to any one of (i) to (iii), and having an equivalent function to a G-protein coupled receptor.

The present invention also relates to a protein consisting of a partial sequence of an amino acid sequence represented by SEQ ID NO: 2 of the sequence listing.

The present invention further relates to a protein represented by the amino acid sequence described in SEQ ID NO: 16 of the sequence listing.

The present invention still further relates to a protein represented by the amino acid sequence described in SEQ ID NO: 18 of the sequence listing.

The present invention also relates to any one of the aforementioned proteins, which has an angiogenesis inhibiting function.

The present invention further relates to any one of the aforementioned proteins, which has a function that interacts with a protein having guanylate kinase activity and/or a protein having an intercellular adhesion.

The present invention still further relates to a protein having an equivalent function to a G-protein coupled receptor, a function that interacts with a protein having an intercellular adhesion function and/or a protein having guanylate kinase activity, and an angiogenesis inhibiting function, wherein the protein is selected from the group consisting of:
(i) a protein consisting of an amino acid sequence represented by SEQ ID NO: 2 of the sequence listing;
(ii) a protein containing the protein of (i);
(iii) a protein having homology of at least 70% with the amino acid sequence of the protein of (i) or (ii); and
(iv) a protein comprising an amino acid sequence having a variation including a deletion, a substitution or an addition of one to several amino acids in the amino acid sequence of the protein according to any one of (i) to (iii).

The present invention also relates to the aforementioned protein, which has a function that generates a change in a cell membrane potential when a ligand is bound to the protein on a cell.

The present invention further relates to the aforementioned protein, which has a function that increases an intracellular calcium concentration when a ligand is bound to the protein on a cell.

The present invention still further relates to the aforementioned protein, wherein the equivalent function to a G-protein coupled receptor is an equivalent function to a G-protein coupled receptor that is caused by binding with a ligand, which is a peptide selected from the group consisting of:
(i) cholecystokinin octapeptide sulfated form (SEQ ID NO: 14, hereunder abbreviated as "CCK-8S");
(ii) a peptide comprising an amino acid sequence having a variation including a deletion, a substitution and an addition of one to several amino acids in the amino acid sequence of CCK-8S, and having an equivalent function to CCK-8S; and
(iii) a peptide including the peptide according to (i) or (ii) and having an equivalent function to CCK-8S.

The present invention also relates to a method for producing a protein encoded by any one of the aforementioned DNAs, comprising culturing the transformant that was introduced with the recombinant expression vector containing the DNA.

The present invention further relates to an antibody that immunologically recognizes a protein encoded by any one of the aforementioned DNAs.

The present invention still further relates to a method of identifying a ligand or an agonist of a protein encoded by any one of the aforementioned DNAs, comprising contacting the protein with a test compound or a test substance.

The present invention also relates to the aforementioned identification method, wherein contacting the protein with a test compound or a test substance is conducted by contacting a protein that is expressed on a cell membrane of a transformant that was introduced with the recombinant expression vector containing the DNA or of a cell line deposited under accession number FERM BP-10101 with a test compound or a test substance.

The present invention further relates to the aforementioned identification method, wherein contacting the protein with a test compound or a test substance is conducted by contacting a transformant that was introduced with the recombinant expression vector containing the DNA or a cell line deposited under accession number FERM BP-10101 with a test compound or a test substance under conditions that enable interaction between the transformant or the cell line and the test compound or the test substance; introducing a system that measures a function of a protein that is expressed on a cell membrane of the cell line or the transformant; and selecting a test compound or a test substance that changes the function in comparison to a case in which the test compound or the test substance is not contacted with the protein.

The present invention still further relates to the aforementioned identification method, wherein contacting the protein with a test compound or a test substance is conducted by contacting a protein that is expressed on a cell membrane of a transformant that was introduced with the recombinant expression vector containing the DNA or of a cell line deposited under accession number FERM BP-10101 with a test compound or a test substance, and then determination of a intracellular calcium concentration of the transformant or the cell line is conducted to select a test compound or a test substance that increases the intracellular calcium concentration in comparison to a case in which the test compound or the test substance is not contacted with the protein.

The present invention also relates to the aforementioned identification method, wherein contacting the protein with a test compound or a test substance is conducted by contacting a protein that is expressed on a cell membrane of a transformant that was introduced with the recombinant expression vector containing the DNA or of a cell line deposited under accession number FERM BP-10101 with a test compound or a test substance, and then determination of a cell membrane potential of the transformant or the cell line is conducted to select a test compound or a test substance that changes the cell membrane potential in comparison to a case in which the test compound or the test substance is not contacted with the protein.

The present invention further relates to the aforementioned identification method, wherein contacting the protein with a test compound or a test substance is conducted by contacting a protein that is expressed on a cell membrane of a transformant that was introduced with the recombinant expression vector containing the DNA or of a cell line deposited under accession number FERM BP-10101 with a test compound or a test substance, and then determination of a cell membrane potential of the transformant or the cell line to select a test compound or a test substance that generates a current variation that is distinctive of a G-protein coupled receptor in comparison to a case in which the test compound or the test substance is not contacted with the protein.

The present invention still further relates to a method of identifying a compound that inhibits or promotes the binding of a protein encoded by any one of the aforementioned DNAs with a ligand, a function of the protein, and/or an expression of the DNA, comprising using at least one selected from the DNA, a recombinant vector or recombinant expression vector containing the DNA, a transformant that was introduced with the recombinant vector or recombinant expression vector, a cell line deposited under accession number FERM BP-10101, a protein encoded by the DNA, and an antibody recognizing the protein.

The present invention also relates to the aforementioned identification method, wherein the ligand is a peptide selected from the group consisting of:
(i) cholecystokinin octapeptide sulfated form (SEQ ID NO: 14, hereunder abbreviated as "CCK-8S");
(ii) a peptide comprising an amino acid sequence having a variation including a deletion, a substitution and an addition of one to several amino acids in the amino acid sequence of CCK-8S, and having an equivalent function to CCK-8S; and
(iii) a peptide containing the peptide according to (i) or (ii) and having an equivalent function to CCK-8S.

The present invention further relates to a method of identifying a compound that inhibits or promotes a function of a protein encoded by any one of the aforementioned DNAs, comprising allowing a transformant that was introduced with a recombinant vector or recombinant expression vector that contains the DNA or a cell line deposited under accession number FERM BP-10101 to coexist with a test compound under conditions that enables interaction of the transformant or the cell line with the test compound, introducing a system that measures a function of the protein that is expressed on a cell membrane of the transformant or the cell line, and determining whether or not the test compound inhibits or promotes the function of the protein by detecting the existence or non-existence of, or a change in, the function of the protein.

The present invention still further relates to the aforementioned identification method, wherein the system that measures a function of the protein that is expressed on a cell membrane of the transformant or the cell line is a system that measures a change in an intracellular calcium concentration produced by addition of a ligand, and detecting the existence or non-existence of, or a change in, the function of the protein is conducted by detecting a change in an intracellular calcium concentration.

The present invention also relates to the aforementioned identification method, wherein the system that measures a function of the protein that is expressed on a cell membrane of the transformant or the cell line is a system that measures a change in a membrane potential produced by addition of a ligand, and detecting the existence or non-existence of, or a change in, the function of the protein is conducted by detecting a change in a membrane potential.

The present invention further relates to the aforementioned identification method, wherein the system that measures a function of the protein that is expressed on a cell membrane of the transformant or the cell line is a system that measures a function of the protein caused by a ligand which is a peptide selected from the group consisting of:
(i) cholecystokinin octapeptide sulfated form (SEQ ID NO: 14, hereunder abbreviated as "CCK-8S");
(ii) a peptide comprising an amino acid sequence having a variation including a deletion, a substitution and an addition of one to several amino acids in the amino acid sequence of CCK-8S, and having an equivalent function to CCK-8S; and
(iii) a peptide containing the peptide according to (i) or (ii) and having an equivalent function to CCK-8S.

The present invention still further relates to a method for identifying a compound that has an anti-depressant action, comprising using at least one selected from the following: the aforementioned DNA; a protein encoded by the DNA; and a cell containing the DNA.

The present invention further relates to a the aforementioned identifying method, comprising contacting a cell containing a DNA represented by any one of base sequences described in SEQ ID NO: 1, 15, 17, 19 and 21 of the sequence listing with a test compound, measuring a function of a protein encoded by the DNA and expressed on a cell membrane of the cell, and determining by comparing with a case where the cell is not made to contact with the test compound that the test compound which reduces or eliminates the function of the protein is to be a compound having anti-depressant action.

The present invention still further relates to the aforementioned identifying method, wherein the function of a protein encoded by a DNA expressed on a cell membrane of a cell is a function causing an increase in intracellular calcium concentration in response to addition of a ligand of the protein or a function causing a change in membrane potential in response to addition of a ligand of the protein.

The present invention also relates to the aforementioned identifying method, wherein the ligand used therein is a peptide selected from the group consisting of:
(i) cholecystokinin octapeptide sulfated form (SEQ ID NO: 14, hereunder referred to as CCK-8S),
(ii) a peptide having mutations such as deletion, substitution, or addition of one to several amino acids in amino acid sequence of CCK-8S and having an equivalent function to CCK-8S; and
(iii) a peptide containing the amino acid sequence of the peptide described in (i) or (ii) and having an equivalent function to CCK-8S.

The present invention further relates to a pharmaceutical composition comprising an effective dose of at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein as an active ingredient.

The present invention still further relates to an agent for preventing and/or treating a disease attributable to a decrease of cholecystokinin octapeptide sulfated form (SEQ ID NO: 14) and/or a reduction in a function thereof, comprising an effective dose of an agonist of a protein encoded by any one of the aforementioned DNAs as an active ingredient.

The present invention also relates to the aforementioned agent for preventing and/or treating a disease, wherein the disease is a disease selected from dementia (including Alzheimer's disease), anxiety disorder, obesity and diabetes.

The present invention further relates to an agent for preventing and/or treating a disease associated with angiogenesis, comprising an effective dose of at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein as an active ingredient.

The present invention still further relates to an agent for preventing and/or treating tumor disease, comprising an effective dose of at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein as an active ingredient.

The present invention also relates to a method for preventing and/or treating a disease attributable to a decrease of cholecystokinin octapeptide sulfated form (SEQ ID NO: 14) and/or a reduction in a function thereof, comprising using an agonist of a protein encoded by any one of the aforementioned DNAs.

The present invention further relates to the aforementioned method for preventing and/or treating a disease, wherein the disease is a disease selected from dementia (including Alzheimer's disease), anxiety disorder, obesity and diabetes.

The present invention still further relates to a method for preventing and/or treating a disease associated with angiogenesis, comprising using at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein.

The present invention also relates to a method for preventing and/or treating a tumor disease, comprising using at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein.

The present invention further relates to a method for improving depression state, comprising inhibiting the function and/or expression of any one protein selected from the group consisting of a protein encoded by the aforementioned DNAs.

The present invention still further relates to a method for preventing and/or treating depression, comprising using the aforementioned method for improving depression state.

The present invention also relates to a method for quantitatively or qualitatively assaying any one of the aforementioned DNAs or a protein encoded by the DNA, comprising using at least one selected from the DNA, a recombinant vector or recombinant expression vector containing the DNA, a transformant that was introduced with the recombinant vector or recombinant expression vector, a protein encoded by the DNA, and an antibody recognizing the protein.

The present invention further relates to an assay method for use in diagnosing a disease attributable to an abnormality in any one of the aforementioned DNAs, or a protein encoded by the DNA, comprising performing quantitative or qualitative analysis with employing the DNA and/or the protein as a marker.

The present invention still further relates to a method for diagnosing a disease attributable to an abnormality in any one of the aforementioned DNAs, or a protein encoded by the DNA, comprising using at least one selected from the DNA, a recombinant vector or recombinant expression vector containing the DNA, a transformant that was introduced with the recombinant vector or recombinant expression vector, a protein encoded by the DNA, and an antibody recognizing the protein.

The present invention also relates to a method for diagnosing a disease associated with angiogenesis, comprising using at least one selected from any one of the aforementioned DNAs, a recombinant vector or recombinant expression vector containing the DNA, a transformant that was introduced with the recombinant vector or recombinant expression vector, a protein encoded by the DNA, and an antibody recognizing the protein.

The present invention further relates to the aforementioned diagnosing method, wherein the disease associated with angiogenesis is cerebral infarction and/or cerebral contusion.

The present invention still further relates to an assay method for use in diagnosing depression, comprising performing quantitative or qualitative analysis with employing the aforementioned DNAs, and/or, the protein encoded by the DNA, as a marker.

The present invention also relates to a method for diagnosing depression, comprising performing quantitative or qualitative analysis with employing the aforementioned DNAs, and/or, the protein encoded by the DNA, as a marker.

The present invention further relates to a reagent kit comprising at least one selected from the following: any one of the aforementioned DNAs, a recombinant vector or recombinant expression vector containing the DNA, a transformant that was introduced with the recombinant vector or recombinant expression vector, a cell line deposited under accession number FERM BP-10101, a protein encoded by the DNA, and an antibody recognizing the protein.

The present invention still further relates to a reagent kit comprising at least one selected from the following: a DNA represented by any one of base sequences described in SEQ ID NO: 1, 15 and 17 of the sequence listing, and the protein encoded by the DNA is a protein represented by any one of amino acid sequences described in SEQ ID NO: 2, 16 and 18 of the sequence listing.

The present invention also relates to a diagnostic kit for a disease associated with angiogenesis, comprising at least one selected from any one of the aforementioned DNAs, a recombinant vector or recombinant expression vector containing the DNA, a transformant that was introduced with the recombinant vector or recombinant expression vector, a cell line deposited under accession number FERM BP-10101, a protein encoded by the DNA, and an antibody recognizing the protein.

The present invention further relates to the aforementioned diagnostic kit, wherein the disease associated with angiogenesis is cerebral infarction and/or cerebral contusion.

According to the present invention, a protein that works as a functional membrane protein receptor having a seven-span transmembrane domain which is considered to be a GPCR and a DNA encoding the protein can be provided. Since this protein has three TSP-I domains, it is thought to be involved in angiogenesis inhibition. Further, since the protein interacts with a MAGUK (membrane-associated guanylate kinase homolog) family protein (protein having guanylate kinase activity and an intercellular adhesion function) in the C-terminal region thereof, the protein may be involved in the intercellular adhesion function of cells.

The protein is expressed on a cell membrane when it is expressed in a cell, and activates an intracellular signal transduction by ligand stimulation to cause a cell response.

It was also found in the present invention that CCK-8S may act as a ligand of the functional membrane protein receptor of the present invention. Since CCK-8S induced a biological response through the functional membrane protein receptor of the present invention at the low concentration of 1 nM, it is considered that CCK-8S is an in vivo ligand of the functional membrane protein receptor. It is reported that CCK-8S is essential for memory retention, for example, that absence of CCK-8S makes it difficult to recall memory to the conscious level and translate it into action. It is considered that the action of CCK-8S with respect to this kind of neurologic function occurs through the functional membrane protein receptor of the present invention. It is therefore considered that an agonist of the functional membrane protein receptor of the present invention has an action that is equivalent to that of CCK-8S, i.e. an action that modifies a neurologic function such as memory and the like.

Thus, according to the present invention, it is possible to carry out the elucidation of the signal transduction pathway and the cellular function both of which the present protein participates in as well as the regulation thereof.

Further, according to the present invention, it is possible to identify and acquire an agonist of a functional membrane protein receptor on which CCK-8S acts. It is also possible to modify the neurologic function using the agonist. For example, it is possible to retain memory using the agonist. Further, it is possible to alleviate a disease or symptoms accompanying hindrance of neurologic function using the agonist.

Thus, according to the present invention, it is possible to diagnose, prevent and/or treat a disease caused by an abnormality in the protein and/or DNA, for example, a disease associated with angiogenesis. Specific examples of this type of disease include cerebral infarction, cerebral contusion and tumor disease. Further, since the protein is a functional membrane protein receptor, it is also possible to diagnose, prevent and/or treat a disease caused by a decline or disappearance or the like in the function and/or amount of a ligand thereof, for example, CCK-8S. Examples of this kind of disease include a disease accompanying damage to the neurologic function of memory or the like, and specific examples thereof include Alzheimer's disease. Moreover, the present invention allows for the prevention and/or treatment of a disease attributable to an abnormality in the present protein and/or DNA, for example, depression.

BRIEF DESCRIPTION OF THE DRAWINGS

FIG. 1-A is a schematic diagram illustrating a comparison between a function domain of a protein represented by the amino acid sequence described in SEQ ID NO: 2 and a protein encoded by hBAI2. (Example 1)

FIG. 1-B is a schematic diagram illustrating a comparison between a structural characteristic of a protein represented by the amino acid sequence described in SEQ ID NO: 2 and a splicing variant thereof. The term "ph01207" means a protein represented by the amino acid sequence described in SEQ ID NO: 2. The terms "7tmHR", "hk01941" and "variant 3" each indicate a splicing variant of a protein represented by the amino acid sequence described in SEQ ID NO: 2. (Example 6)

FIG. 1-C is a view showing a comparison between an amino acid sequence of a protein represented by the amino acid sequence described in SEQ ID NO: 2 and a splicing variant thereof. In the figure, the thrombospondin type I domain (TSP-I domain) was double underlined, and the transmembrane domain was underlined. The term "ph01207" means a protein represented by the amino acid sequence described in SEQ ID NO: 2. The terms "7tmHR", "hk01941" and "variant 3" each indicate a splicing variant of a protein represented by the amino acid sequence described in SEQ ID NO: 2. (Example 6)

FIG. 2 is a view showing that, when cDNA clone ph01207 was expressed in CHO-K1 cells, an animal cell line, as a FLAG-tag fusion protein and a HA-tag fusion protein, respectively, these proteins expressed on the cell membrane (the left panel and right panel, respectively). Detection of the protein on the cell membrane was analyzed by fluorocytometry using anti-FLAG-tag antibody, anti-HA-tag antibody and an FITC-labeled second antibody (FITC-anti-mouse IgG antibody). In the figure, the region shown in black indicates cells that expressed each tag fusion protein and the region shown in white indicates control cells that did not express the proteins. (Example 2)

FIG. 3 is a view illustrating waveforms that can be observed when the ligand response of GPCR is measured by variations in membrane potential of cells (waveform produced by GPCR-specific response (waveform 1), waveforms produced by artificial elements and the like (waveform 2-4), and waveforms recognized at the time of no response (waveforms 5 and 6)). (Example 3)

FIG. 4-A is a view showing that intracellular $Ca^{2+}$ concentration increased with addition of 1 nM CCK-8S (SEQ ID NO: 14) in CHO-K1 cell line (HA-ph01207#10-6) stably expressing cDNA clone ph01207 as a HA-tag fusion protein. In contrast, in CHO-K1 cell line that was not transfected with this cDNA, an increase in intracellular $Ca^{2+}$ concentration with addition of CCK-8S (SEQ ID NO: 14) was not observed. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 5)

FIG. 4-B is a view showing that an increase in intracellular $Ca^{2+}$ concentration with addition of 1 nM CCK-8NS(CCK-8 Nonsulfated form) was not observed in CHO-K1 cell line (HA-ph01207#10-6) stably expressing cDNA clone ph01207 as a HA-tag fusion protein. Although CCK-8NS is a CCK octapeptide consisting of the same amino acid sequence as CCK-8S, it is a peptide in which the seventh tyrosine residue from the C-terminus is not sulfated. An increase in intracellular $Ca^{2+}$ concentration with addition of CCK-8NS was also not observed in a CHO-K1 cell line that was not transfected with cDNA clone ph01207. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 5)

FIG. 4-C is a view showing that an increase in intracellular $Ca^{2+}$ concentration with addition of 1 nM CCK-4 was not observed in CHO-K1 cell line (HA-ph01207#10-6) stably expressing cDNA clone ph01207 as a HA-tag fusion protein. An increase in intracellular $Ca^{2+}$ concentration with addition of CCK-4 was also not observed in CHO-K1 cell line that was not transfected with the cDNA. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 5)

FIG. 4-D is a view showing that intracellular $Ca^{2+}$ concentration increased with addition of 10 μM calcium ionophore A23187 in CHO-K1 cell line (HA-ph01207#10-6) stably expressing cDNA clone ph01207 as a HA-tag fusion protein. An increase in intracellular $Ca^{2+}$ concentration with addition of A23187 was also observed in CHO-K1 cell line that was not transfected with the cDNA. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 5)

FIG. 4-E is a view showing intracellular $Ca^{2+}$ concentrations after addition of a buffer in CHO-K1 cell line (HA-ph01207#10-6) stably expressing cDNA clone ph01207 as a HA-tag fusion protein and CHO-K1 cell line that was not transfected with the cDNA. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 5)

FIG. 5-A is a view showing typical results of increase in intracellular $Ca^{2+}$ concentration by 1 nM CCK-8S (SEQ ID NO: 14) in 7tmHR stably expressing cell line. Increase in intracellular $Ca^{2+}$ concentration by CCK-8S (SEQ ID NO: 14) was not observed in the host cell to which 7tmHR expression vector was not transfected. In the figure, the term "7tmHR/CHO#6" refers to 1 clone of 7tmHR stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 8)

FIG. 5-B is a view showing an increase in intracellular $Ca^{2+}$ concentration by 20 μM calcium ionophore A23187 in 7tmHR stably expressing cell line. An increase in intracellular $Ca^{2+}$ concentration by A23187 was observed even in the host cell to which 7tmHR expression vector was not transfected. In the figure, the term "7tmHR/CHO#6" refers to 1 clone of 7tmHR stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 8)

FIG. 6-A is a view showing typical results of increase in intracellular $Ca^{2+}$ concentration by 1 nM CCK-8S (SEQ ID NO: 14) in hk01941 stably expressing cell line. Increase in intracellular $Ca^{2+}$ concentration by CCK-8S (SEQ ID NO: 14) was not observed in the host cell to which hk01941 expression vector was not transfected. In the figure, the term "hk01941/CHO #13" refers to 1 clone of hk01941 stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 8)

FIG. 6-B is a view showing an increase in intracellular $Ca^{2+}$ concentration by 20 μM calcium ionophore A23187 in hk01941 stably expressing cell line. An increase in intracellular $Ca^{2+}$ concentration by A23187 was observed even in the host cell to which hk01941 expression vector was not transfected. In the figure, the term "hk01941/CHO#13" refers to 1 clone of hk01941 stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 8)

FIG. 7-A is a view showing typical results of increase in intracellular $Ca^{2+}$ concentration by 1 nM CCK-8S (SEQ ID NO: 14) in variant 3 stably expressing cell line. Increase in intracellular $Ca^{2+}$ concentration by CCK-8S (SEQ ID NO: 14) was not observed in the host cell to which variant 3 expression vector was not transfected. In the figure, the term "variant 3/CHO#14-18" refers to 1 clone of variant 3 stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 9)

FIG. 7-B is a view showing an increase in intracellular $Ca^{2+}$ concentration by 20 μM calcium ionophore A23187 in variant 3 stably expressing cell line. An increase in intracellular $Ca^{2+}$ concentration by A23187 was observed even in the host cell to which variant 3 expression vector was not transfected. In the figure, the term "variant 3/CHO#14-18" refers to 1 clone of variant 3 stably expressing cell line, and the term "CHO-K1" refers to a host cell. The horizontal axis shows the time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 9)

FIG. 8-A is a view showing that ph01207 gene is strongly expressed in protoplasmic astrocyte in human amygdaloid body with data analyzed by tissue immunostaining using anti-human BAI2 polyclonal antibody. (Example 10)

FIG. 8-B is a view showing that ph01207 gene is strongly expressed in neuron and glia in amygdaloid body with data analyzed by tissue immunostaining using anti-human BAI2 polyclonal antibody. (Example 10)

FIG. 8-C is a view showing that ph01207 gene is strongly expressed in neuron in CA2 region in hippocampus with data analyzed by tissue immunostaining using anti-human BAI2 polyclonal antibody. (Example 10)

FIG. 8-D is a view showing that ph01207 gene is strongly expressed in neuron in CA1 region in hippocampus with data analyzed by tissue immunostaining using anti-human BAI2 polyclonal antibody. (Example 10)

FIG. 9-A is a view showing that, in hippocampus of an F1 hetero mutant mouse prepared using ES cell which was introduced with a targeting vector for targeting mouse BAI2 gene, LacZ-Neo gene contained in the targeting vector was strongly expressed, which was detected by LacZ expression analysis. This result indicates that LacZ-Neo fragment was inserted into target site of mouse BAI2 gene, namely the gene was destroyed, and that mouse BAI2 gene is expressed in hippocampus. (Example 11)

FIG. 9-B is a view showing that, in amygdaloid body of an F1 hetero mutant mouse prepared using ES cell which as introduced with a targeting vector for targeting mouse BAI2 gene, LacZ-Neo gene contained in the targeting vector was strongly expressed, which was detected by LacZ expression analysis. This result indicates that LacZ-Neo fragment was inserted into target site of mouse BAI2 gene, namely the gene was destroyed, and that mouse BAI2 gene is expressed in amygdaloid body. (Example 11)

FIG. 10 is a view showing immobility time of a BAI2 knockout mouse and a wild type mouse in the tail suspension test. In the figure, "+/+" refers to a wild type mouse and "−/−" refers to a BAI2 knockout mouse. The tail suspension test was carried out using 16 wild type mice and 10 BAI2 knockout mice. Results are expressed by average (sec)±standard deviation of immobility time of each mouse. In the figure, asterisk shows that a significant difference (P<0.05) was obtained in statistical processing using t-test. (Example 11)

FIG. 11-A is a view showing that, in CHO-K1 cell line in which cDNA clone ph01207 is stably expressed, increase in intracellular $Ca^{2+}$ concentration by 10 nM CCK-8S was inhibited by addition of 10 μg/mL compound A. As a control, the buffer was added instead of the compound A. The compound A or the buffer was added 15 sec after the start of measurement, and CCK-8S was added 35 sec after addition of the compound A or the buffer. The horizontal axis shows time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 12)

FIG. 11-B is a view showing that, in CHO-K1 cell line in which cDNA clone ph01207 is stably expressed, increase in intracellular $Ca^{2+}$ concentration by 10 nM CCK-8S is inhibited by addition of 10 μg/mL compound B. As a control, the buffer was added instead of the compound B. The compound B or the buffer was added 15 sec after the start of measurement, and CCK-8S was added 35 sec after addition of the compound B or the buffer. The horizontal axis shows time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 12)

FIG. 11-C is a view showing that in CHO-K1 cell line in which cDNA clone ph01207 is stably expressed, increase in intracellular $Ca^{2+}$ concentration by 10 nM CCK-8S is inhibited by addition of 10 μg/mL compound C. As a control, the buffer was added instead of the compound C.

The compound C or the buffer was added 15 sec after the start of measurement, and CCK-8S was added 35 sec after addition of the compound C or the buffer. The horizontal axis shows time (Time (sec)) from the start of measurement of intracellular $Ca^{2+}$ concentration. The longitudinal axis shows fluorescence intensity (RFU) of fluorescent dye that reflects $Ca^{2+}$ concentration. (Example 12)

DETAILED DESCRIPTION

In the present specification, the term "protein" is sometimes used as a generic term that refers to an isolated or synthetic full length protein, an isolated or synthetic full length polypeptide, or an isolated or synthetic full length oligopeptide. In this case, a protein, polypeptide or oligopeptide has a minimum size of two amino acids. Hereunder, one character or three characters may be used when representing an amino acid.

The present invention relates to a protein that works as a functional membrane protein receptor having a seven-span transmembrane domain, and a DNA encoding the protein. Specifically, the present invention relates to a protein that acts as a G protein coupled receptor, and a DNA encoding the protein.

As used herein, the phrase "membrane protein receptor" means a protein that is made of a protein having a domain for penetrating the lipid double layer of a biological membrane to be present in a cell membrane, and specifically recognizes various physiological active substances to transmit and express their actions. Here, the protein includes a glycoprotein. As used herein, the phrase "Functional membrane protein receptor" means a membrane protein receptor having a function that receives the action of a ligand to cause a cell response via intracellular signal transduction. The membrane protein receptor has an extracellular domain interacting with the ligand, a domain for penetrating the lipid double layer of biological membrane, and an intracellular domain for mediating intracellular signal transduction.

As used herein, the phrase "G-protein coupled receptor (GPCR)" means a membrane protein receptor that activates G-protein by binding to the G-protein present in cells when stimulated by a ligand. The term "G-protein" refers to a protein that associates with GPCR, converts from GDP-binding type G-protein to GTP-binding type G-protein due to GDP/GTP exchange reaction and causes various cell responses as an intracellular signal transduction factor. The phrase "activates G-protein" means that by inducing and/or promoting the GDP/GTP exchange reaction, the conversion from GDP-binding type G-protein to GTP-binding type G-protein is induced and/or promoted, thereby various cell responses in which the G-protein associated GPCR is involved is induced and/or promoted.

As used herein, the term "ligand" means a physiological active substance specifically interacting with a membrane protein receptor.

As used herein, the term "interaction" means, for example, that two homologous or distinct proteins specifically act with each other, and as a result the function of one or both of the proteins change, for example, enhance or decrease. The phrase "specifically act" means that the proteins participating in the action acts more selectively with each other than with the other proteins. The interaction, for example, includes binding of two distinct proteins, or activation of one protein by another protein.

As used herein, the phrase "intracellular signal transduction" means a series of reactions generating changes such as formation of second messenger in cells, change in intracellular ion concentration and phosphorylation of proteins by action of a ligand to the membrane protein receptor. The phrase "intracellular signal transduction pathway" means a process of the series of reactions.

A DNA used in the present invention is, specifically, a DNA represented by the base sequence described in SEQ ID NO: 1 or a DNA homolog of the DNA. In the present specification, the phrase "DNA homolog" means a DNA having sequence homology with the DNA of interest and encoding a protein which has a similarity with a protein encoded by the DNA in structural characteristic or biological function.

A protein used in the present invention is, preferably, a protein encoded by a DNA represented by the base sequence described in SEQ ID NO: 1 or a protein homolog of the protein.

In the present specification, the phrase "protein homolog" means a protein having sequence homology with the protein of interest and a similarity with the protein in structural characteristic or biological function.

In the present invention, a DNA and protein are preferably a DNA and protein that originate in human, but can be a DNA and protein that originate in a mammal, which have an equivalent function and a structural homology to a human-derived DNA and protein, for example, a DNA and protein that are originated in mouse, horse, sheep, cow, dog, monkey, cat, bear, rat or rabbit.

The DNA represented by the base sequence described in SEQ ID NO: 1 is a DNA that encodes a protein working as a functional membrane protein receptor having a seven-span transmembrane domain. A specific example of a protein encoded by the DNA represented by the base sequence described in SEQ ID NO: 1 is preferably a protein represented by the amino acid sequence described in SEQ ID NO: 2.

The protein encoded by the DNA represented by the base sequence described in SEQ ID NO: 1 has three TSP-I domains, one GPS (GPCR proteolytic site) domain and one seven-span transmembrane domain as the structural characteristics (see FIG. 1-A and FIG. 1-B). The seven-span transmembrane domain is also referred to as the GPCR family-2 domain and is a structure characteristic for a G-protein coupled receptor as GPS domain is. The TSP-I domain is a characteristic domain found in thrombospondin and is known to be an important functional domain involved in extracellular matrix of thrombospondin and antiangiogenic function thereof.

The gene product of the DNA represented by the base sequence described in SEQ ID NO: 1 exhibited actually a function as the membrane protein receptor. Specifically, it was observed in the animal cells in which the DNA represented by the base sequence described in SEQ ID NO: 1 was expressed, that the protein encoded by the DNA was expressed on the cell membrane, and that a cell response via intracellular signal transduction was caused by ligand stimulation such as CCK-8S (SEQ ID NO: 14) stimulation.

In addition, it was observed that the gene product of the DNA represented by the base sequence described in SEQ ID NO: 1 interacted with MAGUK family proteins DLG2, DLG3 and DLG4, or AIP1, MAGI3 and the like at C-terminal region thereof. MAGUK family proteins have a PDZ domain that recognizes the last C-terminal amino acid sequence of a target protein in protein interaction, and it is considered that by localizing on the cell membrane to interact with a membrane protein such as a receptor or an ion channel, the proteins participate in signal transduction from these membrane proteins to contribute to intercellular adhesion and the like. Interaction between hBAI2 and MAGUK family proteins has similarly been observed. Meanwhile, it has been reported that hBAI1, an hBAI2 homologue, binds with BAP1 (BAI1-associated protein 1), one of the MAGUK family proteins, through a partial sequence (QTEV: SEQ ID NO: 3) of the distal region of hBAI1 (Shiratsuchi, T. et al., "Biochemical and Biophysical Research Communications", 1998, Vol. 247, p. 597-604).

The amino acid sequence (QTEV) described in SEQ ID NO: 3 is conserved in the C-terminal region of both the protein encoded by the DNA represented by the base sequence described in SEQ ID NO: 1 and the protein encoded by hBAI2 (SEQ ID NO: 21). Therefore, the inventors consider that the both proteins interact with a protein having a PDZ domain in this sequence segment.

A DNA homolog of the DNA represented by the base sequence described in SEQ ID NO: 1 is preferably a DNA that has sequence homology to the DNA represented by the base sequence described in SEQ ID NO: 1 and encodes a protein that exhibits an equivalent function to GPCR by the action of CCK-8S (SEQ ID NO: 14).

The DNA homolog of the DNA represented by the base sequence described in SEQ ID NO: 1 is preferably exemplified by a splicing variant of the DNA represented by the base sequence described in SEQ ID NO: 1.

The protein having similarity with a protein encoded by the DNA represented by the base sequence described in SEQ ID NO: 1 in structural characteristic or biological function is preferably exemplified by a splicing variant of the protein encoded by the DNA represented by the base sequence described in SEQ ID NO: 1.

As used herein, the phrase "splicing variant" means two or more kinds of mature mRNAs generated by selectively splicing of the mRNA precursor of a certain gene transcribed from a genome in the expression of the gene in a eukaryote, the complementary DNAs of the mature mRNAs, or the proteins translated from the mature mRNAs. Expression of a gene in a eukaryote is carried out by forming a mature mRNA through splicing of the mRNA precursor transcribed from a region composed of exons present on the genome in scattered fashion and introns present between the exons. Further, a protein is produced by translation of the mature mRNA. The term "splicing" means a process where an intron is cut out from an mRNA precursor at a splice site (a boundary point between the intron and the exon) to form a mature mRNA. At the time of splicing, the splice sites some times happen to change in position and combination to generate two or more kinds of mature mRNAs, that is, a so-called selective splicing. As a result of the selective splicing, in many cases, two or more kinds of proteins are produced from the one gene.

The splicing variant of the DNA represented by the base sequence described in SEQ ID NO: 1 can be two or more kinds of mature mRNAs generated by selective splicing of a mRNA precursor transcribed from a genome of the gene consisting of the DNA, or the complementary DNA of the mature mRNA.

The splicing variant of the DNA represented by the base sequence described in SEQ ID NO: 1 can be preferably exemplified by a DNA represented by any one of base sequences described in SEQ ID NOs: 15, 17, 19 and 21.

The DNA represented by the base sequence described in SEQ ID NO: 19 encodes a protein having the longest amino acid sequence among proteins encoded by the DNA represented by any one of base sequences described in SEQ ID NO: 1, 15, 17, 19 and 21.

The splicing variant of the protein encoded by the DNA represented by the base sequence described in SEQ ID NO: 1 is not limited to the splicing variant exemplified above and includes any of splicing variants as long as it is a splicing variant that has homology in sequence and similarity in structural characteristics to the DNA, and encodes a protein having an equivalent biological function to the protein being encoded by the DNA.

The splicing variant of a protein encoded by the DNA represented by the base sequence described in SEQ ID NO: 1 is a protein translated from two or more kinds of mature mRNAs generated by selective splicing of a mRNA precursor of a gene encoding the protein that transcribed from a genome.

The splicing variant of the protein encoded by DNA represented by the base sequence described in SEQ ID NO: 1 can be preferably exemplified by a protein encoded by DNA represented by the base sequence described in SEQ ID NOs: 15, 17, 19 and 21.

The protein encoded by DNA represented by the base sequence described in SEQ ID NOs: 15, 17, 19 and 21 can be preferably exemplified by a protein represented by any one of amino acid sequences described in SEQ ID NOs: 16, 18, 20 and 22.

The protein represented by the amino acid sequence described in SEQ ID NO: 20 is a protein having the longest amino acid sequence among proteins represented by any one of amino acid sequences described in SEQ ID NO: 2, 16, 18, 20 and 22.

The splicing variant of the protein encoded by the DNA represented by the base sequence described in SEQ ID NO: 1 is not limited to the splicing variant exemplified above, and includes any of splicing variants as long as it is a splicing variant that has homology in sequence and similarity in structural characteristics to the protein encoded by the DNA, and further has an equivalent biological function to that of the protein.

In other words, the splicing variant of the protein encoded by the DNA represented by the base sequence described in SEQ ID NO: 1 includes any of splicing variants, as long as it is a splicing variant that has homology in sequence and similarity in the structural characteristics to the protein represented by the amino acid sequence described in SEQ ID NO: 2, and has an equivalent biological function to that of the protein.

In the present specification, "homology in sequence" is suitably presented by normally 50% or more homology with the entire base sequence of a base sequence or an amino acid sequence, and preferably at least 70% homology therewith. The suitable sequence homology is more preferably greater than 70%, further preferably is 80% or more, still further preferably is 90% or more, and still more preferably is 95% or more.

Examples of a DNA that has sequence homology to the DNA represented by the base sequence described in SEQ ID NO: 1 include a DNA comprising a base sequence having a variation including a deletion, substitution, addition or insertion of one or more, for example 1 to 100, preferably 1 to 30, more preferably 1 to 20, further preferably 1 to 10, and particularly preferably 1 to several nucleotides in the base sequence of the DNA represented by the base sequence described in SEQ ID NO: 1. A preferable DNA is a DNA of this kind that encodes a protein having the above described biological function. The degree of variation and the location thereof and the like are not particularly limited, as long as a DNA having the variation has similar structural characteristics as the above DNA and has a biological function that is equivalent to that of the protein encoded by the DNA comprising the base sequence represented by SEQ ID NO: 1.

A DNA having this kind of variation may be a natural DNA or may be a DNA obtained by introduction of a variation on the basis of a gene existing in nature. Techniques for introducing a variation are known, for example, site-directed mutagenesis, genetic homologous recombination, primer extension, and polymerase chain reaction (hereunder, abbreviated as PCR), and these techniques can be used independently or in suitable combinations thereof. For example, a variation may be introduced in accordance with a method described in a book (Sambrook et al., Eds., "Molecular Cloning, A Laboratory Manual, 2nd Edition", 1989, Cold Spring Harbor Laboratory; Muramatsu S., Ed., "Labomanual Genetic Engineering", 1988, Maruzen Co., Ltd.) or by modifying these methods, and Ulmer's technique (Ulmer, K. M., "Science", 1983, Vol. 219, p. 666-671) may also be utilized.

As a further example of the DNA used in the present invention, a DNA that hybridizes with the DNA represented by the base sequence described in SEQ ID NO: 1 and a splicing valiant of the DNA under stringent conditions may also be mentioned. The hybridization conditions can, for example, be accordance with a method described in a book (Sambrook et al., Eds., "Molecular Cloning, A Laboratory Manual, 2nd Edition", 1989, Cold Spring Harbor Laboratory) or the like. More specifically, the phrase "under stringent conditions" refers to, for example, conditions of heating at 42° C. in a solution containing 6×SSC, 0.5% SDS and 50% formamide, and then washing at 68° C. in a solution containing 0.1×SSC and 0.5% SDS. As long as these DNAs are DNAs that hybridize with a DNA that hybridizes with the DNA represented by the base sequence described in SEQ ID NO: 1 and a splicing valiant of the DNA, it is not necessary that they are DNAs having the complementary sequence thereof. Preferably, the DNA is a DNA encoding a protein that has a homogeneous function to the protein encoded by the DNA represented by the base sequence described in SEQ ID NO: 1 and a splicing valiant of the DNA.

Examples of a protein that has sequence homology to the protein encoded by the DNA represented by the base sequence described in SEQ ID NO: 1 include a protein comprising an amino acid sequence having a variation including a deletion, substitution, addition or insertion of one or more, for example 1 to 100, preferably 1 to 30, more preferably 1 to 20, further preferably 1 to 10, and particularly preferably one to several amino acids in the amino acid sequence represented by SEQ ID NO: 2 and having the aforementioned biological function. The degree of variation of the amino acids and the positions and the like thereof are not particularly limited, as long as the protein having the variation has a homogeneous function to the protein represented by the amino acid sequence described in SEQ ID NO: 2.

A protein having the variation may be a protein that was naturally produced by, for example, a mutation or posttranslational modification, or may be a protein obtained by introduction of a mutation based on a gene existing in nature. Techniques for introducing a variation are known, for example, site-directed mutagenesis, genetic homologous recombination, primer extension, and PCR, and these techniques can be used independently or in suitable combinations thereof. For example, a variation may be introduced in accordance with a method described in a book (Sambrook et al., Eds., "Molecular Cloning, A Laboratory Manual, 2nd Edition", 1989, Cold Spring Harbor Laboratory; Muramatsu Masami., Ed., "Labomanual Genetic Engineering", 1988, Maruzen Co., Ltd.) or by modifying these methods, and Ulmer's technique (Ulmer, K. M., "Science", 1983, Vol. 219, p. 666-671) can also be utilized. When introducing a variation, from the viewpoint of not altering the fundamental properties (physical properties, function, physiological activity, immunological activity or the like) of the protein, for example, mutual substitution among homologous amino acids (polar amino acids, nonpolar amino acids, hydrophobic amino acids, hydrophilic amino acids, positively charged amino acids, negatively charged amino acids and aromatic amino acids and the like) can be easily supposed.

Examples of the structural characteristics of the DNA include a seven-span transmembrane domain coding region and a TSP-I domain coding region. Besides, examples of the structural characteristics of the protein include a seven-span transmembrane domain and a TSP-I domain. A preferable DNA or protein has sequence homology in these types of regions or domains that is preferably at least 70%, more preferably greater than 70%, further preferably is 80% or more, still further preferably is 90% or more, and still more preferably is 95% or more. It is further preferable that these domains are domains that retain a function thereof, for example, a function that localizes a protein including the domain on a membrane or an angiogenesis inhibiting function.

In addition, examples of the structural characteristics of the DNA include a conserved region encoding an amino acid sequence (QTEV) described in SEQ ID NO: 3 that are present in the 3'-terminal region of the DNA. The structural characteristics of the protein encoded by the DNA can be exemplified by a conserved amino acid sequence (QTEV) described in SEQ ID NO: 3 that are present in the C-terminal region of the protein.

Regarding the functional characteristics of the protein encoded by the DNA represented by the base sequence described in SEQ ID NO: 1, a function as a membrane protein receptor can be mentioned. The phrase "function as a membrane protein receptor" refers to a function that promotes intracellular signal transduction through the action of a ligand to induce a biological response in an animal cell by expression as a membrane protein when expressed in the cell. For example, an equivalent function to a GPCR may be mentioned. The phrase "equivalent function to a GPCR" refers to a function which binds to G protein by action of a ligand to activate the G protein, and promotes intracellular signal transduction to induce a biological response in the cell.

As specific examples of a biological response of a cell, a change in cell membrane potential or a change in intracellular calcium concentration can be mentioned. A change in cell membrane potential or a change in intracellular calcium concentration can be measured by a known method. A change in cell membrane potential can be detected, for example, by expressing the DNA represented by the base sequence described in SEQ ID NO: 1 or a splicing valiant of the DNA in *Xenopus laevis* oocyte, measuring the amount of current generated specifically for membrane protein receptor in the presence and absence of ligand stimulation, and comparing the amounts of current. A change in intracellular calcium concentration can be detected, for example, by incorporating into the cell a fluorescent substance that can bind with calcium ion, eliciting a fluorescence phenomenon by excitation light in the presence and absence of ligand stimulation, and comparing the fluorescence amounts.

Examples of a ligand include a sample prepared from a cell or biotissue in which expression of the DNA represented by the base sequence described in SEQ ID NO: 1 or a splicing valiant of the DNA was recognized. Sample preparation can be carried out, for example, by culturing cells or tissue according to a known method, and then employing a method which obtains the culture supernatant by centrifuging or the like, or a method which disrupts or lyses the cells or tissue by a known method. A ligand can also be acquired for use by purification from these samples by a known protein purification method, for example, gel filtration chromatography. Specific examples of a ligand include, but are not limited to, culture supernatant of the HeLa cell line that was used in the present example, and any substance can be used as a ligand as long as it can act on the gene product of the DNA that expressed in a cell to induce a biological response in the cell.

More preferably, CCK-8S (SEQ ID NO: 14) can be exemplified as a ligand.

As an example of a different biological function of the protein encoded by the DNA represented by the base sequence described in SEQ ID NO: 1, a function that interacts with a protein having guanylate kinase activity and/or a cell adhesion function, for example a MAGUK family protein, may be also mentioned. Specific examples of MAGUK family protein include DLG2, DLG3 DLG4, AIP1 and MAGI3.

As described above, the DNA represented by the base sequence described in SEQ ID NO: 1 and a splicing variant of the DNA is a DNA that encodes a protein working as a functional membrane protein receptor having a seven-span transmembrane domain. Regarding the structural characteristics, the protein encoded by the DNA has several, preferably two to four TSP-I domains, one GPS (GPCR proteolytic site) domain and one seven-span transmembrane domain as the structural characteristics (see FIG. 1-A and FIG. 1-B).

The DNA represented by the base sequence described in SEQ ID NO: 1 comprises a base sequence of 4557 bps that contains an open reading frame (ORF) encoding 1518 amino acid residues (SEQ ID NO: 2) that have a portion predicted to be a signal sequence (20 amino acid residues from N-terminus).

The protein encoded by the DNA represented by the base sequence described in SEQ ID NO: 1 is preferably exemplified by a protein represented by the amino acid sequence described in SEQ ID NO: 2.

The protein encoded by the DNA represented by the base sequence described in SEQ ID NO: 1 comprises 1518 amino acid residues (SEQ ID NO: 2) having a portion predicted to be a signal sequence (20 amino acid residues from N-terminus) and has a GPS domain and a seven-span transmembrane domain (seven-span transmembrane domain) in amino acid sequence thereof in addition to three TSP-I domains (see FIG. 1-A and FIG. 1-B). The amino acid sequence of this protein is identical to the amino acid sequence of the protein represented by the amino acid sequence described in SEQ ID NO: 20 except for the deletion of 55 amino acid residues including one TSP-I domain at N-side. The deleted 55 amino acid residues correspond to, in the amino acid sequence of the protein represented by the amino acid sequence described in SEQ ID NO: 20, those from glycine (G) at position 296 to proline (P) at position 350. The three TSP-I domains respectively comprise, in the amino acid sequence represented by SEQ ID NO: 2, the region from histidine (His) at position 297 to proline (Pro) at position 350, the region from glutamic acid (Glu) at position 352 to proline (Pro) at position 405, and the region from aspartic acid (Asp) at position 408 to proline (Pro) at position 461. The seven transmembrane domains respectively comprise, in the amino acid sequence represented by SEQ ID NO: 2, the region from valine (Val) at position 870 to phenylalanine (Phe) at position 890, the region from serine (Ser) at position 899 to glycine (Gly) at position 919, the region from valine (Val) at position 928 to leucine (Leu) at position 948, the region from arginine (Arg) at position 970 to threonine (Thr) at position 990, the region from alanine (Ala) at position 1012 to phenylalanine (Phe) at position 1032, the region from leucine (Leu) at position 1087 to alanine (Ala) at position 1107, and the region from valine (Val) at position 1114 to valine (Val) at position 1134.

The DNA represented by the base sequence described in SEQ ID NO: 15 comprises a base sequence of 4389 bps that contains ORF encoding 1463 amino acid residues (SEQ ID NO: 16) that have a portion predicted to be signal sequence (20 amino acid residues from N-terminus).

The protein encoded by the DNA represented by the base sequence described in SEQ ID NO: 15 is preferably exemplified by a protein represented by the amino acid sequence described in SEQ ID NO: 16.

The protein encoded by the DNA represented by the base sequence described in SEQ ID NO: 15 comprises 1463 amino acid residues (SEQ ID NO: 16) having a portion predicted to be a signal sequence (20 amino acid residues from N-terminus) and has a seven-span transmembrane domain and has two TSP-I domains and one GPS domain. (See FIG. 1-B). The amino acid sequence of the protein encoded by this DNA is identical to the protein encoded by the DNA represented by the base sequence described in SEQ ID NO: 19 except that 110 amino acid residues containing two TSP-I domains at N-terminal side are deleted. The deleted 110 amino acid residues correspond to, in the amino acid sequence of the protein encoded by the DNA represented by the base sequence described in SEQ ID NO: 19, those from glycine (G) at position 296 to proline (P) at position 405.

The DNA represented by the base sequence described in SEQ ID NO: 17 comprises a base sequence of 4554 bps that contains ORF encoding 1518 amino acid residues (SEQ ID NO: 18) that have a portion predicted to be signal sequence (20 amino acid residues from N-terminus).

The protein encoded by the DNA represented by the base sequence described in SEQ ID NO: 17 is preferably exemplified by a protein represented by the amino acid sequence described in SEQ ID NO: 18.

The protein encoded by the DNA represented by the base sequence described in SEQ ID NO: 17 comprises 1518 amino acid residues (SEQ ID NO: 18) having a portion predicted to be a signal sequence (20 amino acid residues from N-terminus) and has a seven-span transmembrane domain and has three TSP-I domains and one GPS domain. (See FIG. 1-B). The amino acid sequence of the protein encoded by the DNA is identical with the protein encoded by the DNA represented by the base sequence described in SEQ ID NO: 19 except that 55 amino acid residues containing one TSP-I domain second from N-terminal side are deleted. The deleted 55 amino acid residues correspond to, in the amino acid sequence of the protein encoded by the DNA represented by the base sequence described in SEQ ID NO: 19, those from valine (V) at position 351 to proline (P) at position 405.

The DNA represented by the base sequence described in SEQ ID NO: 19 is referred to as 7tmHR (seven transmembrane helix receptor) gene (GenBank, Accession NO: AB065648). This DNA comprises a base sequence of 4719 bps that contains ORF encoding 1573 amino acid residues (SEQ ID NO: 20) that have a portion predicted to be signal sequence (20 amino acid residues from N-terminus). The protein encoded by this DNA has a seven-span transmembrane domain, and has four TSP-I domains and one GPS domain.

The protein encoded by the DNA represented by the base sequence described in SEQ ID NO: 19 is preferably exemplified by a protein represented by the amino acid sequence described in SEQ ID NO: 20.

The protein encoded by the DNA represented by the base sequence described in SEQ ID NO: 19 is referred to as 7tmHR (GenBank, Accession NO: AB065648). This protein comprises 1573 amino acid residues and has a seven-span transmembrane domain, four TSP-I domains and one GPS domain in amino acid sequence thereof (see FIG. 1-B).

The DNA represented by the base sequence described in SEQ ID NO: 21 is a known human DNA and is referred to as hBAI2 gene (GenBank, Accession No: AB005298). This DNA comprises a base sequence of 5399 bps that contains ORF encoding 1572 amino acid residues (SEQ ID NO: 22) that have a portion predicted to be signal sequence (20 amino acid residues from N-terminus).

The protein encoded by the DNA represented by the base sequence described in SEQ ID NO: 21 is preferably exemplified by a protein represented by the amino acid sequence described in SEQ ID NO: 22.

The protein encoded by the DNA represented by the base sequence described in SEQ ID NO: 21 is a known human DNA and is referred to as hBAI2 gene (GenBank, Accession No: AB005298). This protein comprises 1572 amino acid residues and has a seven-span transmembrane domain, and has four TSP-I domains and one GPS domain. (See FIG. 1-A). The amino acid sequence of the protein is identical to the amino acid sequence of the protein encoded by the DNA represented by the base sequence described in SEQ ID NO: 19 except for deletion of one amino acid residue corresponding to lysine at position 1461 in C-terminal region.

A DNA represented by any one of base sequences described in SEQ ID NO: 1, 15, 17, 19 and 21 has homology to each other as mentioned above as well as the protein encoded by the DNA does, and conserves a TSP-I domain, GSP domain and seven-span transmembrane domain.

The inventors consider that the DNA represented by any one of the base sequences described in SEQ ID NO: 1, 15, 17, 19 and 21 and the protein encoded by the DNA are splicing variants from view points of homology in the sequence and similarity in structural characteristics.

The proteins represented by any one of amino acid sequences described in SEQ ID NO: 2, 16, 18, 20 and 22 have homology to each other and conserve TSP-I domain, GPS domain and seven-span transmembrane domain. The inventors consider that these proteins are splicing variants from viewpoints of homology in sequence and similarity in structural characteristics.

A gene product of the DNA represented by any one of base sequences described in SEQ ID NO: 15, 17, and 19 was actually exhibited the function as a membrane protein receptor. Specifically, it was observed that a cell response via intracellular signal transduction was caused by CCK-8S (SEQ ID NO: 14) stimulation in an animal cell expressing the gene product as in an animal cell expressing the gene product of the DNA represented by the base sequence described in SEQ ID NO: 1.

A DNA used in the present invention can be a DNA represented by the base sequence that comprises any of the base sequences of the aforementioned DNAs, for example, the base sequence described in SEQ ID NO: 1, 15, 17, 19 and 21.

In addition, a DNA used in the present invention can be a DNA fragment represented by a partial base sequence that is present in a designated region of the DNA represented by the base sequence described in SEQ ID NO: 1 or in a homolog of the DNA. Such a DNA fragment is useful for using as primers or probes for detecting the DNA represented by the base sequence described in SEQ ID NO: 1, or as primers for producing the DNA. The primer preferably consists of 15 to 30 nucleotides, and more preferably 20 to 25 nucleotides. The probe preferably consists of 8 to 50 nucleotides, more preferably 17 to 35 nucleotides, and further preferably 17 to 30 nucleotides. If the length of a primer or probe is longer than a suitable length, the specificity will decrease due to an increase in false hybridization. Further, if the length is shorter than a suitable length, the specificity will decrease due to the occurrence of mismatches.

A designated region of the DNA represented by the base sequence described in SEQ ID NO: 1 or a homolog of the DNA is preferably exemplified by a region encoding a fragment of the protein that is encoded by the DNA and contains the site at which a ligand acts. A DNA fragment represented by a partial base sequence that is present in a region encoding a fragment containing a site at which a ligand acts can be used in the production of a fragment containing a site at which the ligand acts. A fragment containing a site at which a ligand acts is useful for detecting an action of a ligand to the protein used in the present invention, for example, binding between the protein and the ligand, or identifying a compound that promotes or inhibits the action. Alternatively, the fragment is useful for identifying a compound having the same action as a ligand to the protein, i.e. an agonist. The minimum unit of this kind of DNA fragment preferably comprises five or more consecutive nucleotides in the region, more preferably ten or more nucleotides, and further preferably 20 or more nucleotides.

A DNA fragment represented by a partial base sequence that is present in a designated region of the DNA represented by the base sequence described in SEQ ID NO: 1 or in a homolog of the DNA is also useful for using as an antisense oligonucleotide that inhibits expression of the DNA, when it is a complementary DNA fragment to a sense strand encoding a protein, it can be used. Since it is known that, generally, a DNA fragment consisting of approximately 20 nucleotides can inhibit expression of a gene, the antisense oligonucleotide preferably consists of 15 or more nucleotides, and more preferably 20 or more nucleotides.

These DNA fragments can be prepared according to a known chemical synthesis method by designing a fragment having the target sequence in accordance with the base sequence information of the DNA represented by the base sequence described in SEQ ID NO: 1 or a homolog of the DNA. As a simple and convenient method, the DNA fragments can be prepared using an automated DNA/RNA synthesizer.

A protein used in the present invention can be a protein represented by the amino acid sequence that comprises any of the base sequences of the aforementioned proteins, for example, the base sequence described in SEQ ID NO: 2, 16, 18, 20 and 22.

In addition, a protein used in the present invention can be a fragment represented by a partial amino acid sequence that is present in a designated region of the protein encoded by the DNA represented by the base sequence described in SEQ ID NO: 1 or in a homolog of the protein. Such a fragment is useful for using as an antigen in order to produce an antibody against the protein.

As a designated region of the protein used in the present invention, a site at which a ligand acts in the protein may be preferably mentioned. A fragment containing a site at which a ligand acts is useful for detecting action of ligand to the protein, for example, for detecting binding between the protein and the ligand, or identifying a compound that promotes or inhibits the action. Alternatively, the fragment is useful for identifying a compound having a similar action as a ligand to the protein, that is, an agonist. Further, among fragments containing a site at which a ligand acts to, a fragment that inhibits an interaction between the ligand and the protein is useful as a compound for inhibiting induction of a function of the protein by the action of the ligand.

This kind of fragment preferably comprises, as a minimum unit, five or more consecutive amino acids, more preferably eight or more, further preferably twelve or more, and still further preferably fifteen or more consecutive amino acids. These fragments can be prepared according to a known chemical synthesis method by designing a fragment having the target sequence in accordance with the amino acid sequence information of the protein.

A protein used in the present invention may be a protein prepared from a cell or biological sample in which a gene encoding the protein was expressed by a genetic engineering technique, may be a synthetic product in a cell-free system or a product obtained by chemical synthesis, or a substance obtained by further purifying a product obtained from these. The protein can also be a protein that expresses in a cell that includes the gene encoding the protein. The cell can be a transformant obtained by transfection with a vector containing the gene encoding the protein.

A constitutive amino group or carboxyl group or the like of the protein used in the present invention can also be modified to a degree that does not noticeably change the function thereof, for example, by an amidating modification or the like. Further, the protein may be one that was labeled by attaching a different protein or the like directly or indirectly via a linker peptide or the like using a genetic engineering technique or the like to the N-terminal side or C-terminal side thereof. Labeling that does not inhibit the fundamental properties of the protein is preferable. Examples of the protein or the like to be attached include, but are not limited to, enzymes such as GST, β-galactosidase, HRP or ALP, tag peptides such as His-tag, Myc-tag, HA-tag, FLAG-tag or Xpress-tag, fluorescent substances such as fluorescein isothiocyanate or phycoerythrin, maltose-binding protein, Fc fragment of immunoglobulin and biotin. Labeling can also be carries out using radioactive isotope. The substance used for labeling can be attached individually or in combinations of two or more. By assaying the substance itself used in labeling or the function thereof, the protein can be simply detected or purified, or, for example, interaction between the protein used in the present invention and another protein can be detected.

(Preparation of DNA)

The DNA used in the present invention can be readily acquired by a known genetic engineering technique (refer to Sambrook et al., Eds., "Molecular Cloning, A Laboratory Manual, 2nd Edition", 1989, Cold Spring Harbor Laboratory; Muramatsu S., Ed., "Labomanual Genetic Engineering", 1988, Maruzen Co., Ltd.) based on sequence information of the DNA. For example, the DNAs represented by the base sequences described in SEQ ID NO: 1, 15, 17, 19 and 21 in the sequence listing can be obtained by a known genetic engineering technique based on their sequence information.

More specifically, the DNA used in the present invention can be acquired by preparing a cDNA library in accordance with an ordinary method from a suitable origin in which expression of the DNA of the invention is confirmed, and then selecting a desired clone from the library using a suitable probe or primer that is specific to the DNA. Examples of the cDNA origin include various cells or tissue in which expression of the DNA is confirmed, or cultured cells derived from these. For example, the origin of the DNA represented by the base sequences described in SEQ ID NO: 1 and a splicing variant thereof can be human brain cells or the like.

Isolation of total RNA from these origins, isolation and purification of mRNA, acquisition of cDNA and the cloning thereof and the like can each be carried out in accordance with an ordinary method. It is also possible to use a cDNA library that was constructed from commercially available polyA+ RNA derived from the human brain, fetal brain or cerebral hippocampus. A method for selecting a desired clone from a cDNA library is also not particularly limited, and a commonly used method can be used. Examples thereof include a plaque hybridization method or colony hybridization method that uses a probe which binding selectively to the target DNA sequence, or a combination of these methods. As a probe used in this case, a DNA or the like that was chemically synthesized on the basis of information relating to the base sequence of the DNA can generally be used. A sense primer and antisense primer that were designed on the basis of the base sequence information of the DNA can also be used as this kind of probe.

Selection of a target clone from a cDNA library can be carried out, for example, by confirming an expression protein for each clone utilizing a known protein expression system, using the biological function thereof as an indicator.

In addition, a DNA/RNA amplification method according to PCR (Ulmer, K. M., "Science", 1983, Vol. 219, pp. 666-671; Ehrlich, H. A., Ed., "PCR Technology. Principles and Applications for DNA Amplification", 1989, Stockton Press; Saiki, R. K., et al., "Science", 1985, Vol. 230, pp. 1350-1354) can be favorably utilized to acquire the DNA. When it is difficult to acquire full length cDNA from a cDNA library, a RACE method ("Jikken Igaku (Experimental Medicine)", 1994, Vol. 12, No. 6, p. 615-618), and particularly the 5'-RACE method (Frohman, M. A., "Proceedings of The National Academy of Sciences of The United States of America", 1988, Vol. 85, No. 23, pp. 8998-9002) or the like can be favorably employed. Primers to be used for PCR can be suitably designed based on the base sequence information of the DNA, and obtained by synthesis in accordance with an ordinary method. Isolation and purification of amplified DNA/RNA fragments can be carried out according to an ordinary method. For example, isolation and purification of amplified DNA/RNA fragments can be carried out by gel electrophoresis or the like.

Determination of the base sequence of DNA obtained in this manner can be carried out by an ordinary method, for example, the dideoxy chain termination method ("Proceedings of The National Academy of Sciences of The United States of America", 1977, Vol. 74, pp. 5463-5467) or the Maxam-Gilbert method (Methods in Enzymology", 1980, Vol. 65, p. 499-560), or simply and conveniently using a commercially available sequencing kit or the like.

The DNA may also be a DNA to the 5'-terminal side or 3'-terminal side of which one or more genes of, for example, enzymes such as glutathione S-transferase (GST), β-galactosidase, horseradish peroxidase (HRP) or alkaline phosphatase (ALP), or tag peptides such as His-tag, Myc-tag, HA-tag, FLAG-tag or Xpress-tag are ligated as long as the function thereof, for example, expression of the protein encoded by the DNA or the function of the expressed protein, is not inhibited. Attachment of these genes can be carried out by a commonly used genetic engineering technique, and is useful to facilitate detection of a gene or mRNA.

(Vector)

A recombinant vector containing the DNA used in the present invention can be obtained by inserting the DNA into a suitable vector DNA. The recombinant vector may be any kind of recombinant vector, as long as it is a recombinant vector into which the DNA used in the present invention is incorporated.

The vector DNA is not particularly limited as long as it can be replicated within a host, and it can be suitably selected in accordance with the kind of host and purpose of use. The vector DNA may be extracted from a substance existing in nature, or may be one in which one part of a DNA segment other than a segment necessary for replication has been deleted. As typical examples, vector DNA derived from a plasmid, a bacteriophage or a virus may be mentioned. Examples of plasmid DNA include a plasmid derived from *Escherichia coli*, a plasmid derived from *Bacillus subtilis*, and a plasmid derived from yeast. Examples of a bacteriophage DNA include λ phage. Examples of vector DNA derived from a virus include a vector derived from an animal virus such as retrovirus, vaccinia virus, adenovirus, papovavirus, SV 40, fowlpox virus, and pseudorabies virus, or a vector derived from an insect virus such as baculovirus. Other examples thereof include vector DNA derived from a transposon, an insertion element, or a yeast chromosome element. Alternatively, vector DNA obtained by combining two or more of these, for example, vector DNA (cosmid or phagemid or the like) produced by combining genetic elements of a plasmid and a bacteriophage may be employed. Further, an expression vector or cloning vector or the like can also be used in accordance with the object.

It is necessary for a gene to be incorporated into the vector so that the target function of the gene is exerted, and the vector should comprise at least the target gene sequence and a promoter. In addition to these elements, as desired, a genetic sequence that holds information relating to replication and control, for example, one or a plurality of genetic sequences combined according to a known method selected from the group consisting of a ribosome binding sequence, terminator, signal sequence, cis element such as an enhancer, splicing signal and selective marker can be incorporated into the vector DNA. As a selective marker, for example, dihydrofolate reductase gene, ampicillin-resistant gene and neomycin-resistant gene may be mentioned.

A known method can be applied to a method for incorporating the gene sequence of interest into the vector DNA. For example, a method can be used in which the gene sequence of interest is treated with a restriction enzyme to be cleaved at a specific site, subsequently mixed with similarly treated vector DNA, and finally reconnected using a ligase. Alternatively, a desired recombinant vector can also be obtained by ligating a suitable linker to the gene sequence of interest, and then inserting this into a multicloning site of a vector suited to the purpose.

(Transformant)

A transformant can be obtained by introducing a vector DNA containing the DNA used in the present invention into a host. When using an expression vector as the vector DNA, the DNA can be expressed, and a protein encoded by the DNA can also be produced. One or more vector DNA containing a desired gene other than the DNA used in the present invention can also be introduced into the transformant.

Both prokaryotes and eukaryotes can be used as a host. Examples of the prokaryotes include bacteria belonging to *Escherichia*, such as *Escherichia coli*, bacteria belonging to *Bacillus*, such as *Bacillus subtilis*, bacteria belonging to *Pseudomonas*, such as *Pseudomonas putida*, and bacteria belonging to *Rhizobium*, such as *Rhizobium meliloti*. Examples of the eukaryotes include yeasts such as *Saccharomyces cerevisiae* and *Schizosaccharomyces pombe*, insect cells such as Sf9 and Sf21, and animal cells such as cells of monkey kidney (COS cells, Vero cells), Chinese hamster ovary cells (CHO cells), mouse L cells, rat GH3 cells, human FL cells or 293 EBNA cells, and *Xenopus laevis* oocyte. Preferably, animal cells are used.

Introduction of vector DNA into the host cell can be performed according to a known method, for example, by applying a standard method described in a book (Sambrook et al., Eds., "Molecular Cloning, A Laboratory Manual, 2nd Edition", 1989, Cold Spring Harbor Laboratory). Although a method which integrates the gene onto the chromosome may be mentioned as a more preferable method in consideration of the stability of the gene, an autonomous replication system that utilizes an extranuclear gene can be used as a simple method. As specific methods, calcium phosphate transfection, DEAE-dextran mediated transfection, microinjection, cationic lipid-mediated transfection, electroporation, transduction, scrape loading, ballistic introduction and infection may be mentioned.

When employing an animal cell as the host, preferably the recombinant vector is capable of autonomous replication within the cell and is also composed of a promoter, RNA splice site, target gene, polyadenylated site and a transcription terminating sequence. As desired, it may also contain an origin of replication. As a promoter, SRα promoter, SV 40 promoter, LTR promoter, CMV promoter and the like can be used, and early gene promoter of cytomegalovirus and the like can also be used. As a method for introducing the recombinant vector into an animal cell, preferably, for example, electroporation, the calcium phosphate technique, lipofection or the like is used.

When employing a prokaryote as the host, preferably the recombinant vector is capable of autonomous replication within the bacterium and is also composed of a promoter, a ribosomal binding sequence, the target gene and a transcription terminating sequence. It may also contain a gene that regulates the promoter.

When employing bacteria as the host, the promoter is not particularly limited and any promoter may be used as long as it can express in a host such as *Escherichia coli*. For example, a promoter derived from *Escherichia coli* or a phage, such as trp promoter, lac promoter, PL promoter or PR promoter may be mentioned. An artificially designed and modified promoter such as tac promoter may also be used. A method for introducing a recombinant vector into bacteria is not particularly limited as long as it is a method that introduces the DNA into the bacteria. Preferable examples thereof include a method using calcium ion, electroporation or the like.

When using yeast as a host, the promoter is not particularly limited and any promoter may be used as long as it can express in yeast. Examples thereof include gal1 promoter, gal10 promoter, heat shock protein promoter, MFα1 promoter, PHO5 promoter, PGK promoter, GAP promoter, ADH promoter, and AOX1 promoter. A method for introducing a recombinant vector into yeast is not particularly limited as long as it is a method that introduces the DNA into the yeast. Preferable examples thereof include a method using electroporation, spheroplast, lithium acetate or the like.

When using an insect cell as the host, preferable examples of a method for introducing a recombinant vector include a calcium phosphate technique, lipofection and electroporation.

As a specific example of the transformant obtained by transfecting with a vector DNA containing the DNA represented by the base sequence described in SEQ ID NO: 1 in the sequence listing, HA-ph01207#10-6 cell line may be mentioned. HA-ph01207#10-6 cell line is a cell line that was established by transfecting the CHO-K1 cell line with a vector that allows for the expression of the DNA comprising the base sequence of the ORF of the DNA represented by the base sequence described in SEQ ID NO: 1 from which a segment predicted to encode a signal sequence (20 amino acid residues from the N-terminus of the amino acid sequence represented by SEQ ID NO: 2) is excluded, as an N-terminal HA-tag fusion protein. The HA-ph01207#10-6 cell line stably expresses the N-terminal HA-tag fusion protein. A specific method for producing this cell line is described in detail in Example 2.

The HA-ph01207#10-6 cell line was deposited with the International Patent Organism Depositary of the National Institute of Advanced Industrial Science and Technology (Japan, AIST Tsukuba Central 6, 1-1, Higashi 1-chome, Tsukuba, Ibaraki) on Aug. 19, 2004 under Accession NO: FERM BP-10101. The existence of this cell line was confirmed by experiment at the International Patent Organism Depositary on Sep. 22, 2004.

(Method for Producing the Protein)

The protein used in the present invention can be produced, for example, by an ordinary genetic engineering technique based on the base sequence information of the gene encoding the protein (see, Sambrook et al., Eds., "Molecular Cloning, A Laboratory Manual, 2nd Edition", 1989, Cold Spring Harbor Laboratory; Muramatsu Masami., Ed., "Labomanual Genetic Engineering", 1988, Maruzen Co., Ltd.; Ulmer, K. M., "Science", 1983, Vol. 219, p. 666-671; Ehrlich, H. A., Ed., "PCR Technology. Principles and Applications for DNA Amplification", 1989, Stockton Press). For example, the protein can be acquired by preparing a cDNA library in accordance with an ordinary method from various cells or tissues in which expression of the gene encoding the protein is confirmed or cultured cells derived from these, for example, human brain, amplifying the gene encoding the protein using a suitable primer that is specific to the gene, and inducing expression of the obtained gene by a known genetic engineering technique.

More specifically, for example, the protein can be produced by culturing a transformant transfected with a vector DNA comprising the aforementioned DNA, and then recovering the protein of interest from the obtained culture. Cultivation of the transformant can be carried out according to a known culture conditions and culture method that are best suited to the respective hosts. Cultivation can be carried out employing the protein itself that is expressed by the transformant or a function thereof as an indicator. Alternatively, cultivation may be carried out employing the protein itself or the protein amount thereof that is produced in the host or outside the host as an indicator, or by subculture or batch culture employing the amount of transformant in the culture medium as an indicator.

When the target protein expresses within the cell of the transformant or on the cell membrane, the transformant can be disrupted to extract the target protein. Further, when the target protein is secreted outside the transformant, the culture medium can be used as it is or the culture medium can be used after removing the transformant by centrifugation or the like.

A protein used in the present invention can also be produced according to an ordinary chemical synthesis method. For example, solid phase synthesis, solution phase synthesis and the like are known as methods of chemically synthesizing a protein, and any of these methods can be used. These kinds of protein synthesis methods more specifically include a so-called stepwise elongation method that sequentially binds each amino acid, one at a time, to elongate a chain based on the amino acid sequence information, and a fragment condensation method that previously synthesizes fragments comprising several amino acids and subsequently subjects the respective fragments to a coupling reaction, and synthesis of the protein can be performed by either of these methods. A condensation method used for the above described protein synthesis can also be carried out according to an ordinary method, and examples thereof include an azide method, mixed anhydride method, DCC method, active ester method, oxidation-reduction method, DPPA (diphenylphosphoryl azide) method, DCC+additive (1-hydroxybenzotriazole, N-hydroxysuccinamide, N-hydroxy-5-norbornane-2,3-dicarboxyimide and the like) method, and Woodward's method. A protein obtained by chemical synthesis can be suitably purified in accordance with various kinds of common purification methods as described above.

A protein used in the present invention can be fragmented by cleaving the protein using a suitable peptidase, and as a result, fragments of the protein can be obtained.

As desired, the protein can be isolated and/or purified from a culture medium used to culture the transformant or from the transformant. Isolation and/or purification can be carried out employing a function of the protein as an indicator. Examples of isolation methods include, ammonium sulfate precipitation, ultrafiltration, gel chromatography, ion-exchange chromatography, affinity chromatography, high performance liquid chromatography, and dialysis, and these methods may be used independently or in suitable combinations thereof. Preferably, as a recommended method, an antibody that is specific to the protein of interest is prepared based on amino acid sequence information of the protein to carry out specific adsorption using the antibody, for example, affinity chromatography utilizing a column that binds the antibody.

(Antibody)

The antibody can be produced using the protein used in the present invention or the fragment thereof as an antigen. The antigen may be the protein or a fragment thereof, and consists of at least eight, preferably at least ten, more preferably at least twelve and further preferably fifteen or more amino acids. In order to produce an antibody that is specific to the protein used in the present invention and/or a fragment thereof, a region comprising a characteristic amino acid sequence of the protein used in the present invention or a fragment thereof is preferably used. The amino acid sequence of this region need not necessarily be homologous or identical to a sequence of the protein or a fragment thereof, and a site that is exposed outward on the tertiary structure thereof is preferable, and even if the amino acid sequence of the exposure site is not continuous on the primary structure, it is sufficient if the amino acid sequence is continuous with respect to the exposure site. The antibody is not particularly limited as long as it can specifically bind to or recognize the protein used in the present invention and/or a fragment thereof immunologically. The presence or absence of this binding or recognition can be determined by a known antigen-antibody binding reaction.

A known antibody producing method can be utilized for production of the antibody. For example, the antibody can be obtained by administering the antigen to an animal independently or bound to a carrier in the presence or absence of an adjuvant, and performing immunological induction such as humoral response and/or cellular response. A carrier is not particularly limited as long as it does not itself exhibit an adverse action against the host and enhances antigenicity, and examples thereof include cellulose, polymeric amino acids, albumin, and keyhole limpet hemocyanin. Examples of the adjuvant include Freund's complete adjuvant (FCA), Freund's incomplete adjuvant (FIA), Ribi (MPL), Ribi (TDM), Ribi (MPL+TDM), *Bordetella pertussis* vaccine, muramyl-dipeptide (MDP), aluminium adjuvant (ALUM), and combinations of these. As an animal to be immunized, mouse, rat, rabbit, goat, horse or the like is preferably used.

A polyclonal antibody can be acquired from serum of an animal that was administered with the antigen by a known antibody recovery method. As a preferable example of an antibody recovery method, immunoaffinity chromatography may be mentioned.

A monoclonal antibody can be produced by recovering antibody-producing cells (for example, lymph cells derived from spleen or lymph nodes) from an animal that was administered with the antigen, and introducing transforming means that uses known permanently proliferating cells (for example, myeloma strain of the P3-X63-Ag8 line). For example, antibody-producing cells and permanently proliferating cells are fused by a known method to produce a hybridoma, the hybridoma is cloned to screen for a hybridoma that produces an antibody that specifically recognizes the protein used in the present invention, and the antibody is then recovered from culture solution of that hybridoma.

A polyclonal antibody or monoclonal antibody obtained in this manner that can recognize and bind with the protein used in the present invention can be utilized as an antibody for purification of the protein, reagent or labeling marker. In particular, an antibody that inhibits the function of the protein, or an antibody that binds to the protein and exhibits a ligand-like action for the protein can be used for functional regulation of the protein. These antibodies are useful for elucidating, inhibiting, improving and/or treating various kinds of diseases attributable to an abnormality in the protein and the function thereof.

(Membrane Protein Receptor and its Ligand)

The protein used in the present invention is a protein that functions as a membrane protein receptor and was able to induce a cell response by CCK-8S (SEQ ID NO: 14) when expressed in animal cells. That is, CCK-8S (SEQ ID NO: 14) is one of ligands to a membrane protein receptor comprising the protein. Hereunder, a membrane protein receptor comprising the protein may also be referred to as "membrane protein receptor according to the present invention".

The cell response caused by CCK-8S (SEQ ID NO: 14) in animal cells that expressed the protein used in the present invention was observed in, specifically, above mentioned HA-ph01207#10-6 cell line in which the DNA represented by the base sequence described in SEQ ID NO: 1 of the sequence listing was stably expressed. More specifically, an increase in intracellular calcium concentration by action of CCK-8S (SEQ ID NO: 14) was observed in the HA-ph01207#10-6 cell line (see Example 5). The degree of increase in intracellular calcium concentration in the cell line caused by 1 nM of CCK-8S (SEQ ID NO: 14) was roughly equal to that caused by calcium ionophore A23187 as a positive control. In CHO-K1 cell line that did not express the DNA, this kind of increase in intracellular calcium concentration caused by CCK-8S (SEQ ID NO: 14) was not observed. Meanwhile, HA-ph01207#10-6 cell line did not respond to a peptide (CCK-8 Nonsulfated form, hereunder referred to as "CCK-8NS") in which the seventh tyrosine residue from C-terminus was not sulfated even though the peptide was a CCK octapeptide consisting of the same amino acid sequence as CCK-8S (SEQ ID NO: 14). Further, HA-ph01207#10-6 cell line did not respond to a tetrapeptide (CCK-4) consisting of the amino acid residues up to fourth residue from the C-terminus of CCK-8S (SEQ ID NO: 14). More specifically, an increase in intracellular calcium concentration caused by 1 nM of CCK-8NS or 1 nM of CCK-4 was not observed. It was thus clarified that HA-ph01207#10-6 cell line responds specifically to CCK-8S (SEQ ID NO: 14) and functions as a membrane protein receptor. Furthermore, because HA-ph01207#10-6 cell line responded to CCK-8S (SEQ ID NO: 14) but did not respond to CCK-8NS, the inventors considered that the fact that the seventh tyrosine residue from the C-terminus of the amino acid sequence of CCK-8S (SEQ ID NO: 14) is sulfated is important for the ligand action of CCK-8S (SEQ ID NO: 14).

The cell response caused by CCK-8S (SEQ ID NO: 14) was also observed in cells in which the DNA represented by the base sequence described in SEQ ID NO: 15, the DNA represented by the base sequence described in SEQ ID NO: 17, or the DNA represented by the base sequence described in SEQ ID NO: 19 was expressed. More specifically, in these cells, increase in intracellular calcium concentration by an action of 1 nM CCK-8S (SEQ ID NO: 14) was observed (Example 8). Meanwhile, in CHO-K1 cell line in which the DNA represented by the base sequence described in SEQ ID NO: 15, the DNA represented by the base sequence described in SEQ ID NO: 17, or the DNA represented by the base sequence described in SEQ ID NO: 19 was not expressed, such an increase in intracellular calcium concentration by CCK-8S (SEQ ID NO: 14) was not observed.

The protein encoded by the DNA represented by any one of base sequences described in SEQ ID NO: 1, 15, 17 and 19 was different to each other in number of repeats of TSP-I domain in the N-terminal extracellular region, but has the same amino acid sequence except for the domain (FIG. 1-B). A cell that was made to express the DNA represented by any one of base sequences described in SEQ ID NOs: 1, 15, 17 and 19 showed a cell response by CCK-8S (SEQ ID NO: 14) (Example 5, Example 8, and Example 9). Therefore, the inventors consider that TSP-1 domain may not participate in the binding of CCK-8S to the protein encoded by the DNA represented by any one of the base sequences described in SEQ ID NOs: 1, 15, 17 and 19, and in the intracellular signal transduction caused by the binding.

Since as low as 1 nM concentration of CCK-8S (SEQ ID NO: 14) caused a cell response in the HA-ph01207#10-6 cell line and in cells in which the DNA represented by the base sequence described in SEQ ID NO: 15, SEQ ID NO: 17, or SEQ ID NO: 19 was expressed, it can be considered that CCK-8S (SEQ ID NO: 14) may actually causes a cell response in vivo through the protein encoded by the DNA. That is, the present inventors consider that CCK-8S (SEQ ID NO: 14) may be one of in vivo ligands to a functional membrane protein receptor according to the present invention predicted to be GPCR. Further, the membrane protein receptor exhibited a cell response such as a change in membrane potential in *Xenopus laevis* oocyte when culture supernatant of HeLa cells is used as the ligand source. Therefore, HeLa cell culture supernatant can be considered to contain a ligand of the receptor.

In addition to CCK-8S (SEQ ID NO: 14), a peptide comprising an amino acid sequence having a variation including a deletion, substitution, addition or insertion of one or several amino acids in the amino acid sequence of CCK-8S (SEQ ID NO: 14) and having an equivalent function to CCK-8S is also included in the scope of the ligand of the membrane protein receptor of the present invention. The phrase "equivalent function to CCK-8S" refers to a function that induces a biological function of the membrane protein receptor of the present invention, and more specifically to a function that induces a biological response such as a rise in intracellular calcium concentration or a change in membrane potential in a cell expressing the membrane protein receptor of the present invention. Since the fact that the seventh tyrosine residue from the C-terminus of CCK-8S (SEQ ID NO: 14) is sulfated is considered important for the ligand action of CCK-8S (SEQ ID NO: 14), it is preferable that the sulfated tyrosine residue is retained in the ligand of the membrane protein receptor of the present invention. A protein having the variation may be a protein that was naturally produced by, for example, a mutation or posttranslational modification, or may be a protein obtained by introduction of a variation based on a gene existing in nature. Techniques for introducing a variation are known, and the above described methods can be used. From the viewpoint of not altering the fundamental properties (physical properties, functions, physiological activity, immunological activity or the like) of the protein in question, for example, mutual substitution among homologous amino acids (polar amino acids, nonpolar amino acids, hydrophobic amino acids, hydrophilic amino acids, positively charged amino acids, negatively charged amino acids and aromatic amino acids and the like) can be easily supposed. Further, CCK-8S (SEQ ID NO: 14), or peptides including a peptide comprising an amino acid sequence having a variation of one to several amino acids in the amino acid sequence of CCK-8S (SEQ ID NO: 14) and having an equivalent function to CCK-8S are included in the scope of the ligand of the membrane protein receptor of the present invention. In this kind of peptide, the sulfated tyrosine residue that is present at the seventh position from the C-terminus of CCK-8S is preferably retained.

Tissue expression of CCK is frequently observed in brain tissues, especially in brain cortex, hippocampus, amygdaloid body, and hypothalamus (see Table 3).

The inventors discovered that tissue expression of a DNA encoding the protein used in the present invention was observed in, specifically, brain cortex, hippocampus and amygdaloid body remarkably strongly (see Example 10 and Table 3). Since distribution of the expression of the DNA encoding the protein used in the present invention is identical to that of CCK, the inventors consider that a ligand of the membrane protein receptor may be CCK, for example, CCK-8S (SEQ ID NO: 14).

Since CCK-8S (SEQ ID NO: 14) may be one of the ligands for the membrane protein receptor of the present invention as described above, the inventors consider that the membrane protein receptor of the present invention is involved in neurologic functions such as memory retention in which CCK-8S (SEQ ID NO: 14) is thought to participate. A decline in the quantity and/or function of CCK-8S (SEQ ID NO: 14) or the disappearance thereof causes the appearance of pathologic symptoms such as difficulty in recalling memory to a conscious level and translation into action. Diseases or symptoms accompanying this kind of impairment of memory function can be alleviated by an agonist of the membrane protein receptor of the present invention. Examples of this kind of disease include diseases accompanying impairment of neurologic function such as memory. Specifically for example, dementia and Alzheimer's disease and the like may be mentioned.

The inventors therefore consider that the membrane protein receptor of the present invention participates as a CCK receptor in physiological functions such as anxiety, analgesia, sedation, ingestion suppression, memory and learning, in which CCK involvement has already been postulated. Furthermore, it is reported that CCK exhibits various actions in digestive organs, and it is also considered to be a signaling substance that imparts a sensation of satiety to cerebral neurons. The inventors therefore consider that CCK-8S, a member of the CCK family, also acts as a signaling substance that imparts a sensation of satiety to cerebral neurons. The inventors consider that a quantitative and functional decline in CCK-8S causes obesity due to a decline in a sensation of satiety. The inventors consider that the membrane protein receptor of the present invention is involved in this kind of obesity as a CCK receptor. Further, it is reported that when CCK-8S is administered to diabetes patients, an increase in insulin amounts is promoted and an increase in postcibal glucose amount is suppressed (Bo, A. et al., "The Journal of Clinical Endocrinology & Metabolism", 2000, Vol. 85, pp. 1043-1048). There is thus a possibility that the functional membrane protein receptor of the present invention is associated with diabetes. Accordingly, an agonist or antagonist of the membrane protein receptor of the present invention can alleviate a disease or symptoms accompanying impairment of this kind of physiological function. More specifically, an agonist or antagonist of the membrane protein receptor of the present invention can be used as an active ingredient of an anti-anxiety drug, analgesic preparation or preventive and/or therapeutic agent for a disease caused by various kinds of abnormalities of the central nervous system. Specific examples of these kinds of diseases include dementia, Parkinson's disease, panic syndrome, drug dependence, obesity, diabetes and the like.

More specifically, the inventors consider that the membrane protein receptor of the present invention is involved in neurogenic disease, for example, depression from viewpoints of distribution of the expression of the DNA encoding the receptor protein and results of experiments using knockout mouse of a splicing variant of the DNA.

"Depression" is also referred to as depressive illness and is emotional mental disorder with chief complaints of emotional disturbance such as sorrow feeling or the like, thinking disturbance such as inhibition of thought or the like, hypobulia, behavioral suppression, sleep disorder, daily fluctuation of depression state or the like. It is said that reduction in the neurotransmitter in the brain is responsible for depression. Further, it is said that biological factors, psychological factors, social and environmental factors are involved in the development of this disorder.

"Depression state" refers to symptoms generally observed in depression, for example, emotional disturbance such as sorrow feeling or the like, thinking disturbance such as inhibition of thought or the like, hypobulia, behavioral suppression, sleep disorder or the like.

The expression of a DNA encoding the protein used in the present invention was observed strongly in brain cortex, hippocampus and amygdaloid body as mentioned above (see Example 10 and Table 3). It is reported that amygdaloid body is involved in depression (Whalen P. J. et al., "Seminars in Clinical Neuropsychiatry", 2002, Vol. 7, No. 4, p. 234-242; Drevets W. C. et al., "Annals of the New York Academy of Sciences", 2003, Vol. 985, p. 420-444; Nestler E. J. et al., "Neuron", 2002, Vol. 34, No. 1 p. 13-25).

It has been observed in the tail suspension test using BAI2 gene knockout mouse that the mouse exhibited an anti-depression-like phenotype (see Example 11). BAI2 gene is a splicing variant of the DNA encoding the protein used in the present invention. The tail suspension test is a technique used normally as a test method for investigating a phenotype of depression and is used as the test system for studying the association with depression such as assessment of anti-depressant drug or the like (Steru L. et al., "Psychopharmacology (Berl)", 1985, Vol. 85, No. 3, p. 367-370; Crowley J. J. et al., "Pharmacological Biochemical Behavior", 2004, Vol. 78, No. 2, P. 269-274; Nielsen D. M. et al., "European Journal of Pharmacology", 2004, Vol. 499, Nos. 1-2, P. 135-146).

BAI2 gene knockout mouse showed an anti-depression like phenotype in the tail suspension test, but did not show increase in any behavioral activity in other behavioral examinations. In addition, the knockout mouse did not show any significant difference compared with wild type mouse with respect to many examination items including physiological examination, pathological examination, anatomical examination or the like.

Since BAI2 gene is being destroyed in a BAI2 gene knockout mouse, BAI2 gene and a splicing variant thereof are not expressed. In other words, anti-depressant state was induced in the mouse lacking BAI2 gene and the gene product of a splicing variant thereof. From the result thus obtained, the inventors consider that BAI2 gene and the gene product of a splicing variant thereof are involved in depression.

The inventors consider that even in human, BAI2 gene and a splicing variant thereof, i.e., the DNA encoding the protein used in the present invention and a splicing variant thereof are involved in depression.

Meanwhile, two kinds of GPCRS, CCK-A receptor (also referred to as "CCK1 receptor") and CCK-B receptor (also referred to as "CCK2 receptor"), have been reported as CCK receptors (Herranz, R., "Medicinal Research Reviews", 2003, Vol. 23, No. 5, pp. 559-605, Review). These are both GPCRs belonging to class A (rhodopsin like).

The inventors consider that since ligand affinity and distribution of the expression of the membrane protein receptor according to the present invention are different from those of CCK-A receptor and CCK-B receptor, the present membrane protein receptor carries physiological action different from that of CCK-A receptor and CCK-B receptor. Specifically, the membrane protein receptor has similar ligand affinity as that of CCK-A receptor with different distribution of the expression, and has similar distribution of the expression as that of CCK-B receptor with different ligand affinity.

The inventors consider that since the expression of DNA encoding the protein used in the present invention is high specifically in brain tissues, the membrane protein receptor comprising the protein can participate in action of CCK in the central nervous system in comparison to CCK-A receptor which has low expression in brain tissues. Further, because of the difference in ligand affinity in comparison to CCK-B receptor that is expressed in brain tissues, there is a possibility that the membrane protein receptor of the present invention may exhibit a different activity from CCK-B receptor in the brain.

Further, as mentioned above, anti-depressant state was observed in the knockout mouse of the present protein membrane receptor. In the meantime, there have been some reports describing phenotypes of a knockout mouse of CCK-A receptor gene, a knockout mouse of CCK-B receptor gene and a double knockout mouse of CCK-A receptor gene and CCK-B receptor gene were reported, and it was reported that behavioral activity was enhanced in knockout mouse of CCK-B receptor gene. However, there is no report indicating a possible association between these knockout mice and depression.

The inventors consider that all of the membrane protein receptor according to the present invention, CCK-A receptor and CCK-B receptor are receptors responding to CCK, but the membrane protein receptor alone is a membrane protein receptor associated with depression from viewpoints of their tissue expression distribution and phenotype in the knockout mouse. Further, the inventors consider that CCK-A receptor is not involved in physiological activity of CCK in brain tissue since expression of CCK-A receptor in brain tissue is low. Although CCK-B receptor is expressed in brain tissue, there is no report that suggests possible association between phenotype of knockout mouse of gene encoding CCK-B receptor protein and depression.

CCK-A receptor strongly expresses principally in digestive organs, and its expression is observed in one part of brain. The ligand affinity of CCK-A receptor is strong in the order of CCK-8S>>CCK-8NS, gastrin>CCK-4. Although CCK-A receptor responds strongly to CCK-8S (SEQ ID NO: 14), specificity of CCK-A receptor to the ligand is not observed.

CCK-B receptor expresses widely in brain tissues as well as digestive organs. The ligand affinity of CCK-B receptor is strong in the order of CCK-8S≧CCK-8NS, gastrin>CCK-4, indicating that it has lower selectivity than CCK-A receptor.

As for a phenotype of knockout mouse of CCK-A receptor, in addition to dysfunction in the digestive system such as biliary caculus, pancreatic enzyme secretion and gallbladder contraction or the like, abnormality of homeostasis such as body temperature regulation or the like (Nomoto S. et al., "American journal of physiology. Regulatory integrative and comparative physiology", 2004, Vol. 287, No. 3, R556-61); increase of behavioral activity (Miyasaka K. et al., "Neuroscience Letters", 2002, Vol. 335, No. 2, p. 115-118); and abnormality of appetite regulation (Bi S. et al., "Neuropeptides", 2002, Vol. 36, Nos. 2-3, p. 171-181) have been reported.

As for a phenotype of knockout mouse of CCK-B receptor, in addition to abnormality of the digestive system such as abnormal gastric secretion and gastric mucosa malformation, many reports dealing with a phenotype of central system such as anxiety, pain, memory or the like have been presented (Noble F. et al., "Neuropeptides", 2002, Vol. 36, Nos. 2-3, P. 157-170). More specifically, suppression of anxiety action (Horinouchi Y. et al., "European Neuropsychopharmacology", 2004, Vol. 14, No. 2, p. 157-161); increased anxiety action (Miyasaka K. et al., "Neuroscience Letters", 2002, Vol. 335, No. 2, p. 115-118); increase in behavioral activity and memory impairment (Dauge V et al., "Neuropsychopharmacology", 2001, Vol. 25, No. 5, p. 690-698); dysalgesia and correlation with opioid system (Kurrikoff K. et al., "The European Journal of Neuroscience", 2004, Vol. 20, No. 6, p. 1577-1586) or the like have been reported.

Further, there are some reports about a phenotype of double knockout mouse of CCK-A receptor and CCK-B receptor, but any phenotype characteristic to double knockout mouse has not been reported (Miyasaka K. et al., "Neuroscience Letters", 2002, Vol. 335, No. 2, p. 115-118).

The inventors consider that a DNA encoding the protein used in the present invention. i.e., the DNA represented by the base sequence described in SEQ ID NO: 1 and a homolog of the DNA, are involved in depression. For example, the inventors consider that depression state and depression are induced by such an abnormality that expression of the DNA represented by the base sequence described in SEQ ID NO: 1 or a homolog of the DNA is increased.

Since it can be considered that the DNA represented by the base sequence described in SEQ ID NO: 1 and a homolog of the DNA are involved in depression, it is possible to improve depression state and to recover depression by inhibiting a function and/or expression of any one of proteins selected from the group consisting of the protein being encoded by the DNA and a splicing variant of the protein.

The present invention relates to a method for improving depression state by inhibiting the function and/or expression of any one of proteins selected from the group consisting of the protein being encoded by the DNA represented by the base sequence described in SEQ ID NO: 1 and a homolog of the protein.

The phrase "improving depression state" means that depression state is alleviated or cured compared with a state before improvement of depression state is attempted. For example, this means that emotional disturbance, thinking disturbance, hypobulia, behavioral suppression, sleep disorder or the like is alleviated or cured.

Inhibition of the function and/or expression of the protein used in the present invention can be executed by, for example, a compound that inhibits the function and/or expression of the protein.

In the present specification, the phrase "a compound inhibiting a function of the protein used in the present invention" and "an antagonist of the protein" are used interexchangeably. In the present specification, "an antagonist" may be any compound that inhibits the function of the protein used in the present invention, and for example, a compound that binds to a receptor and inhibits an effect of an agonist, but is unable to exert an effect that is exhibited by the agonist even after the binding of itself to the receptor, a compound that inhibits binding of a ligand to a receptor, or a compound that acts as an inverse agonist may be mentioned. In recent years, it has been known that a receptor such as GPCR is converted from active type to inactive type irrespective of an action of a ligand, or from inactive type to active type. In this specification, a substance that inhibits a step where a receptor such as GPCR is converted from inactive type to active type irrespective of an action of a ligand is referred to as an inverse agonist. It can be considered that the inverse agonist of the present protein also inhibits the function of the protein used in the present invention.

The antagonist of the protein used in the present invention binds to a membrane protein receptor comprising the protein and inhibits an effect of a ligand. Since it is considered that depression state and depression are induced by an abnormality such as increase in expression of the DNA encoding the protein, the inventors consider that depression state and depression can be improved by inhibiting an action of a ligand to a receptor comprising the protein by the antagonist of the protein.

Thus, it is considered that the antagonist of the protein used in the present invention has an anti-depressant action. "Anti-depressant action" refers to an effect that improves depression state.

A compound that inhibits the function of the protein used in the present invention, for example, the antagonist of the protein is preferably an antagonist that inhibits the function caused by CCK-8S through the membrane protein receptor comprising the protein. Further, the antagonist may be an antagonist that inhibits the function caused by a peptide having an equivalent function to that of CCK-8S through the membrane protein receptor comprising the protein.

The antagonist of the protein used in the present invention can be obtained by a method for identifying a compound which will be explained later. As the antagonist of the protein if a ligand of the membrane protein receptor comprising the protein is a protein, a substance that is a partial peptide of the ligand and binds to the membrane protein receptor, but is unable to exert an effect that is exhibited by the ligand, can be used. A partial peptide of a ligand of the membrane protein receptor can be obtained in such that after the ligand is identified, a number of partial peptides are designed and synthesized from the amino acid sequence thereof, and those having activity as the antagonist are selected from synthesized partial peptides by a method for identifying a compound which will be explained later.

As the antagonist of the protein used in the present invention, three kinds of compounds (structural formula (I), (II) and (III)) identified by a method for identifying a compound which will be explained later can be exemplified (see Example 12).

Structural Formula (I):

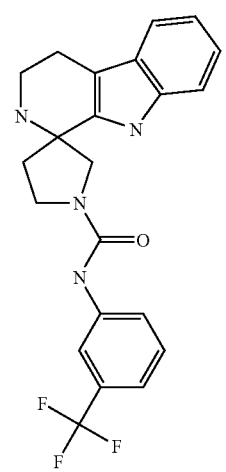

Structural Formula (II)

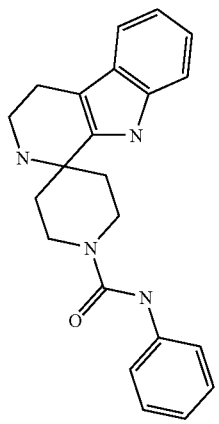

Structural Formula (III)

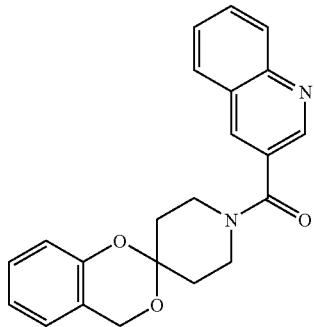

Further, the present invention can provide an agent for improving depression state comprising a compound that inhibits the function and/or expression of any one of proteins selected from the group consisting of a protein encoded by the DNA represented by the base sequence described in SEQ ID NO: 1 of the sequence listing and a splicing variant of the protein. Hereunder, the agent for improving depression state may be referred to as the anti-depressant drug.

"An agent for improving depression state" or "antidepressant drug" refers to a drug having an effect for improving depression state.

(Method for Identifying a Compound)

A method for identifying a compound that inhibits the function of the protein used in the present invention can be carried out utilizing a known pharmaceutical screening system using at least one of the protein, DNA, recombinant vector, transformant, or antibody. According to the identification method, it is possible to conduct screening for an antagonist by drug design based on three-dimensional structure of the protein, screening for an inhibitor or promoter of expression at the gene level utilizing a protein synthesis system, or screening for an antibody-recognizing substance utilizing the antibody.

The method for identifying a compound that inhibits the function of the protein used in the present invention can be used as a method for identifying a compound having anti-depressant action. More preferably, the identification method can be used as a method for identifying a compound having an anti-depressant action that is an antagonist of any one of proteins selected from the group consisting of a protein encoded by the DNA represented by the base sequence described in SEQ ID NO: 1 of the sequence listing and a homolog of the protein. It can be carried out to confirm whether or not the compound exhibits an anti-depressant action, by using a test method generally used for anti-depressant action, for example, using a tail suspension test or a forced swimming test using a mouse. Specifically, if immobility time of a mouse administered with the compound is shortened in the tail suspension test compared with that of a mouse not administered with the compound, it can be determined that the compound has an anti-depressant action. Such a compound is useful as an anti-depressant drug.

Identification of a compound that inhibits the function of the protein used in the present invention can be carried out by using, specifically, for example, an experimental system capable of measuring a function of the protein. The identification method can be carried out in the experimental system under conditions that allows for the interaction of the protein and a compound to be tested (hereunder referred to as "the test compound") by bringing the protein coexist with the test compound, measuring the function thereof, and then detecting changes (decrease, increase, disappearance or appearance) in a function of the protein in comparison to the results obtained in the absence of the test compound. The effect of the test compound that exerts on the function of the protein can be determined by comparing a function of the protein in the presence of the test compound with a function of the protein in the absence of the test compound. For example, if a function of the protein in the presence of the test compound is decreased compared with a function of the protein in the absence of the test compound, it can be determined that the test compound has an action to inhibit a function of the protein.

As a function of the protein used in the present invention, binding to a ligand, activation of intracellular signal transduction mechanism and induction of cell response can be exemplified, since the protein functions as a membrane protein receptor. More specifically, binding to CCK-8S (SEQ ID NO: 14) and interaction with MAGUK family proteins or the like can be exemplified.

A method for identifying a compound that inhibits the binding of the protein used in the present invention to a ligand of the protein can be conducted by performing the reaction between the protein and the ligand of the protein in the presence or absence of the test compound and then measuring the binding between the protein and the ligand. The protein used in the identification method can be a protein that expressed in a cell membrane of a cell containing a DNA encoding the protein. The cell may be a transformant obtained by transfecting with a vector containing a DNA encoding the protein. Measurement of the binding between the protein and a ligand of the protein can be performed utilizing various kinds of binding assays that are used in an ordinary pharmaceutical screening system. For example, measurement can be carried out by performing a binding reaction between the ligand and the protein; separating a complex formed by binding of the protein to the ligand from the unbound isolated ligand and the protein; and detecting the complex by a known method such as immunoblotting or the like. Further, measurement of binding can be carried out by performing a binding reaction between the ligand and the protein, and then measuring the ligand bound to the protein using an anti-ligand antibody. The anti-ligand antibody bound to the ligand can be detected using a secondary antibody labeled with HRP or biotin or the like. The ligand bound to the protein can also be detected using an anti-ligand antibody that is previously labeled with HRP or biotin or the like. Alternatively, the ligand bound to the protein can be measured by performing the above described identification method using a ligand that was previously labeled with a desired labeling substance as the ligand for use in the binding reaction with the protein, and then detecting the labeling substance. Any substance that is used in an ordinary binding assay can be utilized as the labeling substance, which is exemplified by GST, tag peptides such as His-tag, Myc-tag, HA-tag, FLAG-tag or Xpress-tag or the like, or fluorescence dye or the like. As a simple and convenient method, a radioactive isotope can be utilized.

The compound, which is obtained by a method for identifying a compound that inhibits the binding between the protein used in the present invention and a ligand of the protein, can be a compound that inhibits the function of the membrane protein receptor, since the protein is a membrane protein receptor.

The compound, which inhibits the binding between the protein used in the present invention and a ligand of the protein and inhibits a function of a membrane protein receptor comprising the protein, can be used as an antagonist of the membrane protein receptor. It can be determined whether or not the compound is a compound that inhibits the function of the membrane protein receptor of the present invention, by conducting a measurement of a change in the function of the membrane protein receptor caused by ligand in the presence and absence of the compound. When a change in function of the membrane protein receptor is not caused due to a compound, it can be determined that the compound is either a compound that binds to the membrane protein receptor, but does not induce a cell reaction through the membrane protein receptor, or a compound that acts on a ligand and inhibits the binding between the ligand and the membrane protein receptor. In contrast, when the change in function of the membrane protein receptor due to a compound is equivalent to a change in functions of the membrane protein receptor caused by ligand such as CCK-8S (SEQ ID NO: 14), it can be determined that the compound is an agonist that binds to the membrane protein receptor and induces cell response via the membrane protein receptor.

As a method for measuring a function of the protein used in the present invention, an experimental method using a transformant that expressed the protein may be mentioned which comprises allowing a ligand to act to the protein after contacting the transformant and a test compound, or in the presence of the transformant and the test compound, and then measuring a change in a biological response produced in the transformant.

The method for measuring a function of the protein used in the present invention can be utilized, for example, to carry out a method for identifying a compound that activates intracellular signal transduction mechanism or inhibits induction of a cell response. It is possible to select a compound that inhibits the function of the protein by detecting a change in function (decrease, increase, disappearance or appearance) in comparison with measurement results taken in the absence of a test compound. As a change in cell response generated in the transformant in which the protein is expressed, for example, a change in cell membrane potential or in intracellular calcium concentration or the like may be mentioned. When a change such as a decrease in cell membrane potential of the transformant or a decrease in intracellular calcium concentration is caused, it can be determined that the test compound inhibits the function of the protein. Measurements of a change in cell membrane potential and in intracellular calcium concentration can be carried out using a known method. Further, measurement of a function of the protein can be carried out by measuring the interaction with a MAGUK family protein.

Measurement of a change in interaction with a MAGUK family protein or measurement of a change in binding to a G protein can be carried out using a known method.

Actually, by using an experimental system for measuring a cell response using a cell transfected with a vector containing the DNA represented by the base sequence described in SEQ ID NO: 1 of the sequence listing, identification of a compound that exhibits an inhibitory effect to the cell response was conducted (see Example 12). In the experimental system, a cell response was induced by allowing CCK-8S to act with the cell and measurement of cell response was performed by measuring a change in intracellular calcium concentration. As the test compound, SoftFocus GPCR Target-Directed Library (BioFocus) that is a compound library was used. As a result, three kinds of compounds that inhibit a cell response of the cell to CCK-8S were identified (aforementioned structural formulae (I), (II) and (III)). The inventors consider that these compounds act as an antagonist of a protein encoded by DNA represented by the base sequence described in SEQ ID NO: 1.

From the results thus obtained, the inventors consider that it is possible to identify an antagonist that inhibits a response to a ligand of the protein used in the present invention, such as CCK-8S, by using an experimental system using a transformant in which the protein used in the present invention is expressed, for example, by a system using the transformant which measures a change in an intracellular calcium concentration.

A method for identifying a compound that can affect interaction between the protein used in the present invention and MAGUK family protein can be carried out, for example, by using the protein being isolated and MAGUK family protein and detecting a binding between the protein and MAGUK family protein by a known protein binding assay. More specifically, a MAGUK family protein is, for example, expressed as a GST-tag fusion protein according to a genetic engineering technique, then bonded to glutathione-sepharose, after which the amount of the protein binding thereto can be quantified using an antibody against the protein, for example an antibody that was labeled with an enzyme such as HRP or ALP, a radioactive isotope, a fluorescent substance, or biotin or the like. When the protein is fused with a tag peptide and used, the amount of binding can be determined using an anti-tag antibody. Naturally, the protein may also be directly labeled with the above described enzyme, radioactive isotope, fluorescent substance, or biotin or the like. Alternatively, a secondary antibody that was labeled with the above described enzyme, radioactive isotope, fluorescent substance, or biotin or the like may be used. As a further alternative, DNA encoding the protein and DNA encoding a MAGUK family protein may be co-expressed using a suitable cell, whereby the interaction of the two substances can be measured by detecting binding between the two substances using a pull-down method.

A method of identifying a compound that affects interaction between a protein used in the present invention and a MAGUK family protein can also be carried out, for example, by using a two-hybrid method to introduce into a yeast or a eukaryotic cell or the like a plasmid expressing the protein and a DNA binding protein as a fusion protein, a plasmid expressing a MAGUK family protein and a transcription-activating protein as a fusion protein, and a plasmid containing a reporter gene such as lacZ connected to an appropriate promoter gene, and comparing the expression amount of the reporter gene when allowed to coexist with the test compound and the expression amount of the reporter gene in the absence of the test compound. When the expression amount of the reporter gene when allowed to coexist with the test compound decreased in comparison to the expression amount of the reporter gene in the absence of the test compound, it can be determined that the test compound has an action that inhibits binding between the protein and the MAGUK family protein. In contrast, when the expression amount of the reporter gene when allowed to coexist with the test compound increased in comparison to the expression amount of the reporter gene in the absence of the test compound, it can be determined that the test compound has an action that stabilizes binding between the protein and the MAGUK family protein.

Identification of a compound that affects interaction between a protein used in the present invention and a MAGUK family protein can also be performed using a surface plasmon resonance sensor such as the BIACORE system.

Further, identification of a compound that affects interaction between a protein used in the present invention and a MAGUK family protein can be carried out using a method that applies a scintillation proximity assay (SPA) or fluorescence resonance energy transfer (FRET).

Specific examples of a MAGUK family protein used in the identification method according to the present invention include DLG2, DLG3 and DLG4, or AIP1 and MAGI3. As long as there is no affect on the interaction with the protein used in the present invention, the MAGUK family protein may be one in which a segment thereof was deleted or one to which a labeling substance such as another protein was attached.

The method for identifying a compound that inhibits expression of the protein used in the present invention can be carried out utilizing a known pharmaceutical screening system using at least one of the DNA, recombinant vector and transformant.

The method for identifying a compound that inhibits expression of the protein used in the present invention can be used as a method for identifying a compound that has anti-depressant action. That is, since a compound obtained by the identification method is considered to have anti-depressant action, it can be used as anti-depressant drug.

The method for identifying a compound that inhibits the expression of the protein used in the present invention can be carried out in an experimental system in which it is possible to measure expression of the DNA used in the present invention, by allowing the DNA and a test compound to coexist and measuring the expression thereof, and then detecting a change (decrease or disappearance) of the expression in comparison with results of measurements taken in the absence of the test compound. Measurement of the expression of the protein can be performed by directly detecting a protein encoded for by the DNA, or can be carried out, for example, by introducing a signal as an indicator of the expression into an experimental system and detecting the signal. As a signal, a tag peptide such as GST, His-tag, Myc-tag, HA-tag, FLAG-tag or Xpress-tag, or a fluorescent dye can be used.

Specifically, the method for identifying a compound that inhibits the expression of the protein used in the present invention can be carried out, in an experimental system in which the protein is expressed by using a transformant to which an expression vector containing DNA used in the present invention is transfected, by contacting the transformant with a test compound followed by measuring an expressed protein. It is possible to select a compound that inhibits the expression of the protein by detecting a change in expression (decrease, or disappearance) in comparison with measurement results taken in the absence of a test compound. Detection of the presence or absence of, or a change of the protein can be carried out by a known protein detection method, for example, Western blotting or the like. Further, detection of the presence or absence of, or a change in expression of the protein can be carried out by employing an indicator such as a biological function of the protein to be expressed or a cell response via the protein, for example, interaction with MAGUK family protein that is generated when a ligand is allowed to act thereon, a change in cell membrane potential and a change in intracellular calcium concentration.

Identification of a compound that affects expression of the DNA of the used in the present invention can also be carried out by, for example, producing a vector in which a reporter gene is connected instead of the DNA downstream of a promoter region of a gene including the DNA, contacting a cell, for example, a eukaryotic cell, containing the vector with the test compound, and determining the presence or absence of, or a change in, expression of the reporter gene. A gene that is ordinarily used in a reporter assay can be used as the reporter gene, and for example, a gene having an enzyme activity such as luciferase, β-galactosidase or chloramphenicol acetyl transferase may be mentioned. Detection of expression of the reporter gene can be carried out by detecting the activity of the gene product, for example, in the case of the reporter genes exemplified above, the enzyme activity.

The method for identifying a compound that promotes a function or expression of the protein used in the present invention can be carried out utilizing an experimental system or a measuring system that is used in the aforementioned identification method. For example, the method for identifying a compound that promotes a function of the protein can be carried out utilizing an experimental system for measuring the binding between the protein and a ligand of the protein, a method for measuring a function of the protein, and an experimental system for measuring the binding between the protein and MAGUK family protein. Further, the method for identifying a compound that promotes expression of the protein can be carried out utilizing an experimental system capable of measuring expression of the DNA used in the present invention.

When a function or expression of the protein is increased or generated by the test compound, it can be determined that the test compound promotes a function and expression of the protein.

The method for identifying an agonist of the membrane protein receptor can be carried out utilizing an experimental system or a measuring system used in the identification method. As the identification method of an agonist of the membrane protein receptor, for example, such a method may be mentioned which uses an experimental system using the transformant in which the protein is expressed and comprises contacting the transformant with a test compound or allowing the transformant coexist with a test compound followed by measuring a change in function produced in a transformant. It is possible to select an agonist of the membrane protein receptor by detecting a change in the function of the membrane protein receptor, for example, decrease, increase, disappearance, appearance or the like, in comparison with measurement results taken in the absence of a test compound. An agonist can be selected more preferably by comparing the functional change with the functional change observed by measuring a change in function of the membrane protein receptor caused by a ligand of the membrane protein receptor such as CCK-8S (SEQ ID NO: 14). Preferably, the agonist is a compound that brings about a functional change in the membrane protein receptor that is equivalent to a functional change produced in the membrane protein receptor by a ligand such as CCK-8S (SEQ ID NO: 14). It is sufficient that a functional change produced in the membrane protein receptor by an agonist is equivalent to a functional change produced in the membrane protein receptor by a ligand such as CCK-8S (SEQ ID NO: 14), and there may be a quantitative difference. For example, a functional change produced in the membrane protein receptor by an agonist may be weaker than a functional change produced in the membrane protein receptor by a ligand such as CCK-8S (SEQ ID NO: 14). An agonist is preferably selected that induces a functional change in the same degree as that induced by CCK-8S (SEQ ID NO: 14). The functional change of the membrane protein receptor can be measured by employing a change in cell response via the membrane protein receptor of the transformant as an indicator. Accordingly, as a functional change that is equivalent to a functional change produced in the membrane protein receptor by a ligand such as CCK-8S (SEQ ID NO: 14), for example, an increase in intracellular calcium concentration via the membrane protein receptor in a transformant can be mentioned. Measurement of a change in intracellular calcium concentration can be carried out using a known method (see Example 5). In addition, as a functional change that is equivalent to a functional change produced in the membrane protein receptor by a ligand such as CCK-8S (SEQ ID NO: 14), a change in membrane potential via the membrane protein receptor in a transformant can be mentioned. Measurement of a change in membrane potential can be carried out using a known method (see Example 3). With respect to the ligand, either a sample including the ligand or the ligand itself that was obtained by the above described method of identifying a ligand can be used. Since it can be considered that CCK-8S (SEQ ID NO: 14) may be an in vivo ligand of the protein, the use of CCK-8S (SEQ ID NO: 14) as a ligand is preferred. CCK-8S (SEQ ID NO: 14) can be produced by a common chemical synthesis method. Further, it can also be synthesized using a commercially available peptide synthesis apparatus.

The method for identifying an agonist of the membrane protein receptor can also be carried out by determining whether or not a compound obtained by a method for identifying a compound that binds to the membrane protein receptor induces a functional change in the membrane protein receptor using the above described identification method.

Identification of a ligand of a membrane protein receptor comprising the protein used in the present invention can be carried out by utilizing an experimental system and measuring system that is used in the aforementioned identification method. For example, it can be carried out by detecting the binding between a substance to be examined (hereunder, referred to as "test substance") and the protein by a known binding assay. Alternatively, in the identification method using cells in which the protein is expressed, it can be carried out by measuring a cell response of the cell induced when contacting the test substance with the protein. In the case the cell response when contacting the test substance with the protein changed (was promoted, occurred, decreased, or disappeared) in comparison to that when not contacting the test substance, it can be determined that the test substance is a ligand or includes a ligand. Specific examples of the cell response include a change in cell membrane potential or a change in intracellular calcium concentration. Measurement of cell membrane potential or intracellular calcium concentration can be carried out by a known method. Alternatively, in an identification method using cells that express the protein, the target ligand can be obtained by measuring the interaction between the protein and a MAGUK family protein as an indicator for the cell response. In the case the interaction between the protein and a MAGUK family protein in the cell when contacting the test substance with the protein changed (was promoted or occurred) in comparison to that when not contacting the test substance, it can be determined that the test substance is a ligand or includes a ligand. Interaction between the protein and a MAGUK family protein can be detected by a known method such as immunoblotting.

As a test substance which may be an object for identifying a ligand, for example, a sample prepared from a cell or biomedical tissue in which expression of the DNA used in the present invention was observed may be mentioned. Alternatively, various compounds that were derived from natural products or synthesized can be taken as an object.

This kind of identification method is useful for determining whether or not a ligand is included in a sample. The identification method can also be effectively used in a process for purifying the ligand from a sample which was determined to contain the ligand. For example, when fractionating and purifying a sample using gel filtration chromatography or the like, it is possible to determine whether or not a ligand is included in the fraction product.

(Compounds)

Compounds identified by the identification method according to the present invention can be utilized as inhibitors, antagonists, promoters or stabilizers or the like of a function of the protein, for example, binding to a ligand, activation of intracellular signal transduction, or induction of a cellular response. Furthermore, the compounds can also be utilized as expression inhibitors or expression promoters with respect to the protein at the gene level. These compounds can be prepared as medicines by performing further screening which takes into consideration the balance between bioavailability and toxicity. Further, it can be anticipated that these compounds will produce a preventive effect and/or therapeutic effect for various kinds of pathologic symptoms attributable to an abnormality in a function of the protein and/or expression of DNA encoding the protein.

(Pharmaceutical Composition)

The protein, DNA, recombinant vector, transformant, antibody, ligand and compound used in the present invention is useful as an active ingredient of a medicine or pharmaceutical composition that is based on inhibiting, antagonizing, or promoting a function and/or expression of the protein.

A medicine or pharmaceutical composition used in the present invention can be used as a preventive agent and/or therapeutic agent for a disease attributable to an abnormality in a function of a protein used in the present invention and/or the expression of DNA encoding the protein. The medicine or pharmaceutical composition can also be used in a method for preventing and/or method for treating such disease.

When a function of a protein used in the present invention and/or expression of DNA encoding the protein is excessive, as one method, an effective dose of the inhibitor that inhibits the function of the protein and/or expression of the DNA can be administered to a subject together with a pharmaceutically acceptable carrier to inhibit the function of the protein and thereby improve the abnormal symptoms. Further, expression of DNA encoding the integral protein may be inhibited using an expression block method. For example, expression of DNA encoding the protein can be inhibited by using a fragment of the DNA as an antisense oligonucleotide in gene therapy. Not only DNA fragments used as an antisense oligonucleotide that correspond to a coding region of the DNA, but also those that correspond to a noncoding region thereof are useful. In order to specifically inhibit expression of the DNA, the base sequence of a characteristic region of the DNA is preferably used.

For treatment of abnormal symptoms related to a decrease or deficiency of a function of a protein used in the present invention and/or expression of DNA encoding the protein, as one method, a method may be mentioned in which an effective dose of a promoter that promotes or stabilizes the function of the protein and/or expression of the DNA is administered together with a pharmaceutically acceptable carrier thereby to improve the abnormal symptoms. Alternatively, the protein may be produced intracellularly within the subject using gene therapy. A known method can be utilized for the gene therapy that utilizes the DNA of the present invention. For example, a method can be applied in which the DNA or a replication-defective retrovirus vector incorporating the RNA as the transcription product of the DNA is produced, a cell originating from the subject is treated ex vivo using the vector, and the cell is then introduced into the subject.

The inventors found that tissue expression of DNA comprising the base sequence represented by SEQ ID NO: 1 of the sequence listing as one form of the DNA used in the present invention is specifically high in the overall brain, for example, brain cortex, hippocampus, and amygdaloid body. Accordingly, the inventors considered that the protein used in the present invention, the DNA and the protein are important for homeostatic maintenance of the brain and brain cells. Further, expression thereof that is noticeably high in comparison to normal tissue has been observed in tumors such as ovarian cancer, liver cancer, and adrenal cancer. The inventors therefore considered that the present protein, the DNA and the protein are involved in these tumor diseases.

A protein used in the present invention has a TSP-I domain in the amino acid sequence thereof. Since it is reported that the TSP-I domain is a domain that is responsible for an angiogenesis inhibiting function, the inventors considered that the protein has an angiogenesis inhibiting function. Accordingly, there is a possibility that the protein is involved in diseases caused by angiogenesis inhibition or diseases accompanying angiogenesis inhibition. In such a disease, the treatment thereof can be performed by promoting angiogenesis, therefore the function or expression of the protein is preferably inhibited. Examples of these diseases include cerebral contusion and cerebral infarction. In this case, improvement, prevention and/or treatment of the disease can be carried out by a compound having a function that reduces or eliminates a function and/or expression of the protein. More specifically, a pharmaceutical composition comprising an effective dose of a compound that inhibits a function and/or expression of the protein can be used as an improving agent, preventive agent and/or therapeutic agent for a disease caused by angiogenesis inhibition or a disease accompanying angiogenesis inhibition (for example, cerebral contusion or cerebral infarction). Further, a method for preventing and/or a method for treating such disease can be carried out using these.

In contrast, there is a possibility that a decrease in a function and/or expression of the protein used in the present invention is associated with diseases caused by angiogenesis or diseases accompanying angiogenesis. Examples of these diseases include tumor diseases that are known to accompany angiogenesis. In such case, improvement, prevention, and/or treatment can be carried out using the present protein, the DNA or a compound that promotes a function of the protein and/or expression of the DNA. More specifically, a pharmaceutical composition comprising an effective dose of the present protein, the DNA or a compound that promotes a function of the protein and/or expression of the DNA can be used as improving agent, preventive agent, and/or therapeutic agent for a disease caused by angiogenesis or a disease accompanying angiogenesis (for example, a tumor disease). Further, a method for preventing and/or a method for treating such disease can be carried out using these.

It is reported that CCK-8S (SEQ ID NO: 14) that was found as a ligand of the functional membrane protein receptor of the present invention is essential for memory retention, for example, that it is difficult to recall memory to a consciousness level and translate it into action in the absence of CCK-8S (SEQ ID NO: 14). The inventors therefore considered that the functional membrane protein receptor of the present invention is involved in the neurologic function of CCK-8. Further, since a relationship between CCK-B receptor and anxiety has been reported, there is a possibility that the functional membrane protein receptor of the present invention is similarly related with anxiety disorder. Accordingly, the inventors considered that an agonist of the functional membrane protein receptor of the present invention and a pharmaceutical composition comprising an effective dose of the agonist is effective in alleviating, improving, preventing and/or treating diseases or symptoms accompanying impairment of neurologic functions such as memory as well as anxiety disorders and the like. Specific examples of diseases accompanying impairment of neurologic functions such as memory include dementia (including Alzheimer's disease). Furthermore, it is reported that CCK exhibits various kinds of actions in digestive organs, and it is also considered to be a signaling substance that imparts a sensation of satiety to cerebral neurons. The inventors therefore considered that CCK-8S, a member of the CCK family, also acts as a signaling substance that imparts a sensation of satiety to cerebral neurons. A quantitative and functional decrease in CCK-8S is considered to bring about obesity due to a decrease in a sensation of satiety. Further, it is reported that when CCK-8S is administered to diabetes patients, an increase in insulin amount is promoted and an increase in postcibal glucose amount is suppressed (Bo, A. et al., "The Journal of Clinical Endocrinology & Metabolism", 2000, Vol. 85, pp. 1043-1048). There is thus a possibility that the functional membrane protein receptor of the present invention is associated with diabetes. Accordingly, the inventors considered that an agonist of the functional membrane protein receptor of the present invention and a pharmaceutical composition comprising the agonist are effective in improving, preventing, and/or treating diabetes or obesity. More specifically, an agonist of the functional membrane protein receptor of the present invention and a pharmaceutical composition comprising the agonist can be used as improving agents, preventive agents and/or therapeutic agents for a disease or symptoms accompanying impairment of memory function (for example, dementia (including Alzheimer's disease)), as well as diabetes and obesity. Further, a method for preventing and/or method for treating such disease can be carried out using these.

Further, as diseases attributable to abnormality of a function of the protein used in the present invention and/or of expression of DNA encoding the protein, neurogenetic disease, for example, depression is preferably mentioned. Expression of the protein is strongly observed in the brain tissue, particularly in brain cortex, hippocampus, and amygdaloid body, and it coincides with distribution of CCK that may be a ligand of functional membrane protein receptor comprising the protein. It is known that CCK is involved in psychological functions such as anxiety, analgesia, sedation, food intake control, memory and learning. Besides, in the tail suspension test using knockout mouse of BAI2 gene, the mouse exhibited an anti-depressant-like phenotype. BAI2 gene is a splicing variant of DNA encoding the protein. Therefore, the inventors consider that a splicing variant of DNA encoding the protein is involved in depression. The inventors consider that, for example, depression is induced by such an abnormality that expression of DNA encoding the protein or of a splicing variant of the DNA is increased.

The inventors consider that an inhibitor for a protein function used in the present invention and/or expression, for example, an antagonist of membrane protein receptor comprising the protein, and a pharmaceutical composition containing an effective dose of the inhibitor are effective for alleviation, improvement, prevention and/or treatment of depression. The medicine or pharmaceutical composition according to the present invention can be used for preventing and/or treating depression. Specifically, the medicine or pharmaceutical composition can be an agent for preventing and/or treating depression containing an effective dose of the inhibitor for the function and/or the expression of the protein used in the present invention, for example, an antagonist of membrane protein receptor comprising the protein. In other words, the medicine or pharmaceutical composition can be an agent for preventive and/or treating depression containing an effective dose of the aforementioned anti-depressant drug. It is possible to conduct prevention and/or treatment of depression by applying the aforementioned anti-depressant drug.

As a disease attributable to abnormality of the function of the protein used in the present invention and/or the expression of DNA encoding the protein, a disease attributable to angiogenesis inhibition and a disease accompanying angiogenesis inhibition may be additionally mentioned, since the protein has TSP-I domain in the amino acid sequence. It is reported that TSP-I domain is a domain responsible for angiogenesis inhibiting function. Therefore, it is considered that the protein has an angiogenesis inhibiting function. Accordingly, there is a possibility that the protein is involved in a disease caused by angiogenesis inhibition or a disease accompanying angiogenesis inhibition. In such a disease, the treatment thereof can be performed by promoting angiogenesis, therefore the function or expression of the protein is preferably inhibited. Examples of these diseases include cerebral contusion and cerebral infarction.

For treatment of abnormal symptoms related to a decrease or deficiency of a function of a protein used in the present invention and/or expression of DNA encoding the protein, as one method, a method may be mentioned in which an effective dose of a promoter that promotes or stabilizes the function of the protein and/or expression of the DNA is administered together with a pharmaceutically acceptable carrier thereby to improve the abnormal symptoms. Alternatively, the protein may be produced intracellularly within the subject using gene therapy. A known method can be utilized for the gene therapy that utilizes the DNA used in the present invention. For example, a method can be applied in which the DNA or a replication-defective retrovirus vector incorporating the RNA as the transcription product of the DNA is produced, a cell originating from the subject is treated ex vivo using the vector, and the cell is then introduced into the subject.

A medicine according to the present invention may be prepared as a medicine comprising an effective dose of at least one member of the group consisting of the aforementioned protein, the aforementioned DNA, the aforementioned recombinant vector, the aforementioned transformant, the aforementioned antibody, the aforementioned ligand, or the aforementioned compound. It is normally preferable to prepare the medicine as a pharmaceutical composition comprising one or more pharmaceutical carriers.

The amount of active ingredient comprised in a pharmaceutical preparation according to the present invention can be suitably selected from a wide range, and a suitable range is normally from approximately 0.00001 to 70 wt %, preferably from about 0.0001 to 5 wt %.

Examples of the pharmaceutical carrier include a diluent or an excipient, such as a filler, an expander, a binding agent, a humidifying agent, a disintegrant, a surfactant and a lubricant that are ordinarily used in accordance with the form of use of the formulation. These may be suitably selected and used in accordance with the administration form of the formulation to be obtained.

For example, water, pharmaceutically acceptable organic solvents, collagen, polyvinyl alcohol, polyvinyl pyrrolidone, carboxyvinyl polymer, sodium alginate, water-soluble dextran, sodium carboxymethyl starch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol and lactose may be mentioned. These may be used independently or in combinations of two or more kinds in accordance with the dosage form.

As desired, the formulation can be prepared by appropriately using various ingredients that can be used for a normal protein formulation, such as a stabilizer, a fungicide, a buffer, a tonicity adjusting agent, a chelating agent, a pH adjustor and a surfactant.

As a stabilizer, for example, human serum albumin, an ordinary L-amino acid, a saccharide, a cellulose derivative or the like may be mentioned, and can be used alone or in combination with a surfactant or the like. In particular, in some cases the stability of an active ingredient can be enhanced by this combination. The above described L-amino acid is not particularly limited and, for example, may be any of glycine, cysteine, glutamic acid and the like. The saccharide is also not particularly limited and, for example, may be a monosaccharide such as glucose, mannose, galactose or fructose, a sugar alcohol such as mannitol, inositol or xylitol, a disaccharide such as sucrose, maltose or lactose, a polysaccharide such as dextran, hydroxypropyl starch, chondroitin sulfuric acid or hyaluronic acid, or a derivative of these or the like. The cellulose derivative is not particularly limited and, for example, may be any of methyl cellulose, ethyl cellulose, hydroxyethyl cellulose, hydroxypropyl cellulose, hydroxypropyl methylcellulose, sodium carboxymethylcellulose and the like. The surfactant is also not particularly limited and, for example, any ionic or nonionic surfactant can be used. These include, for example, polyoxyethylene glycol sorbitan alkyl esters, polyoxyethylene alkyl ethers, sorbitan monoacyl esters, fatty acid glycerides and the like.

Examples of the buffer include boric acid, phosphoric acid, acetic acid, citric acid, ε-aminocaproic acid, glutamic acid and/or salts corresponding to these (for example, an alkali metal salt or an alkali earth metal salt of these, such as a sodium salt, potassium salt, calcium salt or magnesium salt).

Examples of the tonicity adjusting agent include sodium chloride, potassium chloride, a saccharide, and glycerin.

Examples of the chelating agent include edetate sodium and citric acid.

The medicine and pharmaceutical composition of this invention can be used as a solution formulation, and it can also be used after subjecting the solution formulation to lyophilization to obtain the medicine or pharmaceutical composition in a state that can be preserved, and then dissolving the lyophilized product in a buffer solution containing water or a physiological saline solution or the like to prepare it to a suitable concentration just before use.

The dosage range of the pharmaceutical composition is not particularly limited, and can be suitably selected according to the effectiveness of the ingredients contained therein, the dosage form, route of administration, kind of disease, characteristics of the subject (weight, age, condition of the disease, use of other medicines and the like), and the judgment of the attending physician. In general, a suitable dosage is, for example, in the range of approximately 0.01 μg to 100 mg per 1 kg of body weight of the subject, and a preferable dosage is within the range of approximately 0.1 μg to 1 mg per 1 kg of body weight. However, these dosages can be altered using conventional experiments for optimization of a dosage that are well known in the art. The above dosage can be administered once per day or can be divided for administration several times per day, and may also be administered intermittently at the rate of once every several days or several weeks.

When administering the pharmaceutical composition according to the present invention, the pharmaceutical composition may be used alone or may be used with another compound or medicine necessary for the treatment.

Either systemic administration or local administration can be selected as the administration route. In this case, a suitable administration route is selected in accordance with the disease and symptoms and the like. For example, as examples of parenteral administration, in addition to ordinary intravenous injection and intra-arterial administration, subcutaneous administration, intracutaneous administration and intramuscular administration may be mentioned. Oral administration is also possible. Further, transmucosal administration or dermal administration can be carried out. In the case of use for a cancerous disease, preferably direct administration is performed by injection into the tumor.

Various forms can be selected as the form of administration according to the purpose.

Typical examples thereof include a solid administration form such as a tablet, pill, powder, powdered drug, subtle granule, granule or capsule, and a solution administration form such as an aqueous solution formulation, an ethanol solution formulation, a suspension, a lipid emulsion preparation, a liposome preparation, a clathrate such as cyclodextrin, a syrup and an elixir. These can be further classified according to the administration route into oral agents, parenteral agents (drops or injections), nasal agents, inhalants, transvaginal agents, suppositories, sublingual agents, eye drops, ear drops, ointments, creams, transdermal absorption agents, transmucosal absorption agents and the like, which can be respectively compounded, formed and prepared according to conventional methods.

When using the pharmaceutical composition of the present invention as a gene therapy agent, in general, the pharmaceutical composition is preferably prepared as an injection, a drop or a liposome preparation. When preparing the gene therapy agent in a form containing a cell into which a gene was introduced, the gene therapy agent can also be prepared, for example, in a form in which the cell is compounded in phosphate buffered saline (pH 7.4), Ringer's solution, or an injectable solution for an intracellular composition solution. The pharmaceutical composition can also be prepared in a form that allows administration thereof together with a substance that enhances the efficiency of gene transfer, such as protamine. In the case of use as a gene therapy agent, the pharmaceutical composition can be administered once per day or can be divided for administration several times per day, and may also be administered intermittently at an interval ranging from one day to several weeks. The administration method can be in accordance with a method used in a common gene therapy method.

(Diagnostic Method)

The protein, the DNA, the recombinant vector, the transformant, the antibody or the compound used in the present invention can be used by itself as disease diagnosis means, such as a diagnostic marker or a diagnostic reagent.

According to the present invention, for example, by utilizing the base sequence of all or a part of the DNA used in the present invention, it is possible to specifically detect the existence or non-existence of an abnormality in a gene that includes the DNA in an individual or in various kinds of tissue, or to detect the existence or non-existence of expression of the gene. By detecting the DNA, it is possible to perform diagnosis of susceptibility to, onset and/or prognosis of a disease attributable to the gene. The phrase "disease attributable to the gene" refers to a disease that is attributable to a quantitative abnormality and/or functional abnormality or the like of the gene. Examples of a disease attributable to the gene include neurogenic disease, such as depression.

Diagnosis of a disease by gene detection can be carried out, for example with respect to a test sample, by detecting the presence of nucleic acids corresponding to the gene, determining the existing amount thereof and/or identifying a mutation. By comparison with a normal control sample, an alteration in the existence of nucleic acids corresponding to the gene of interest and a quantitative alteration thereof can be detected. Further, by comparison with a normal genotype it is possible to detect, for example, a deletion and insertion by measuring a size alteration with respect to an amplification product that was produced by amplifying nucleic acids corresponding to the gene of interest by a known method. Furthermore, a point mutation can be identified by hybridizing amplified DNA with, for example, DNA used in the present invention that was labeled. The above described diagnosis can be carried out by detection of an alteration or a mutation in this manner.

A method for measuring qualitatively or quantitatively a gene of interest in a test sample, or a method for measuring qualitatively or quantitatively a mutation in a specific region of the gene can be performed in the present invention.

The test sample is not particularly limited as long as it includes nucleic acids of the gene of interest and/or a mutant gene thereof. For example, the test sample may be a biological sample derived from a living organism such as a cell, blood, urine, saliva, spinal fluid, biopsy tissue or autopsy material and the like. Alternatively, as desired, a nucleic acid sample may be prepared and used by extracting nucleic acids from a biological sample. The nucleic acids may be a genomic DNA which is directly used to the gene of interest or may be enzymatically amplified by use of PCR or another amplification method before analysis. RNA or cDNA may be similarly used. A nucleic acid sample may be prepared according to various methods for facilitating detection of a target sequence, for example, denaturation, digestion with restriction enzyme, electrophoresis, or dot blotting.

A known gene detection method can be used as the detection method, and examples thereof include plaque hybridization, colony hybridization, Southern blotting, Northern blotting, the Nucleic Acid Sequence-Based Amplification (NASBA) method and RT-PCR. Measurement at the cell level utilizing in situ RT-PCR or in situ hybridization or the like can also be used. Methods that can be used to detect the gene of interest are not limited to the methods described above, and any known gene detection method can be used.

For this kind of gene detection method, a fragment of the DNA used in the present invention that has a property as a probe or that has a property as a primer is useful in carrying out identification of the gene of interest or a mutant gene thereof, and/or amplification thereof. The phrase "DNA fragment having a property as a probe" refers to a substance comprising a characteristic sequence of the DNA used in the present invention that can specifically hybridize to the DNA only. The phrase "substance having a property as a primer" refers to a substance comprising a characteristic sequence of the DNA that can specifically amplify the DNA only. Further, when detecting a mutant gene capable of amplification, a probe or a primer having a sequence of a predetermined length that includes a location having a mutation within the gene is produced and used. In general, the length of the base sequence of the probe or the primer is preferably from about 5 to 50 nucleotides, more preferably from about 10 to 35 nucleotides, and further preferably from about 15 to 30 nucleotides. Although a labeled probe is normally used as the probe, the probe may be unlabeled, and may be detected directly or indirectly by specific binding with a labeled ligand. Various methods are known as methods for labeling a probe and a ligand, and examples thereof include methods utilizing nick translation, random priming or kinase treatment. As suitable labeling substances, a radioactive isotope, biotin, a fluorescent substance, a chemiluminescent substance, an enzyme, an antibody and the like may be mentioned.

PCR is preferable as the gene detection method from the viewpoint of sensitivity. The PCR method is not particularly limited as long as it is a method that uses a DNA fragment that can specifically amplify the gene of interest as a primer, for example, a conventional known method such as RT-PCR may be mentioned, and various modified methods that are used in the art can be applied.

In addition to detection of a gene, assay of the DNA of the gene of interest and/or a mutant gene thereof can be performed by PCR. As examples of this kind of analysis method, a competitive assay that is similar to a Multi-channel Simplex Stimulated Annealing (MSSA) method or PCR-SSCP which is known as a mutation detection method that utilizes variations in mobility accompanying changes in the conformation of single-strand DNA may be mentioned.

According to the present invention, it is also possible to specifically detect, for example, the existence or non-existence of an abnormality in a protein used in the present invention and a function thereof in an individual or in various kinds of tissue by utilizing the protein. By detecting an abnormality in the protein or a function thereof, it is possible to perform diagnosis of susceptibility to, onset and/or prognosis of a disease attributable to the gene.

Diagnosis of a disease by detection of a protein can be carried out, for example with respect to a test sample, by detecting the presence of the protein, determining the existing amount thereof, and/or detecting a mutation. More specifically, the protein and/or a mutant thereof are quantitatively or qualitatively determined. By comparison with a normal control sample, an alteration in the existence of the protein of interest and a quantitative alteration thereof can be detected. In a comparison with a normal protein, for example, a mutation thereof can be detected by determining the amino acid sequence. The above described diagnosis can be carried out by detecting this kind of alteration or mutation. The test sample is not particularly limited as long as it includes the protein of interest and/or a mutant thereof. For example, the test sample may be a biological sample derived from a living organism such as blood, serum, urine, biopsy tissue or the like.

Determination of the protein used in the present invention as well as the protein having a mutation can be carried out by use of the protein, for example, the protein comprising the amino acid sequence represented by SEQ ID NO: 2 of the sequence listing, or an amino acid sequence having a deletion, substitution, insertion or addition of from one or several to multiple amino acids in the amino acid sequence of the protein, fragments of these, or an antibody against the protein or a fragment thereof.

Quantitative or qualitative determination of the protein can be performed using a protein detection method or assay method according to a common technique in the field of the art. For example, a mutant protein can be detected by analyzing the amino acid sequence of the protein of interest, and more preferably, a variation in the sequence of the protein of interest or the existence or non-existence of the protein of interest can be detected using an antibody (a polyclonal or monoclonal antibody).

According to the present invention, a qualitative or quantitative method for measurement of the protein of interest in a test sample, or a qualitative or quantitative method for measurement of a mutation in a specific region of the protein can be conducted.

More specifically, the above detection can be carried out for a test sample by performing immunoprecipitation using a specific antibody against the protein of interest, and conducting analysis of the protein of interest by Western blotting or immunoblotting. Further, the protein of interest can be detected in a paraffin or frozen tissue section by an antibody against the protein of interest using an immunohistochemical technique.

As preferred specific examples of a method that detects the protein of interest or a mutant thereof, immuno-enzyme assay (IEMA), immunoradiometric assay (IRMA), radioimmunoassay (RIA) and enzyme-linked immunosorbent assay (ELISA) including a sandwich method using a monoclonal antibody and/or polyclonal antibody may be mentioned. In addition, a radioimmunoassay or a competitive binding assay and the like can also be utilized.

(Reagents and Reagent Kit)

The protein, DNA, recombinant vector, transformant and antibody used in the present invention can each be used by itself as a reagent or the like. For example, each of these can be used as a reagent for use in the method of identifying a compound according to the present invention or the method for determining a protein and/or DNA according to the invention. The reagent is useful, for example, in elucidating a cellular signal transduction pathway in which the protein or DNA participates, as well as for fundamental research relating to diseases and the like attributable to an abnormality in the protein and/or DNA.

Specifically, as the reagent kit according to the present invention, a reagent kit may be exemplified which comprises at least one selected from the following: a DNA represented by any one of base sequences described in SEQ ID NO: 1, 15 and 17 of the sequence listing; a recombinant vector containing the DNA; a transformant in which the recombinant vector is introduced; a protein encoded by the DNA; and an antibody that recognizes the protein. More specifically, a reagent kit may be exemplified which comprises at least one selected from the following: a DNA represented by any one of base sequences described in SEQ ID NO: 1, 15 and 17 of the sequence listing; a recombinant vector containing the DNA; a transformant in which the recombinant vector is introduced; a protein represented by any one of amino acid sequences described in SEQ ID NO: 2, 16 and 18; and an antibody that recognizes the protein When these are reagents, they may include a substance such as a buffer solution, a salt, a stabilizer and/or an antiseptic agent. In this connection, known formulation means may be introduced in accordance with the respective properties at the time of formulation.

The present invention further provides a reagent kit including at least one member of the group consisting of the protein, DNA, recombinant vector, transformant and antibody used in the present invention. When these are comprised in a reagent kit, the kit may include a substance necessary to carry out a measurement, such as a labeling substance for detecting the protein or DNA, detection agent for the labeling substance, a reaction diluent, a standard antibody, a buffer solution, a washing agent and a reaction terminating solution. Examples of a labeling substance include the above described labeling proteins and chemically-modified substances, and the labeling substance may be previously attached to the protein or DNA.

The reagent kit according to the present invention can be used the above described identification methods and measurement methods. The present invention can also be used as a testing agent as well as a testing kit in a testing method that uses the above described measurement methods. It can also be used as a diagnostic agent as well as a kit for diagnosis in a diagnostic method that uses the above described measurement methods.

Although the present invention is described specifically by the following examples, the present invention is not limited to the following Examples.

EXAMPLE 1

(Construction of Human Brain-Derived cDNA Library and Isolation of Gene)

A cDNA library was constructed according to an ordinary method employing commercially available polyA$^+$ RNA derived from the human brain, fetal brain and brain hippocampus (Clontech Inc.: catalog Nos. 6516-1, 6525-1, and 6578-1) as starting material, and the base sequences of cDNA clones were determined after isolating cDNA fragments by dbEST analysis. More specifically, in accordance with the method of Ohara et al. (Ohara, O. et al., "DNA Research", 1997, Vol. 4, p. 53-59), approximately 50,000 recombinants were randomly selected from the cDNA library derived from human brain that was prepared as described above, and the base sequences at the 5'-terminus and 3'-terminus were determined for cDNA of approximately 30,000 clones among these. Further, approximately 1,100 clones were selected by mainly in-vitro transcription translation experiment, and the base sequences of the cDNA of these were determined according to the method of Ohara et al. For cDNA clones whose entire base sequence was determined, the ORF was predicted by a generic analysis method using a computer program to obtain a cDNA clone having a seven-span transmembrane domain in this region.

The identified cDNA clone ph01207 is a DNA (SEQ ID NO: 1) having a novel base sequence of a total length of 4557 bps including an ORF comprising 1518 amino acid residues having a segment (20 amino acid residues from the N terminus) that is predicted to be a signal sequence. Based on a homology search, it is considered that ph01207 is a splice variant having a deleted region encoding 55 amino acid residues at the N-terminal region in the sequence of hBAI2 (GenBank accession number AB005298), and also having added one amino acid residue in a region on the C-terminal side (lysine at position 1406 in the amino acid sequence represented by SEQ ID NO: 2) (FIG. 1-A).

As the structural characteristics of the protein encoded by ph01207, it was found that in addition to three TSP-I domains, the protein has a GPS domain and a GPCR family-2 domain (seven-span transmembrane domain).

Meanwhile, it is considered that the protein encoded by hBAI2 has a GPS domain and a GPCR family-2 domain, in addition to four TSP-I domains. It was thus clarified that 55 amino acid residues corresponding to a region including one TSP-I domain on the N-terminal region side of hBAI2 are deleted in the protein encoded by ph01207.

In tissue analysis for ph01207 gene expression, specifically high expression of the gene was observed universally in normal brain tissues (for example, brain cortex (temporal pole, motor cortex), hippocampus, amygdaloid body and the like). Further, enhancement of expression was observed in ovarian cancer, liver cancer, and adrenal cancer in comparison to the respective normal tissue.

EXAMPLE 2

(Production of ph01207 Expression Cell Line and Expression of DNA in the Cell Line)

Using the clone ph01207 that was identified in Example 1, the protein encoded by ph01207 was expressed as an N-terminal epitope-tag fusion protein.

First, an expression vector containing the ph01207 gene was constructed. Using the clone ph01207 identified in Example 1, DNA encoding the amino acid sequence excluding a segment predicted to be a signal sequence (20 amino acid residues from N terminus) was cloned into pDONR201 by PCR and restriction enzyme treatment to construct a ph01207 entry vector. PCR was carried out using oligonucleotides comprising the base sequences represented by SEQ ID NOs: 4 to 11 in the sequence listing, respectively, as primers, and using Pfu turbo DNA polymerase (Stratagene) as polymerase.

Two kinds of vector, p3xFLAG-CMV9-attR and T8HA-attR/pCINeo, were prepared as N-terminal epitope-tag fusion type expression vectors. p3xFLAG-CMV9-attR is a vector obtained by making p3xFLAG-CMV9 (Sigma Inc.) compatible to the Gateway system using the Gateway Vector Conversion System (Invitrogen Corp.). T8HA-attR/pCINeo was constructed using pCINeo (Promega Corp.), synthetic oligos (T8SP-HA (SEQ ID NO: 12) and T8SP-HA as (SEQ ID NO: 13)) and the Gateway Vector Conversion System in accordance with information in the literature (Koller, K. J., et al., "Analytical Biochemistry", 1997, Vol. 250, p. 51-60). Both vectors have a secretory signal sequence (FLAG: PPTLS, HA: T8) before (N-terminal side) epitope-tag. Using these vectors, an N-terminal FLAG-tag or HA-tag fusion type expression vector was constructed by LR reaction with Mammalian Expression system with Gateway technology (Invitrogen Corp.). For each of the constructed expression vectors it was confirmed by restriction enzyme treatment and sequence analysis that no base substitution or deletion existed in a coding region in the introduced sequence.

After transfecting each of the thus constructed two kinds of expression vector to the CHO-K1 cell line using FuGENE 6 (Roche), selection of the expression cell line was performed by cultivation with a culture medium including G418 (DMEM/F12 medium containing 400 μg/mL G418 and 10% fetal calf serum). For expression cell lines that grew, selection was further performed by cell enzyme immunoassay (cell EIA) using peroxidase (POD)-labeled antibody (anti-FLAG M2-POD antibody and anti-HA-POD antibody: 3F10) against epitope-tag. For the selected cell lines, selection was further carried out by fluorocytometry (FCM) analysis using primary antibody (anti-FLAG M2 antibody and anti-HA antibody: clone HA-7) and fluorescein isothiocyanate (FITC)- labeled secondary antibody (FITC-anti-mouse IgG antibody), to obtain expression cell lines.

As the result of the FCM analysis, 8 clone lines expressing a protein (FLAG-tag fusion protein) recognized by anti-FLAG antibody on the cell membrane and 4 clone lines expressing a protein (HA-tag fusion protein) recognized by anti-HA antibody were obtained. Since a fluorescent signal produced by bonding of an antibody recognizing FLAG-tag or HA-tag was clearly stronger for each of these clones in comparison to the host cell line (CHO-K1), it was clarified that the gene of interest was expressed therein. Representative results are shown in FIG. 2.

It was clarified based on the FCM analysis result that the ph01207 gene product of the N-terminal epitope-tag fusion type expresses on the cell membrane.

Among the clones for which expression of HA-tag fusion protein was observed, a cell line denominated as HA-ph01207#10-6 was deposited with the International Patent Organism Depositary of the National Institute of Advanced Industrial Science and Technology (Japan) on Aug. 19, 2004 under Accession NO: FERM BP-10101. The existence of this cell line was confirmed by experiment at the International Patent Organism Depositary on Sep. 22, 2004. The HA-ph01207#10-6 cell line is a cell line that was established by transfecting into CHO-K1 cell line a vector that expresses, as an N-terminal HA-tag fusion protein, DNA consisting of a base sequence lacking a segment predicted to encode a signal sequence (20 amino acid residues from the N terminus of the amino acid sequence represented by SEQ ID NO: 2) among the open reading frame (ORF) of the DNA consisting of the base sequence represented by SEQ ID NO: 1, and it stably expresses the N-terminal HA-tag fusion protein.

EXAMPLE 3

(Functional Analysis of ph01207 Gene Product)

Functional analysis of the ph01207 gene product was carried out by determining the cell response when a ligand was added to *Xenopus laevis* oocyte that expressed ph01207. Determination of the cell response was carried out using six individuals each of control oocyte (oocyte into which the gene was not introduced) and oocyte that expressed the gene (ph01207 cDNA clone), by measuring variations in the membrane potential of the oocyte when a ligand was added thereto. Culture supernatant of the HeLa cell line in which expression of ph01207 was observed was used as the ligand. The culture supernatant was prepared by culturing HeLa cells of a cell count of $1.2 \times 10^6$ in DMEM containing 10% fetal calf serum for two days, after which the culture supernatant was recovered and filtered with a filter (0.45 µM). Two kinds of culture supernatant with different lots prepared in the same manner were used as the ligand (hereunder, referred to as ligand sample 1 and 2).

The Ligand sample 1 or 2 was added to the oocyte that expressed the ph01207 gene and the control oocyte to determine membrane potential variations. Evaluation was carried out using variations in current amount and waveforms showing variations in current amount. When a variation in the current amount was 0.2 µA or more and a waveform of a GPCR-specific pattern was observed, it was judged that a response to ligand stimulation was generated. The phrase "GPCR-specific pattern" refers to the pattern of waveform 1 shown in FIG. 3. The patterns of waveform 2-4 shown in FIG. 3 are waveform patterns produced by artificial elements such as the influence of some kind of component such as a solvent, or a high concentration ligand, and thereby it was judged that a response generated was not against ligand stimulation. Further, when the patterns shown in waveform 5 and 6 were observed, it was judged that a response to ligand stimulation was not generated.

As a result, variations in the current amount were observed in only the ph01207 expression cells (Table 1 and Table 2). The characters "ND" in Table 2 indicate that the current variation amount was less than 0.2 µA and a response was not observed. As shown in Table 1, a response to ligand stimulation was observed in all six samples of the ph01207 expression cell lines. In contrast, there was completely no response to the ligand in the control cells (Table 2). The inventors therefore considered that the response of the ph01207 expression cells produced by ligand stimulation is a specific response to the expressed receptor. A similar result was obtained when using either of the ligand samples 1 and 2.

TABLE 1

| | | | | ph01207 Expressing Oocyte | | | | | | |
|---|---|---|---|---|---|---|---|---|---|---|
| Ligand sample | Rate of response | Representative Waveform | Mean amount of current variation ± S.D. | Amount of current variation (µA) | | | | | | |
| | | | | 1 | 2 | 3 | 4 | 5 | 6 | |
| 1 | 6/6 | GPCR | 1.21 ± 0.54 | 1.33 | 1.81 | 1.30 | 0.50 | 0.63 | 1.70 | |
| 2 | 6/6 | GPCR | 0.48 ± 0.24 | 0.66 | 0.24 | 0.29 | 0.58 | 0.82 | 0.27 | |

TABLE 2

| | | | | Control Oocyte | | | | | | |
|---|---|---|---|---|---|---|---|---|---|---|
| Ligand sample | Rate of response | Representative Waveform | Mean amount of current variation ± S.D. | Amount of current variation (µA) | | | | | | |
| | | | | 1 | 2 | 3 | 4 | 5 | 6 | |
| 1 | 0/6 | ND | | ND | ND | ND | ND | ND | ND | |
| 2 | 0/6 | ND | | ND | ND | ND | ND | ND | ND | |

As described above, because a cell response to ligand stimulation was produced by expression of the ph01207 gene, the inventors considered that the ph01207 gene product is a GPCR having a function that activates the intracellular signal transduction pathway in response to a ligand.

EXAMPLE 4

(Analysis of Protein Interaction of ph01207 Gene Product)

Analysis of protein interaction of the ph01207 gene product was examined using the yeast two hybrid system.

Based on ph01207 sequence information and hBAI2 sequence information, bait was set respectively in the N-terminal region (4 places) and the C-terminal region (2 places) of the ph01207 gene product, and the N-terminal region (region lacking 55 amino acid residues in ph01207) and the C-terminal region (region having an insertion of one amino acid residue in ph01207) of the hBAI2 gene product, and screening was performed for a cDNA library (derived from brain, hippocampus, breast cancer and prostate cancer, heart and skeletal muscle) that was selected according to a report (Non-Patent Literature 1) regarding the distribution of hBAI2 expression.

When using either the bait designed in the C-terminal region of the ph01207 gene product (having an insertion of one amino acid residue corresponding to position 1461 in the amino acid sequence represented by SEQ ID NO: 2) or the C-terminal region of the hBAI2 gene product (without insertion of the amino acid residue), the MAGUK family proteins DLG2, DLG3, DLG4, AIP1, MAGI3 and the like were obtained as prey. In addition, HOMER2, Citron, SYNE-1, KIF5A and KIFAP3 were obtained as prey that is specific to the hBAI2 gene product.

Although only BAT1 (HLA-B associated transcript 3) was obtained as prey for the bait designed in the N-terminal region having deleted 55 amino acid residues) of the ph01207 gene product, KCNN2 (potassium intermediate/small conductance calcium-activated channel, subfamily N, member 2) and the like were obtained for the bait designed in the N-terminal region (without deletion of the amino acid residues) of the hBAI2 gene product.

It was thus found that, with the exception of MAGUK family proteins, there is a difference in the interacting proteins detected by the yeast two hybrid system for the ph01207 gene product and the hBAI2 gene product.

The ph01207 gene product and the hBAI2 gene product interact with MAGUK family proteins in their respective C-terminal regions. MAGUK family proteins are present in cytoplasm and bind with membrane proteins such as receptors or ion channels that are present in the cell membrane to participate in signal transduction from these membrane proteins. The inventors therefore considered that the ph01207 gene product and the hBAI2 gene product are functional membrane protein receptors that participate in intracellular signal transduction through MAGUK family proteins.

EXAMPLE 5

(Determination of Change in Intracellular Calcium Concentration in ph01207 Expression Cell Line Caused by CCK 8)

Changes in intracellular calcium ($Ca^{2+}$) concentrations caused by CCK-8S (SEQ ID NO: 14), CCK-8NS and CCK-4 were determined using the ph01207 expression cell lines prepared in Example 2. The cell lines prepared in Example 2 are eight lines in which the protein encoded by ph01207 expresses as a FLAG-tag fusion protein and four lines in which the protein encoded by ph01207 expresses as a HA-tag fusion protein. Among these, in this example HA-ph01207#10-6 cell line was used as a line obtained by cellular cloning of one cell line that stably expresses the protein encoded by ph01207 as a HA-tag fusion protein. Although CCK-8NS is a CCK octapeptide consisting of the same amino acid sequence as CCK-8S (SEQ ID NO: 14), the seventh tyrosine residue from the C-terminal thereof is not sulfated. CCK-4 is a tetrapeptide consisting of the amino acid residues from the C-terminus to the fourth amino acid residue of CCK-8S (SEQ ID NO: 14).

A specific method for measuring a change in intracellular $Ca^{2+}$ concentration in the HA-ph01207#10-6 cell line produced by CCK-8S (SEQ ID NO: 14) and the results thereof are described below. HA-ph01207#10-6 cell line was seeded in 96-well plates (plates with a black wall surface and transparent bottom) at a cell count of $2 \times 10^4/100$ μL medium/well and cultured at 37° C. in the presence of 5% $CO_2$. DMEM/F12 (Gibco) containing 10% fetal calf serum (Moregate Bio-Tech) was used as medium. The next day, 50 μL of medium was extracted from each well, and 50 μL of loading buffer was added each well and allowed to react at room temperature for 1.5 h so as to incorporate fluorescent dye contained in the loading buffer into cells. The loading buffer was prepared by dissolving component A of the FLIPR Calcium 3 Assay Kit (Molecular Devices Corp.) with a solution in which 0.1 mL of 500 mM probenecid (Sigma) was added to 9.9 mL of component B. After the reaction, a change in the fluorescence intensity upon addition of CCK-8S (Peptide Institute, Osaka, Japan) was measured along with time for each well using FLEXstation (Molecular Devices Corp.). Measurement was also performed in a similar manner for CCK-8NS (Peptide Institute, Osaka, Japan) and CCK-4 (Peptide Institute). For CCK-8S (SEQ ID NO: 14), 0.52 mg thereof was dissolved with 4.5 mL of 1% $NaHCO_3$ (Wako) to prepare a 0.1 mM concentration solution. For CCK-8NS, after dissolving 0.53 mg thereof with 0.50 mL of dimethylsulfoxide (DMSO, Sigma), 4.50 mL of redistilled water was added thereto to prepare a 0.1 mM concentration solution. For CCK4, after dissolving 0.54 mg thereof with 0.46 mL of DMSO, 4.09 mL of redistilled water was added thereto to prepare a 0.2 mM concentration solution. CCK-8S (SEQ ID NO: 14), CCK-8NS and CCK4 were each diluted with phosphate buffered saline (PBS) to make a 5 nM solution, and measurement was performed after adding 25 μL (final concentration 1 nM) of each. As a positive control that induces an increase in intracellular $Ca^{2+}$ concentration, A23187 (Calbiochem, CA) was used at a final concentration of 10 μM. As a negative control, CHO-K1 cell line that was used as a host in production of the HA-ph01207#10-6 cell line was used. Since the ph01207 expression vector was not transfected into the CHO-K1 cell line, the ph01207 gene product was not expressed therein.

The results showed that the intracellular $Ca^{2+}$ concentration of the HA-ph01207#10-6 cell line that was stimulated by CCK-8S (SEQ ID NO: 14) (FIG. 4-A) rose in comparison to the HA-ph01207#10-6 cell line that was not stimulated (FIG. 4-E). However, a rise in the intracellular $Ca^{2+}$ concentration of the HA-ph01207#10-6 cell line was not observed in the cells stimulated by CCK-8NS or CCK4 (FIG. 4-B and FIG. 4-C). Further, a rise in the intracellular $Ca^{2+}$ concentration of the HA-ph01207#10-6 cell line stimulated by A23187 was observed (FIG. 4-D).

The level of increase in the intracellular $Ca^{2+}$ concentration of the HA-ph01207#10-6 cell line stimulated by 1 nM CCK-8S (SEQ ID NO: 14) (FIG. 4-A) was roughly equal to level of increase in the intracellular $Ca^{2+}$ concentration produced by A23187 that was used as a positive control (FIG. 4-D).

In contrast, the CHO-K1 cell line showed no increase in intracellular $Ca^{2+}$ concentration when stimulated with either CCK-8S (SEQ ID NO: 14), CCK-8NS or CCK-4 (FIG. 4-A, FIG. 4-B and FIG. 4-C). However, an increase in the intracellular $Ca^{2+}$ concentration of CHO-K1 cells upon stimulation with A23187 was observed (FIG. 4-D).

From these results it was clarified that the HA-ph01207#10-6 cell line responds specifically to CCK-8S (SEQ ID NO: 14). It was also clarified that the protein encoded by ph01207 that was expressed in the HA-ph01207#10-6 cell line is involved in the increase in the intracellular $Ca^{2+}$ concentration in the cell line caused by CCK-8S (SEQ ID NO: 14). The inventors therefore considered that CCK-8S (SEQ ID NO: 14) is a ligand of the ph01207 gene product.

The HA-ph01207#10-6 cell line also exhibited a sufficiently high biological response to 1 nM CCK-8S (SEQ ID NO: 14). Since CCK-8S (SEQ ID NO: 14) of a low concentration of 1 nM induced a biological response in the HA-ph01207#10-6 cell line, the inventors considered that CCK-8 actually induces a cellular biological response through the protein encoded by ph01207 in vivo. That it, the inventors considered that CCK-8S (SEQ ID NO: 14) is one of the in vivo ligands of ph01207 that is predicted to be a GPCR.

EXAMPLE 6

(Identification of Splicing Variant of ph01207 Gene)

A splicing variant of ph01207 gene was acquired by carrying out cloning by RT-PCR.

Acquisition of the splicing variant of ph01207 gene was carried out as follows. First, cDNA library was constructed by an ordinary method using human brain-derived polyA+ RNA (Clontech) as the starting material followed by isolating cDNA fragment by dbEST analysis, and then the base sequence of cDNA clone was determined. Specifically, RT-PCR was carried out using Superscript first-strand synthesis system for RT-PCR (Invitrogen) in 10 μL reaction system containing 0.1 μg of polyA+ RNA to construct a cDNA library. Using this cDNA as a genetic template, PCR was carried out using an oligonucleotide consisting of the base sequence described in SEQ ID NO: 23 and an oligonucleotide consisting of the base sequence described in SEQ ID NO: 24 as a primer. PCR using these primers amplifies a DNA of a region encoding an amino acid sequence from aspartic acid (D) at position 44 to cysteine (C) at position 475 of hBAI2 (SEQ ID NO: 22), and a DNA corresponding to the region in a splicing variant of hBAI2 (SEQ ID NO: 22) (see FIG. 1-C). A recombination by ScaI and XhoI was carried out between each clone obtained and ph01207 cDNA clone, and thereby three kinds of full length cDNA clones were obtained. Confirmation of the base sequence of each of the clones was carried out by sequence analysis.

As a result, three kinds of full length cDNA clones that are considered to be splicing variants of ph01207 gene from viewpoints of sequence homology and structural similarity were obtained. These cDNA clones are referred to as 7tmHR gene, hk01941 gene and variant 3 gene, respectively. All of these splicing variants are variants having different numbers of repeats of TSP-I domain in the N-terminal extracellular region (FIG. 1-B). 7tmHR gene among these splicing variants encodes the longest protein.

7tmHR gene comprises a base sequence (SEQ ID NO: 19) of 4719 bps containing an ORF encoding 1573 amino acid residues (SEQ ID NO: 20) having a portion predicted to be a signal sequence (20 amino acid residues from N-terminus). The 7tmHR gene has been registered in GenBank as Accession No: AB065648. The protein encoded by this DNA has a seven-span transmembrane domain, and has four TSP-I domains and one GPS domain. (See FIG. 1-B). The protein has the same amino acid sequence as hBAI2 except for the insertion of one amino acid residue in the C-terminal side region in comparison to the sequence of hBAI2 (GenBank, Accession NO: AB005298). The insertion of one amino acid residue was found between glutamic acid (E) at position 1460 and valine (V) at position 1461 in the amino acid sequence of hBAI2, and the amino acid residue being inserted was lysine. The inserted lysine corresponds to position 1461 in the amino acid sequence of the protein (SEQ ID NO: 20) that was encoded by 7tmHR gene. From viewpoints of sequence homology and structural similarity, the inventors considered that 7tmHR gene as well as the protein encoded by the gene was a splicing valiant of hBAI2 gene.

hk01941 gene is a novel gene comprises a base sequence (SEQ ID NO: 15) of 4389 bps containing an ORF encoding 1463 amino acid residues (SEQ ID NO: 16) having a portion predicted to be a signal sequence (20 amino acid residues from N-terminus). The protein encoded by this DNA has a seven-span transmembrane domain, and has two TSP-I domains and one GPS domain. (See FIG. 1-B). The amino acid sequence of the protein encoded by this DNA is same as that of the protein (SEQ ID NO: 20) encoded by 7tmHR gene except for the deletion of 110 amino acid residues including two TSP-I domains at N-terminal side. The deleted 110 amino acid residues corresponds to those from glycine (G) at position 296 to proline (P) at position 405 in the amino acid sequence (SEQ ID NO: 20) of the protein encoded by 7tmHR gene.

Variant 3 gene is a novel gene comprises a base sequence (SEQ ID NO: 17) of 4554 bps containing an ORF encoding 1518 amino acid residues (SEQ ID NO: 18) having a portion predicted to be a signal sequence (20 amino acid residues from N-terminus). The protein encoded by this DNA has a seven-span transmembrane domain, and has three TSP-I domains and one GPS domain. (See FIG. 1-B). The amino acid sequence of the protein encoded by the DNA is same as that of the protein (SEQ ID NO: 20) encoded by 7tmHR gene except for the deletion of 55 amino acid residues including one TSP-I domain from N-terminal side. The deleted 55 amino acid residues corresponds to those from valine (V) at position 351 to proline (P) at position 405 in the amino acid sequence (SEQ ID NO: 20) of the protein encoded by 7tmHR gene.

The amino acid sequence of the protein encoded by ph01207 gene was same as that of the protein (SEQ ID NO: 20) encoded by 7tmHR gene except for the deletion of 55 amino acid residues including one TSP-I domain at second from N-terminal side. The deleted 55 amino acid residues corresponds to those from glycine (G) at position 296 to proline (P) at position 350 in the amino acid sequence (SEQ ID NO: 20) of the protein encoded by 7tmHR gene.

EXAMPLE 7

(Construction of Stably Expressing Cell Line of Splicing Variant of ph01207 Gene)

A stably expressing cell line of a splicing variant of ph01207 gene was constructed to use in the investigation whether or not cell response by CCK-8S was caused in the stably expressing cell line. As the splicing variant, three kinds of splicing variants acquired in EXAMPLE 6 that were 7tmHR gene, hk01941 gene and variant 3 gene were used.

First, an expression vector of each of full length cDNA clones was constructed by using pcDNA3.1 (+) (Invitrogen) that was an expression vector for animal cells to carry out recombinant reaction with each of full length cDNA clone by Asp718I and NotI. Expression vectors thus obtained were referred to as 7tmHR/pcDNA3.1, hk01941/pcDNA3.1 and variant 3/pcDNA3.1.

7tmHR stably expressing cell line and hk01941 stably expressing cell line were prepared by transfecting CHO-K1 cell line with each of 7tmHR expression vector (7tmHR/pcDNA3.1) and hk01941 expression vector (hk01941/pcDNA3.1). Specifically, transfection was carried out in such that the expression vector was mixed with Lipofectamine 2000 (may be abbreviated to as LF2000, Invitrogen) (4 μg, DNA/250 μL DMEM/F12 medium+10 μL LF 2000/250 μL DMEM/F12 medium), and added to CHO-K1 cell line (2 mL medium/well) cultured in 6-well plates. The next day cells were collected and seeded to 96-well plates at a cell density of one cell/well to carry out culture in medium (DMEM/F12 medium containing 10% FCS) containing G418 (400 μg/mL) for selection to screen expression cell lines. Further, the screened expression cell lines were subjected to FCM analysis using anti-hBAI2 antibody and Western blotting to confirm expression of each of introduced genes.

EXAMPLE 8

(Functional Analysis of Stably Expressing Cell Line of Splicing Variant of ph01207 Gene)

Using stably expressing cell line of a splicing variant of ph01207 gene, a change in intracellular calcium concentration ($Ca^{2+}$) caused by CCK-8S was measured using the same method described in Example 5. As the stably expressing cell line of the splicing variant of ph01207 gene, the stably expressing cell line constructed in Example 7 was used. Further, using stable expressing cell line of hk01941 gene, the same investigation was conducted. As the stably expressing cell line of hk01941 gene, the stably expressing cell line constructed in Example 7 was used. As a control, a host cell which was not transfected with 7 μm expression vector or hk01941 expression vector was used.

The cell line was seeded in 96-well plates (plates with a black wall surface and transparent bottom) at $3 \times 10^4$ cells/100 μL medium/well and cultured overnight at 37° C. in the presence of 5% $CO_2$. The next day, 50 μL of the medium was extracted from each well, and 50 μL of loading buffer was added to each well to allow for a reaction at room temperature for 1 h so as to incorporate fluorescent dye contained in the loading buffer into cells. The loading buffer was prepared by the same method as described in Example 5. After the reaction, a change in the fluorescence intensity upon addition of CCK-8S was measured along with time for each well using FLEXstation (Molecular Devices Corp.). CCK-8S was used at a final concentration of 10 pM-1 μM. Further, A23187 was used at a final concentration of 20 μM as a positive control of the assay.

An increase in intracellular calcium ($Ca^{2+}$) was observed upon addition of CCK-8S in both 7tmHR stably expressing cell line and hk01941 stably expressing cell line. In contrast, a change in intracellular calcium concentration was not observed upon addition of CCK-8S in a host cell which was transfected with neither 7tmHR expression vector nor hk01941 expression vector. The similar results could be obtained in a plurality of clones of both stably expressing cell lines. Changes in intracellular calcium ($Ca^{2+}$) concentration upon addition of CCK-8S (physiological concentration 1 nM) are shown in FIG. 5-A and FIG. 6-A for typical clones of 7tmHR stably expressing cell line and hk01941 stably expressing cell line. Further, a response to A23187 (20 μM) used as a positive control was observed similarly in both expression cell line and host cell (FIG. 5-B and FIG. 6-B).

Since a change in intracellular calcium ($Ca^{2+}$) concentration that was not given in the host cell was observed in 7tmHR stably expressing cell line and hk01941 stably expressing cell line upon addition of CCK-8S, the inventors considered that gene products of both 7tmHR gene and hk01941 gene mediated a cell response caused by CCK-8S. That is, gene products of both 7tmHR gene and hk01941 gene were expressed on the surface of cell membrane and activated intracellular signal transduction pathway by an action of extracellular CCK-8S, thereby causing increase in intracellular calcium ($Ca^{2+}$) concentration as a cell response.

EXAMPLE 9

(Functional Analysis of Stably Expressing Cell Line of Variant 3 Gene)

The function of variant 3 gene was analyzed using stably expressing cell line of variant 3 gene by investigating a change in intracellular calcium concentration ($Ca^{2+}$) caused by CCK-8S. The change in intracellular calcium concentration ($Ca^{2+}$) was measured using the same method described in Example 5. The stably expressing cell line of variant 3 gene was prepared using the variant 3 gene expression vector constructed in Example 7 by the method similar to the method described in Example 7.

The cell line was seeded in 96-well plates (plates with a black wall surface and transparent bottom) at $3 \times 10^4$ cells/100 μL medium/well and cultured overnight at 37° C. in the presence of 5% $CO_2$. The next day, 50 μL of the medium was extracted from each well, and 50 μL of loading buffer was added to each well to allow for a reaction at room temperature for 1 h so as to incorporate fluorescent dye contained in the loading buffer into cells. The loading buffer was prepared by the same method as described in Example 5. After the reaction, a change in the fluorescence intensity upon addition of CCK-8S was measured along with time for each well for 40 sec using FLEXstation (Molecular Devices Corp.). CCK-8S was used at a final concentration of 10 pM-1 μM. Further, A23187 was used at a final concentration of 20 μM as a positive control of the assay.

An increase in intracellular calcium ($Ca^{2+}$) was observed upon addition of CCK-8S in the variant 3 stably expressing cell line. In contrast, a change in intracellular calcium concentration was not observed upon addition of CCK-8S in a host cell which was not transfected with variant 3 expression vector. Changes in intracellular calcium ($Ca^{2+}$) concentration upon addition of CCK-8S (physiological concentration 1 nM) are shown in FIG. 7-A for a typical clone of variant 3 stably expressing cell line. Further, a response to A23187 (20 μM) used as a positive control was observed similarly in both expression cell line and host cell (FIG. 7-B).

Since a change in intracellular calcium ($Ca^{2+}$) concentration that was not given in the host cell was observed in variant 3 gene stably expressing cell line upon addition of CCK-8S, the inventors considered that the gene product of variant 3 gene mediated a cell response caused by CCK-8S. That is, the gene product of variant 3 gene was expressed on the surface of cell membrane and activated intracellular signal transduction pathway by an action of extracellular CCK-8S, thereby causing increase in intracellular calcium ($Ca^{2+}$) concentration.

EXAMPLE 10

(Tissue Expression of ph01207 Gene)

Tissue expression of ph01207 gene was analyzed by search in LifeSpan DrugTarget Database™ (LifeSpan Bioscience) and search in BioExpress Database (Gene Logic).

The analysis by searching in LifeSpan DrugTarget Database™ (LifeSpan Bioscience) revealed that in the tissue immunostaining data obtained with three kinds of rabbit anti-human BAI2 polyclonal antibodies (LS-A981, A982, A984; Life Span), neuron and astrocyte in amygdaloid body, hippocampus, medulla, hypothalamus, locus niger, and brain cortex, a part of cells in anterior pituitary, and Herring body of posterior pituitary were commonly strongly stained. FIG. 8-A and FIG. 8-B show tissue immunostaining data by LS-A981 of protoplasmic astrocyte of amygdaloid body, and of neuron and glia of amygdaloid body, respectively. FIG. 8-C and FIG. 8-D show tissue immunostaining data by LS-A981 of neuron in CA2 region and in CA1 region of hippocampus, respectively.

Expression analysis using Genetip analysis data of BioExpress Database (Gene Logi) was carried out for ph01207 (hBAI2), CCK-A receptor (CCK-AR), CCK-B receptor (CCK-BR) and CCK. Results of the analysis are shown in Table 3.

It was observed that ph01207 (hBAI2) gene strongly expresses in brain tissue, particularly in brain cortex (temporal pole of cerebrum, motor cortex or the like), hippocampus and amygdaloid body (Table 3). This gene was observed little in digestive organs such as pancreas, small intestine, stomach, and gall bladder.

In contrast, the expression of CCK-A receptor (referred to as CCK-AR in the table) was observed little in the brain tissue and observed in digestive organs such as pancreas, stomach, gall bladder (Table 3). Further, the expression of CCK-B receptor (referred to as CCK-BR in the table) was remarkable in pancreas and small intestine, and was also observed in brain tissue such as brain cortex, hippocampus and amygdaloid body (Table 3). The amount of expression of ph01207 (hBAI2) gene in brain tissue was much higher compared with the amount of expression of CCK-B receptor.

Analysis of tissue expression of CCK revealed a similar distribution as that observed with ph01207. Thus, it was demonstrated that ph01207 and CCK expressed strongly at the same site (Table 3).

upstream from intron located upstream of a 876D-917L region of mouse BAI2 gene in 5' side (5' arm) and genome sequence 1.2 kb downstream from intron located downstream from a 876D-917L region of the gene in 3' side (3' arm). LacZ-Neo fragment was inserted to target site of mouse BAI2 gene by homologous recombination using this targeting vector. ES cell in which homologous recombination took place was selected using selection medium containing G418, and chimeric mouse was prepared by an ordinary method using C57BL/6 mouse. By mating thus obtained chimeric mouse with C57BL/6 mouse, first filial generation (F1) heterozygous mutant mouse was generated. Further, by mating F1 heterozygous mutant mice with each other, second filial generation (F2) homozygous mutant mouse was generated.

Genotype determination for F1 heterozygous mutant mouse and F2 homozygous mutant mouse was carried out by PCR and northern analysis.

Determination whether or not LacZ-Neo fragment was inserted in target site of mouse BAI2 gene was carried out for F1 heterozygous mutant mouse by LacZ expression analysis. As a result, in F1 heterozygous mutant mouse, strong expression of LacZ was observed in tissue, particularly in hippocampus and amygdaloid body (FIG. 9-A and FIG. 9-B). From these results, it was confirmed that in F1 heterozygous mutant mouse, LacZ-Neo fragment was inserted at target site of mouse BAI2 gene, that is, the gene was destroyed. These results also suggested that in F1 heterozygous mutant mouse, mouse BAI2 gene was strongly expressed in brain tissue, particularly in hippocampus and amygdaloid body.

The functions of BAI2 knockout mouse were investigated in behavioral examination, physiological examination, pathological examination and anatomical examination.

The BAI2 knockout mouse showed a significant difference in results of the tail suspension test in the behavioral examination in comparison to a wild type mouse (FIG. 10). In contrast, the BAI2 knockout mouse did not show a significant difference in many examination items such as physiological examination, pathological examination and anatomical examination in comparison to a wild type mouse.

TABLE 3

|  |  | CCK-AR | CCK-BR | ph01207 | CCK |
|---|---|---|---|---|---|
| Brain | Brain cortex | 50> | 100~200 | 300~700 | 500~1500 |
|  | Hippocampus | 50> | 100 | 500 | 500 |
|  | Amygdaloid body | 50> | 100 | 500 | 700 |
| Digestive organ | Pancreas | 100 | 200 | 50> | 50> |
|  | Small intestine | 50> | 50> | 50> | 100~500 |
|  | Stomach | 100 | 100~400 | 50> | 50> |
|  | Gall bladder | 100 | 50> | 50> | 50> |

EXAMPLE 11

Information about functions of BAI2 knockout mouse was obtained from the data base relating to knockout mouse functions (Deltagen).

BAI2 knockout mouse was prepared by gene disruption by homologous recombination. Specifically, gene disruption by homologous recombination was carried out by preparing a targeting vector for targeting a domain (876D-917L region) in the base sequence of mouse BAI2 gene (encoding 1560 amino acid residues) which encoded from aspartic acid (D) at position 876 to leucine (L) at position 917 of mouse BAI12, and introducing the targeting vector into ES cell derived from 129/OlaHsd mouse. The targeting vector included LacZ-Neo gene cassette that contained genome sequence 0.8 kb The tail suspension test is a technique that is ordinarily used as the test method to investigate a phenotype of depression, which comprises fixing a tail of a mouse to hang the mouse upside down, and measuring immorbility time before the mouse starts movement to escape from this state. The tail suspension test is used frequently as a test system for studying a possible relationship with depression, for example, for evaluating an anti-depressant drug (Steru L. et al., "Psychopharmacology" (Berl), 1985, Vol. 85, No. 3. p. 367-370; Crowley J. J. et al., "Pharmacological Biochemical Behavior", 2004, Vol. 78, No. 2 p. 269-274; Nielsen D. M. et al, "European Journal of Pharmacology", 2004, Vol. 499, Nos. 1-2, p. 135-146).

It is known that in the tail suspension test, the longer the immobility time, the more a depression state, and the shorter the immobility time, the more an anti-depressant state. For example, it is known that immobility time is shortened by administration of anti-depressant drug.

The tail suspension test was carried out using ten BAI2 knockout mice. As a control, the tail suspension test was carried out similarly using 16 wild type knockout mice.

The BAI2 knockout mice showed significantly reduced immobility time in the tail suspension test compared with wild type mice (FIG. 10). Results are shown by average±standard deviation of immobility time of each mouse in BAI2 knockout mouse group and wild type mouse group. A significant difference was obtained in statistical processing using t-test.

It can be postulated from the results of the tail suspension test that BAI2 knockout mice were in anti-depressant state. Since BAI2 knockout mice exhibited an anti-depressant-like phenotype, the inventors consider that BAI2 gene is involved in depressant.

BAI2 gene and splicing variants thereof are not expressed in BAI2 knockout mice, because of the destruction of BAI2 gene. Therefore, the inventors consider that that not only BAI2 gene but also splicing variants thereof are involved in depression.

EXAMPLE 12

Identification of a compound that inhibits a response of ph01207 gene product to a ligand was carried out with a system for measuring a change in intracellular calcium concentration using ph01207 expression cell line.

ph01207 expression cell line was constructed as follows. First, recombination was carried out between ph01207 cDNA clone identified in Example 1 and pcDNA3.1 (Invitrogen) by Asp718I (Boehriger) and NotI (TAKARA) to construct a ph01207 expression vector that did not contain an epitope-tag. ph01207 expression vector was transfected using Lipofectamine 2000 (Invitrogen) to CHO-K1 cell line that is a host cell, and selection of stably expressing cell line was carried out with a medium containing G418. Detection of the expression of introduced genes in cells was carried out by FCM analysis using anti-ph01207 antibody.

As a result, a plurality of cell lines that expressed ph01207 in a stable fashion was obtained. Identification of a compound was carried out using ph01207#3F8-17 cell line that was one of clones among them.

As a ligand, CCK-8S (Peptide Institute) was used. 0.52 mg of CCK-8S (SEQ ID NO: 14) was dissolved in 4.5 mL of 1% NaHCO$_3$ (Wako) to prepare a solution of 0.1 mM concentration. As a test compound, SoftFocus GPCR Target-Directed Library that is a compound library (BioFocus) was used. DMSO solution of every compound at 2 mg/mL was diluted 25-fold with PBS to adjust the concentration to 80 μg/mL for use.

Specifically, identification of a compound was carried out as follows. ph01207#3F8-17 cell line was seeded in 96-well plates (plates with a black wall surface and transparent bottom) at $3 \times 10^4$ cells/100 μL medium/well and cultured at 37° C. in the presence of 5% CO$_2$. DMEM/F12 (supplied by Gibco) containing 10% fetal calf serum (supplied by Moregate) was used as the medium. The next day, 20 μL of 6×loading buffer was added to each well to allow for a reaction at 37° C. for 1 h so as to incorporate fluorescent dye contained in the loading buffer into cells. The 6×loading buffer was prepared by dissolving component A of the FLIPR Calcium 3 Assay Kit (Molecular Devices Corp.) with component B followed by adding probenecid (Sigma) to have a final concentration of 15 mM. After the reaction, a change in the fluorescence intensity upon addition of CCK-8S (Peptide Institute) and compound was measured along with time for each well for 80 sec. As a control, similar measurements were taken using the buffer instead of a compound. 15 sec after the start of the measurement, the compound was added to have a final concentration of 10 μg/mL or the buffer was added. 35 sec after addition of the compound or the buffer, CCK-8S was added to have a final concentration of 10 nM. Measurement of the change along with time in the fluorescence intensity was carried out using FLEXstation (Molecular Devices Corp.).

Some of compounds tested inhibited the response of ph01207#3F8-17 cell line to CCK-8S. As typical examples, responses of ph01207#3F8-17 cell line to CCK-8S when adding with three kinds of compounds (compound A, compound B and compound C) respectively are shown in FIG. 11-A, FIG. 11-B and FIG. 11-C. Compound A, compound B and compound C are those compounds represented by aforementioned structural formulae (I), (II) and (III).

No change was observed in fluorescence intensity when compound A or the buffer was added 15 sec after the start of the measurement. When CCK-8S that is a ligand was added 35 sec after addition of the compound A or the buffer, fluorescence intensity was increased in the wells to which the buffer was added, and a response of ph01207#3F8-17 cell line to the ligand was observed, while such a response was inhibited in the wells to which the compound A was added (FIG. 11-A). This suggests that the compound A acts as an antagonist to an interaction between CCK-8S and ph01207.

Both compound B and compound C inhibited a response of ph01207#3F8-17 cell line to the ligand similarly to the compound A (FIG. 11-B and FIG. 11-C). This suggests that both compound B and compound C act as antagonists to an interaction between CCK-8S and ph01207.

From above mentioned results, the inventors considered that an antagonist that inhibits a response of ph01207 to ligand thereof such as CCK-8S can be identified by using a system for measuring a change in intracellular calcium concentration using ph01207 expression cell line.

INDUSTRIAL APPLICABILITY

According to the present invention there can be provided a protein acting as a functional membrane protein receptor that has a seven-span transmembrane domain which is considered to be a GPCR, and a DNA encoding the protein. The present protein is expressed on the cell membrane when expressed in a cell, and activates intracellular signal transduction by ligand stimulation to induce a cell response.

The present invention enables elucidation of signal transduction pathways and cell functions in which the present protein participates and the regulation thereof. The present invention also allows for prevention and/or treatment of diseases, for example, depression attributable to an abnormality in the present protein and/or the DNA.

Thus, the present invention is useful for contribution in a broad range of fields from basic science to pharmaceutical development.

SEQUENCE TABLE FREE TEXT

SEQ ID NO: 1: DNA encoding a novel functional membrane protein receptor
SEQ ID NO: 2: Protein encoded by the DNA consisting of the base sequence described in SEQ ID NO: 1
SEQ ID NO: 2: (297): (350) TSP-I domain
SEQ ID NO: 2: (352): (405) TSP-I domain
SEQ ID NO: 2: (408): (461) TSP-I domain SEQ ID NO: 2: (870): (890) transmembrane domain
SEQ ID NO: 2: (899): (919) transmembrane domain
SEQ ID NO: 2: (928): (948) transmembrane domain
SEQ ID NO: 2: (970): (990) transmembrane domain
SEQ ID NO: 2: (1012): (1032) transmembrane domain
SEQ ID NO: 2: (1087): (1107) transmembrane domain
SEQ ID NO: 2: (1114): (1134) transmembrane domain
SEQ ID NO: 3: Partial amino acid sequence presented in each c-terminal region of a peptide consisting of the amino acid sequence described in SEQ ID NO: 2, hBAI1 and hBAI2
SEQ ID NO: 4: A designed oligonucleotide for use as a primer
SEQ ID NO: 5: Designed oligonucleotide for use as a primer
SEQ ID NO: 6: Designed oligonucleotide for use as a primer
SEQ ID NO: 7: Designed oligonucleotide for use as a primer
SEQ ID NO: 8: Designed oligonucleotide for use as a primer
SEQ ID NO: 9: Designed oligonucleotide for use as a primer
SEQ ID NO: 10: Designed oligonucleotide for use as a primer
SEQ ID NO: 11: Designed oligonucleotide for use as a primer
SEQ ID NO: 12: Synthesized oligonucleotide
SEQ ID NO: 13: Synthesized oligonucleotide
SEQ ID NO: 14: CCK-8S
SEQ ID NO: 14: (2) (2) sulfated
SEQ ID NO: 15: Splicing variant of DNA described in SEQ ID NO: 1
SEQ ID NO: 16: Protein encoded by DNA represented by base sequence described in SEQ ID NO: 15
SEQ ID NO: 16: (297): (350) TSP-I domain
SEQ ID NO: 16: (353): (406) TSP-I domain
SEQ ID NO: 16: (815): (835) transmembrane domain
SEQ ID NO: 16: (844): (864) transmembrane domain
SEQ ID NO: 16: (873): (893) transmembrane domain
SEQ ID NO: 16: (915): (935) transmembrane domain
SEQ ID NO: 16: (957): (977) transmembrane domain
SEQ ID NO: 16: (1032): (1052) transmembrane domain
SEQ ID NO: 16: (1059): (1079) transmembrane domain
SEQ ID NO: 17: Splicing variant of DNA described in SEQ ID NO: 1
SEQ ID NO: 18: Protein encoded by DNA represented by base sequence described in SEQ ID NO: 17
SEQ ID NO: 18: (297): (350) TSP-I domain
SEQ ID NO: 18: (352): (405) TSP-I domain
SEQ ID NO: 18: (408): (461) TSP-I domain
SEQ ID NO: 18: (870): (890) transmembrane domain
SEQ ID NO: 18: (899): (919) transmembrane domain
SEQ ID NO: 18: (928): (948) transmembrane domain
SEQ ID NO: 18: (970): (990) transmembrane domain
SEQ ID NO: 18: (1012): (1032) transmembrane domain
SEQ ID NO: 18: (1087): (1107) transmembrane domain
SEQ ID NO: 18: (1114): (1134) transmembrane domain
SEQ ID NO: 19: Splicing variant of DNA described in SEQ ID NO: 1
SEQ ID NO: 20: Protein encoded by DNA represented by base sequence described in SEQ ID NO: 19
SEQ ID NO: 20: (297): (350) TSP-I domain
SEQ ID NO: 20: (352): (405) TSP-I domain
SEQ ID NO: 20: (407): (460) TSP-I domain
SEQ ID NO: 20: (463): (516) TSP-I domain
SEQ ID NO: 20: (925): (945) transmembrane domain
SEQ ID NO: 20: (954): (974) transmembrane domain
SEQ ID NO: 20: (983): (1003) transmembrane domain
SEQ ID NO: 20: (1025): (1045) transmembrane domain
SEQ ID NO: 20: (1067): (1087) transmembrane domain
SEQ ID NO: 20: (1142): (1162) transmembrane domain
SEQ ID NO: 20: (1169): (1189) transmembrane domain
SEQ ID NO: 21: DNA encoding hBAI2 and splicing variant of DNA described in SEQ ID NO: 1
SEQ ID NO: 22: Protein encoded by DNA represented by base sequence described in SEQ ID NO: 21
SEQ ID NO: 22: (297): (350) TSP-I domain
SEQ ID NO: 22: (352): (405) TSP-I domain
SEQ ID NO: 22: (407): (460) TSP-I domain
SEQ ID NO: 22: (463): (516) TSP-I domain
SEQ ID NO: 22: (925): (945) transmembrane domain
SEQ ID NO: 22: (954): (974) transmembrane domain
SEQ ID NO: 22: (983): (1003) transmembrane domain
SEQ ID NO: 22: (1025): (1045) transmembrane domain
SEQ ID NO: 22: (1067): (1087) transmembrane domain
SEQ ID NO: 22: (1142): (1162) transmembrane domain
SEQ ID NO: 22: (1169): (1189) transmembrane domain
SEQ ID NO: 23: Designed oligonucleotide for use as a primer
SEQ ID NO: 24: Designed oligonucleotide for use as a primer

What is claimed is:

1. A method for identifying a compound that inhibits or promotes a function of a protein comprising the amino acid sequence represented by SEQ ID NOs: 2, 16, 18, 20, or 22, said method comprising:
    allowing a transformant in which a recombinant vector containing a DNA that encodes the protein comprising the amino acid sequence represented by SEQ ID NOs: 2, 16, 18, 20 or 22 has been introduced or the HA-ph01207#10-6 cell line deposited under the Accession Number: FERM BP-10101 to co-exist with a test compound under conditions that enable interaction of the transformant or the cell line with the test compound;
    introducing a system to measure a function of the protein that is expressed on a cell membrane of the transformant or the cell line; and
    determining whether or not the test compound inhibits or promotes the function of the protein by detecting the existence or non-existence of, or a change in, the function of the protein,
    wherein the function of the protein is produced by addition of a peptide or peptides selected from a) cholecystokinin octapeptide sulfated form (CCK-8S) consisting of the amino acid sequence represented by SEQ ID NO: 14 or b) a peptide comprising an addition of one amino acid in the amino acid sequence of CCK-8S and having an effect equivalent to CCK-8S on the function of said protein.

2. The method according to claim 1, wherein the function is a function causing a change in intracellular calcium concentration in response to addition of the peptide or the peptides.

3. The method according to claim 1, Wherein the function is a function causing a change in cell membrane potential in response to addition of the peptide or the peptides.

4. The method according to claim 1, wherein said DNA consists of the base sequence represented by SEQ ID NOs: 1, 15, 17, 19 or 21.

5. A method for identifying a compound that inhibits or promotes a function of a protein comprising the amino acid sequence represented by SEQ ID NOs: 2, 16, 18, 20, or 22, comprising contacting a test compound with a cell containing a DNA that encodes the protein comprising the amino acid sequence represented by SEQ ID NOs: 2, 16, 18, 20 or 22;
    measuring a function of the protein expressed on a cell membrane of the cell; and
    determining whether the test compound reduces or enhances the function of the protein,
    wherein the function of the protein is produced by addition of a peptide or peptides selected from a) cholecystokinin octapeptide sulfated form (CCK-8S) consisting of the amino acid sequence represented by SEQ ID NO: 14 or b) a peptide comprising an addition of one amino acid in the amino acid sequence of CCK-8S and having an effect equivalent to CCK-8S on the function of said protein.

6. The method according to claim 5, wherein the function is a function causing a change in intracellular calcium concentration in response to addition of the peptide or the peptides.

7. The method according to claim 5, wherein the function is a function causing a change in cell membrane potential in response to addition of the peptide or the.

8. The method according to claim 5, wherein said DNA consists of the base sequence represented by SEQ ID NOs: 1, 15, 17, 19, or 21.

9. A method for identifying a compound that inhibits or promotes a function of a protein comprising the amino acid sequence represented by SEQ ID NOs: 2, 16, 18, 20, or 22, wherein the method comprises:
    bringing the protein comprising the amino acid sequence represented by SEQ ID NOs: 2, 16, 18, 20 or 22 to coexist with a test compound;
    measuring the function of the protein; and
    comparing the function of the protein in the presence of the test compound with a function of the protein in the absence of the test compound,
    wherein the function of the protein is produced by addition of a peptide or peptides selected from a) cholecystokinin octapeptide sulfated form (CCK-8S) consisting of the amino acid sequence represented by SEQ ID NO: 14 or b) a peptide comprising an addition of one amino acid in the amino acid sequence of CCK-8S and having an effect equivalent to CCK-8S on the function of said protein.

10. A method for identifying a compound that inhibits or promotes a function of a protein comprising the amino acid sequence represented by SEQ ID NOs: 2, 16, 18, 20, or 22, wherein the method comprises:
    contacting a transformant to which an expression vector containing a DNA that encodes the protein comprising the amino acid sequence represented by SEQ ID NOs: 2, 16, 18, 20 or 22 is transfected or the HA-ph1207#10-6 cell line deposited under the Accession Number: FERM BP-10101 with a test compound;
    obtaining a measurement for the protein expressed in the presence of the test compound;
    comparing the measurement for the protein expressed in the presence of the test compound with measurements of expression taken in the absence of the test compound; and
    selecting the test compound that inhibits the expression of the protein or the test compound that promotes the expression of the protein.

* * * * *

UNITED STATES PATENT AND TRADEMARK OFFICE
CERTIFICATE OF CORRECTION

PATENT NO. : 7,527,937 B2  Page 1 of 1
APPLICATION NO. : 11/436904
DATED : May 5, 2009
INVENTOR(S) : Ohara et al.

It is certified that error appears in the above-identified patent and that said Letters Patent is hereby corrected as shown below:

IN THE ABSTRACT:

Line 6, "That" should read --that--.

IN THE CLAIMS:

Claim 3, column 143, line 33, "Wherein" should read --wherein-- .

Claim 7, column 144, line 10, "peptide or the." should read --peptide or the peptides.--.

Signed and Sealed this

Second Day of June, 2009

JOHN DOLL
*Acting Director of the United States Patent and Trademark Office*